(12) United States Patent
Li et al.

(10) Patent No.: US 8,697,046 B2
(45) Date of Patent: Apr. 15, 2014

(54) METHODS OF ADMINISTERING INTERFERON GAMMA TO ABSORB FLUID FROM THE SUBRETINAL SPACE

(75) Inventors: Rong Li, Rockville, MD (US); Sheldon S. Miller, Bethesda, MD (US); Arvydas Maminishkis, Washington, DC (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 123 days.

(21) Appl. No.: 13/058,359

(22) PCT Filed: Aug. 14, 2009

(86) PCT No.: PCT/US2009/053808
§ 371 (c)(1),
(2), (4) Date: Mar. 11, 2011

(87) PCT Pub. No.: WO2010/019839
PCT Pub. Date: Feb. 18, 2010

(65) Prior Publication Data
US 2011/0305668 A1 Dec. 15, 2011

Related U.S. Application Data

(60) Provisional application No. 61/089,157, filed on Aug. 15, 2008.

(51) Int. Cl.
*A61K 38/21* (2006.01)
*A61K 38/00* (2006.01)
*C07K 14/57* (2006.01)

(52) U.S. Cl.
USPC ............................ 424/85.5; 530/351; 514/1.1

(58) Field of Classification Search
None
See application file for complete search history.

(56) References Cited

U.S. PATENT DOCUMENTS

| 6,413,245 B1 | 7/2002 | Yaacobi et al. | |
|---|---|---|---|
| 2005/0208102 A1* | 9/2005 | Schultz ......................... | 424/427 |
| 2007/0248569 A1* | 10/2007 | Eisenbach-Schwartz et al. ............................ | 424/85.2 |

FOREIGN PATENT DOCUMENTS

| EP | 0974358 | 1/2000 |
|---|---|---|
| WO | WO 02/98460 | 12/2002 |
| WO | WO 2010/019839 | 2/2010 |

OTHER PUBLICATIONS

Hjelmeland, L.M., et al. Antifibrotic and uveitogenic properties of gamma interferon in the rabbit eye. Graefe's Arch. Clin. Exp. Ophthalmol., 1992, vol. 230, p. 84-90.*

Yeoh, J. et al. A review of drug options in age-related macular degeneration therapy and potential new agents. Expert Opinion in Pharmacotherapy, 2006, vol. 7(17), p. 2355-2368.*
Boehm, et al, "Cellular Responses to Interfon-γ," Annu. Rev. Immunol, 1997, 15, 749-795.
Edelman, et al., "Epinephrine Stimulates Fluid Absorption Across Bovine Retinal Pigment Epithelium," Investigative Ophthalmology & Visual Science, Nov. 1991, 32, 12, 3033-3040.
Esqueriazi, et al., "Treatment of Biopsy Proved Conjunctival Intraepithelial Neoplasia with Topical Interferon alfa-2b," Br J Ophthalmal, Sep. 2005, 89, 1221-1229.
Faure, et al., "Role of Interferon Regulatory Factor-1 and Mitogen-activated Protein Kinase Pathways in the induction of Nitric Oxide Synthase-2 in Retinal Pigmented Epithelial Cells," The Journal of Biological Chemistry, Feb. 19, 1999, 274, 8, 4794-4800.
Gadsby, et al., "Control of CFTR Channel Gating by Phosphorylation and Nucleotide Hydrolysis," Physiological Reviews, Jan. 1999, 79, Suppl. 1, S77-S107.
Goh, et al., "p38 MAP Kinase is Required for STAT1 Serine Phosphorylation and Transcriptional Activation Induced by Interferons," the EMBO Journal, Oct. 1999, 18, 20, 5601-5608.
Hooks, et al., "Identification of the Lymphokines, Interferon-gamma and Interleukin-2, in Inflammatory Eye Diseases," Investigative Ophthalmology & Visual Science, Sep. 1988, 29, 9, 1444-1451.
Jia, et al., "Acrolein, a Toxicant in Cigarette Smoke, Causes Oxidative Damage and Mitochondrial Dysfunction in RPE Cells: Protection by (R)-α-Lipoic Acid," Investigative Ophthalmology & Visual Science, Jan. 2007, 48, 1, 339-348.
Joseph, et al., "Apical and Basal Membrane Ion Transport Mechanisms in Bovine Retinal Pigment Epithelium," Journal of Physiology, Apr. 1991, 435, 439-463.
Kelley, et al., "In vivo Alterations of IFN Regulatory Factor-1 and PIAS1 Protein Levels in Cystic Fibrosis Epithelium," The Journal of Clinical Investigation, Aug. 2000, 106, 3, 403-410.
Kotter et al., "Erosive Arthritis and Posterior Uveitis in Behcet's Disease: Treatment with Interferon α and Interferon γ," Clinical and Experimental Rheumatology, Jan. 1, 1996, 14, 3, 313-315.
Kulka, et al., "Differential Regulation of Cystic Fibrosis Transmembrane Conductance Regulator by Interferon γ in Mast Cells and Epithelial Cells," The Journal of Pharmacology and Experimental Therapeutics, Nov. 2005, 315, 2, 563-570.
Li, et al., "Interferon- γ Signaling in Human Retinal Pigment Epithelial Cells Mediated by STAT1, ICSBP, and IRF-1 Transcription Factors," Investigative Ophthalmology & Visual Science, Apr. 1999, 40, 5, 976-982.
Li, et al., "PDGF-C and -D Induced Proliferation/Migration of Human RPE Is Abolished by Inflammatory Cytokines," Investigative Ophthalmology & Visual Science, Dec. 2007, 48, 12, 5722-5732.
Li, et al., "Role of p38α Map Kinase in Type I Interferon Signaling," The Journal of Biological Chemistry, Jan. 9, 2004, 279, 2, 970-979.
Limb, et al., "Cytokines in Proliferative Vitreoretinopathy," Eye, 1991, 5, 686-693.
Lochner et al., "The Many Faces of H89: A Review," Cardiovascular Drug Reviews, Fall-Winter 2006, 24, 3-4, 261-274.

(Continued)

Primary Examiner — Robert Landsman
Assistant Examiner — Bruce D Hissong
(74) Attorney, Agent, or Firm — Baker & Hostetler LLP

(57) ABSTRACT

Particular aspects of the invention provide methods for decreasing the amount of fluid present in the subretinal space of the eye by administering interferon gamma to the basolateral side of the retinal pigment epithelium. Adverse ocular conditions associated with the accumulation of fluid in the subretinal space can be treated by administering an amount of interferon gamma to the basolateral side of the retinal pigment epithelium effective to remove excess fluid from the subretinal space.

18 Claims, 23 Drawing Sheets

(56) References Cited

OTHER PUBLICATIONS

Marninishkis, et al., "Confluent Monolayers of Cultured Human Fetal Retinal Pigment Epithelium Exhibit Morphology and Physiology of Native Tissue," Investigative Ophthalmology & Visual Science, Aug. 2006, 47, 3, 3612-3624.

Maminishkis, et al., "The P2Y$_2$ Receptor Agonist INS37217 Stimulates RPE Fluid Transport in Vitro and Retinal Reattachment in Rat," Investigative Ophthalmology & Visual Science, Nov. 2002, 43, 11, 3555-3566.

Muanprasat, et al., "Discovery of Glycine Hydrazide Pore-occluding CFTR Inhibitors: Mechanism, Structure-Activity Analysis, and In Vivo Efficacy," The Journal of General Physiology, Aug., 2004, 124, 125-137.

Murray, "Pharmacological PKA Inhibition: All May Not Be What It Seems," Science Signaling, Jun. 3, 2008, 1-6.

Ooi, et al., "Cytokines and Chemokines in Uveitis—Is there a Correlation with Clinical Phenotype?" Clinical Medicine & Research, Dec. 2006, 4, 4, 294-309.

Pearson, et al., "Mitogen-Activated Protein (MAP) Kinase Pathways: Regulation and Physiological Functions," Endocrine Reviews, Apr. 2001, 22, 2, 153-183.

Quinn et al., "Ion Transport Mechanisms in Native Human Retinal Pigment Epithelium," Investigative Ophthalmology & Visual Science, Dec. 1992, 33, 13, 3513-3527.

Quinn, et al., Adrenergic Receptor Activated Ion Transport in Human Fetal Retinal Pigment Epithelium, Investigative Ophthalmology & Visual Science, Jan. 2001, 42, 1, 255-264.

Schaeffer et al., "Mitogen-Activated Protein Kinases: Specific Messages from Ubiquitous Messengers," Molecular and Cellular Biology, Apr. 1999, 2435-2444.

Schechter, et al., "Regression of Presumed Primary Conjunctival and Corneal Intraepithelial Neoplasia With Topical Interferon Alpha-2b," Cornea, Jan. 2002, 21, 1, 6-11.

Sheppard, et al., "Structure and Function of the CFTR Chloride Channel," Physiological Reviews, Jan. 1999, 79, Suppl. 1, S23-45.

Shi, et al., "Control of Chemokine Gradients by the Retinal Pigment Epithelium," Investigative Ophthalmology & Visual Science, Oct. 2008, 49, 10, 4620-4630.

Stark, et al., "How Cells Respond to Interferons," Annu. Rev. Biochem, 1998, 67, 227-264.

Voloboueva, et al., "(R)-α-Lipoic Acid Protects Retinal Pigment Epithelial Cells from Oxidative Damage," Investigative Ophthalmology & Visual Science, Nov. 2005, 46, 11, 4302-4310.

Zhang et al., "The p38 Mitogen-Activated Protein Kinase Signaling Pathway Is Coupled to Toll-Like Receptor 5 to Mediate Gene Regulation in Response to Pseudomonas aeruginosa Infection in Human Airway Epithelial Cells," Infection and Immunity, Dec. 2007, 75, 12, 5985-5992.

* cited by examiner

Fig 23
E
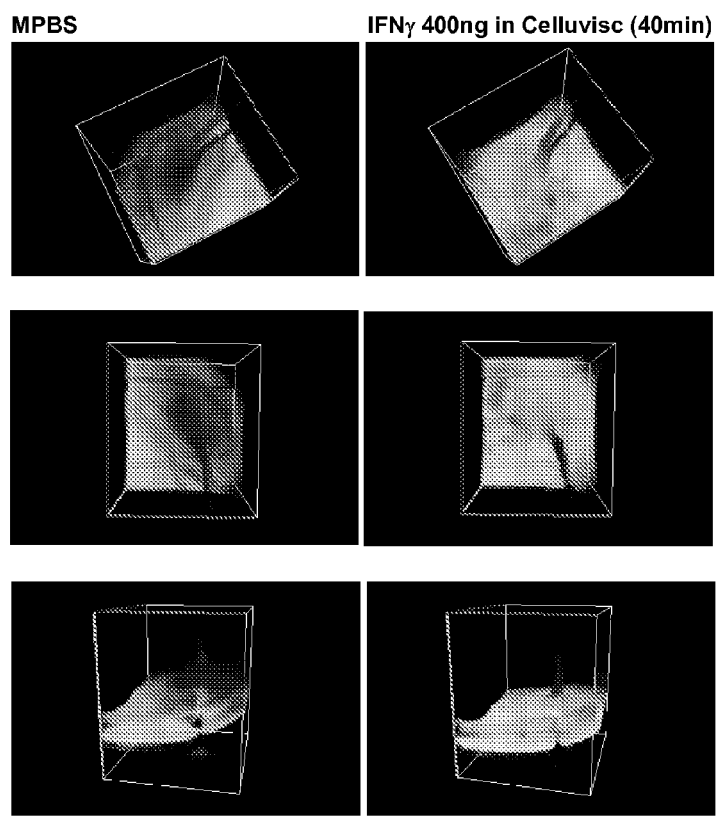
F
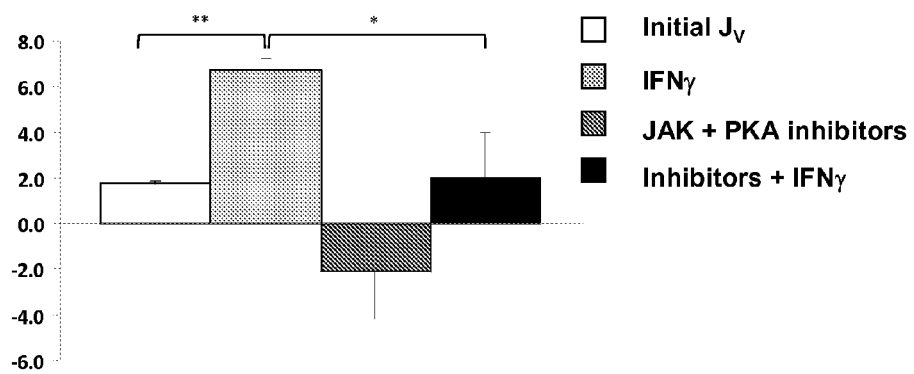

METHODS OF ADMINISTERING INTERFERON GAMMA TO ABSORB FLUID FROM THE SUBRETINAL SPACE

TECHNICAL FIELD

The present invention relates to methods of removing fluid from the subretinal space of the eye that comprise administering interferon-gamma (IFNγ) to the basolateral side of the retinal pigment epithelium. Particular aspects of the invention relate to using such methods to treat adverse ocular conditions associated with the accumulation of fluid in the subretinal space.

BACKGROUND

Interferon gamma (IFNγ) is a pleiotropic cytokine produced by T- and NK-cells and is involved in the regulation of both innate and adaptive immune responses. The major biological activities of IFNγ are associated with antiviral and immunomodulatory effects, cell grow and differentiation, and control of apoptosis (Stark, G., et al., *Annu Rev Biochem,* 1998, 67, 227-264; Ramana, C., et al., *Trends Immunol,* 2002, 23, 96-101; van Boxel-Dezaire, A., et al., *Curr Top Microbiol Immunol,* 2007, 316, 119-154). The IFNγ receptor is composed of two distinct subunits, IFNGR1 and IFNGR2, in which IFNGR1 is the major ligand-binding subunit, (Stark, G., et al., *Annu Rev Biochem,* 1998, 67, 227-264; Bach, E., et al., *Annu Rev Immunol,* 1997, 15, 563-591) while IFNGR2 plays a critical role in the generation of IFNγ signals (Hemmi, S., et al., *Cell,* 1994, 76, 803-810; Soh, J., et al., *Cell,* 1994, 76, 793-802). Interaction of IFNγ with its cell surface receptor activates receptor-associated Janus-activated kinase 1 (JAK1) and JAK2, which in turn phosphorylate and activate the signal transducer and activator of transcription-1α (STAT-1α). Phosphorylated STAT-1α dimerizes and translocates into the nucleus where it binds to well-defined DNA sequences called gamma interferon activation sites (GASs) in IFNγ-inducible promoters and activates the transcription of genes that encode members of the interferon regulatory factor (IRF) family of transcription factors (Stark, G., et al., *Annu Rev Biochem,* 1998, 67, 227-264; Boehm, U., et al., *Annu Rev Immunol,* 1997, 15, 749-795; Darnell, J. Jr., *Science,* 1997, 277, 1630-1635).

Ten members of the IRF family have been identified, including IRF-1, IRF-2, IRF-3, IRF-4/lymphoid-specific IRF/Pip/ICSAT, IRF-5, IRF-6, IRF-7, ICSBP/IRF-8, ISGF3γ/p48, and vIRF. IRF-1 and IRF-2 are the best-characterized members of this family (Nguyen, H., et al., *Cytokine Growth Factor Rev,* 1997, 8, 293-312; Miyamoto, M., et al., *Cell,* 1988, 54, 903-913; Harada, H., et al., *Cell,* 1989, 58, 729-739) and were initially identified by studies of transcriptional regulation of the IFN system. They have subsequently been shown to be key factors in the regulation of cell growth through their effects on the cell cycle (Taniguchi, T., et al., *J Cancer Res Clin Oncol,* 1995, 121, 516-520; Vaughan, P., et al., *J Mol Med,* 1997, 75, 348-359). IRF-1 is thought to function in a manner analogous to the tumor suppressor p53, activating a set of genes whose products are required for negative regulation of cell growth. IRF-2, which shares significant sequence similarity to IRF-1 within the DNA binding domain, represses IRF-1 regulatable genes (Taniguchi, T., *J Cell Physiol,* 1997, 173, 128-130). Although ICSBP/IRF-8 is thought to be expressed exclusively in cells of macrophage and lymphocyte lineage, (Driggers, P., et al., *Proc Natl Acad Sci USA,* 1990, 87, 3743-3747) it has been shown that the ICSBP gene is transcriptionally activated in human retinal pigment epithelium cell by IFNγ (Li, W., et al., *Invest Ophthalmol Vis Sci,* 1999, 40, 976-982).

In addition to JAK/STAT, IFNγ activates several other signal transduction proteins, including the mitogen-activated protein (MAP) kinases (Ramana, C., et al., *Trends Immunol,* 2002, 23, 96-101; van Boxel-Dezaire, A., et al., *Curr Top Microbiol Immunol,* 2007, 316, 119-154; Platanias, L., et al., *Exp Hematol,* 1999, 27, 1583-1592; Platanias, L., *Nat Rev Immunol,* 2005, 5, 375-386; Maher, S., et al., *Curr Med Chem,* 2007, 14, 1279-1289). MAP kinases are a superfamily of serine-threonine kinases that play important roles in various signal transduction pathways in mammalian cells. Three major MAP kinases have been identified—the extracellular signal—regulated kinase (ERK), the c-Jun $NH_2$ terminal kinase (JNK), and the P38 MAP kinase (Chang, L., et al., *Nature,* 2001, 410, 37-40; Schaeffer, H., et al., *Mol Cell Biol,* 1999, 19, 2435-2444). Although emerging evidence exists that suggests a role for P38 MAP kinase in mediating fast cellular responses to IFN stimulation and in maintaining a more sustained response through regulation of gene transcription, (Platanias, L., *Nat Rev Immunol,* 2005, 5, 375-386; Chang, L., et al., *Nature,* 2001, 410, 37-40; Katsoulidis, E., et al., *J Interferon Cytokine Res,* 2005, 25, 749-756; Platanias, L., *Pharmacol Ther,* 2003, 98, 129-142; Li, Y., et al., *J Biol Chem,* 2004, 279, 970-979; Pearson, G., et al., Endocr Rev, 2001, 22,153-183) the precise function P38 MAP kinase in IFN signaling remains unclear (Platanias, L., et al., *Exp Hematol,* 1999, 27, 1583-1592). P38 MAP kinase may function as an IFNα- and IFNγ-dependent serine kinase for STAT, which is needed for STAT1 transcriptional activity (Goh, K., et al., *Embo J,* 1999, 18, 5601-5608). It also appears that P38 MAP kinase plays a role in the induction of antiviral responses (Goh, K., et al., *Embo J,* 1999, 18, 5601-5608). In RPE cells, P38 MAPK has been shown to be activated in response to oxidative stress, but no evidence exists that IFNγ can activate P38 MAPK (Faure, V., et al., *J Biol Chem,* 1999, 274, 4794-4800). Recently it has been shown that P38 MAPK mediates the flagellin-induced activation of CFTR-dependent Cl secretion in Calu-3 airway epithelial cells (Zhang, Z., et al., *Infect Immun,* 2007, 75, 5985-5992; Illek et al., 2008, in press).

The cystic fibrosis transmembrane conductance regulator (CFTR) is a cAMP-dependent Cl channel located at the apical membrane of most epithelia. It helps to control transepithelial electrolyte transport, fluid flow, and the chemical composition of the extracellular spaces surrounding major organ systems such as intestine, sweat glands, lung and pancreas. CFTR belongs to the ATP binding cassette (ABC) superfamily of membrane proteins and has transmembrane domains (TMD1 and TMD), nucleotide binding domains (NBD1 and NBD2), and a regulatory (R) domain. The gating of CFTR is tightly regulated by protein phosphorylation and nucleotide concentration. It is now well-established that CFTR gene expression is regulated by many factors, including cytokines, in a cell- and stimulus-specific manner that can involve both transcriptional and posttranscriptional mechanisms (Kulka, M., et al., *J Pharmacol Exp Ther,* 2005, 315, 563-570).

As a lymphocyte effector molecule, IFNγ has been implicated in the pathogenesis of a number of intraocular inflammatory diseases of infectious or presumed autoimmune origin (Chiba, H., et al., *Sci STKE,* 2006, 2006, pe1; Fang, Y., et al., *Thyroid,* 2007, 17, 989-994; Willenborg, D., et al., *J Neuroimmunol,* 2007, 191, 16-25). In the eye, IFNγ plays important roles in macrophage activation and in the recruitment of inflammatory cells to sites of inflammation, and has been detected in vitreous aspirates of patients with uveitis, proliferative vitreoretinopathy, and other inflammatory eye diseases (Hooks, J., et al., *Invest Ophthalmol Vis Sci,* 1988, 29, 1444-1451; Limb, G., et al., *Eye,* 1991, 5(Pt 6), 686-693; Franks, W. et al., *Curr Eye Res,* 1992, 11 Suppl, 187-191; Ooi, K., et al., *Clin Med Res,* 2006, 4, 294-309). The retinal pigment epithelium (RPE), is a highly specialized derivative of the neuroectoderm with multiple roles in the maintenance of normal ocular function.

The retinal pigment epithelium (RPE) is single monolayer of epithelial cells, located in the back of the vertebrate eye, between the choroidal blood supply (choriocapillaris) and the neuroretina. The RPE acts as one of the components of the blood-retinal barrier, and RPE cells play vital roles in maintaining the visual cycle, in photoreceptor outer segment phagocytosis, and in transport of nutrients, metabolic waste products, ions, and fluid between the distal retina and the choriocapillaris. Dysfunction of RPE cells has been implicated in inflammatory and degenerative diseases of the retina and choroid, (Campochiaro, P., *Expert Opin Biol Ther,* 2004, 4, 1395-1402; Donoso, L., et al., *Surv Ophthalmol,* 2006, 51, 137-152; Voloboueva, L., et al., *Invest Ophthalmol Vis Sci,* 2005, 46, 4302-4310; Shi, G., et al., *Invest Ophthalmol Vis Sci,* 2008; Li, R., et al., Invest Ophthalmol Vis Sci, 2007, 48, 5722-5732; Jia, L., et al., *Invest Ophthalmol Vis Sci,* 2007, 48, 339-348) but relatively little is understood regarding the direct effects of inflammatory mediators on RPE physiology or pathophysiology.

A need thus exists in the art for elucidating whether IFNγ plays a role in the dysfunction of RPE cells in order to develop methods for treating the numerous ocular diseases and disorders associated with RPE dysfunction.

SUMMARY

The accumulation of subretinal fluid occurs in connection with numerous adverse ocular conditions. Applicants have discovered that IFNγ increases fluid transport from the neuroretina side of the RPE to the choroidal side of the RPE, leading to the absorption of excess fluid from the subretinal space. Particular aspects of the invention thus relate to methods for decreasing the amount of fluid present in the subretinal space of a patient that comprise administering an amount of interferon gamma to the eye of the patient effective to decrease the amount of fluid present in the subretinal space of the patient.

Further aspects of the invention are directed to methods for treating decreases in visual acuity that are associated with diseases or disorders that cause the accumulation of fluid in the subretinal space. Such methods comprise administering an amount of interferon gamma to the eyes of patients effective to decrease the amount of fluid present in the subretinal space of the patients.

Additional embodiments of the invention involve methods for treating age-related macular degeneration, chronic macular edema, diabetic retinopathy, retinal detachment, glaucoma, or uveitis that comprise decreasing the amount of fluid present in the subretinal space of patients suffering from such disorders by administering an amount of interferon gamma to the eyes of the patients effective to decrease the amount of fluid present in the subretinal space of the patients.

BRIEF DESCRIPTION OF THE DRAWINGS

FIG. 3A: Control RPE cells; FIG. 3B: RPE cells treated with 0.5 ng/ml IFNγ; FIG. 3C: RPE cells treated with 5 ng/ml IFNγ; FIG. 3D: RPE cells treated with 50 ng/ml IFNγ.

DETAILED DESCRIPTION OF ILLUSTRATIVE EMBODIMENTS

Figure 1A:
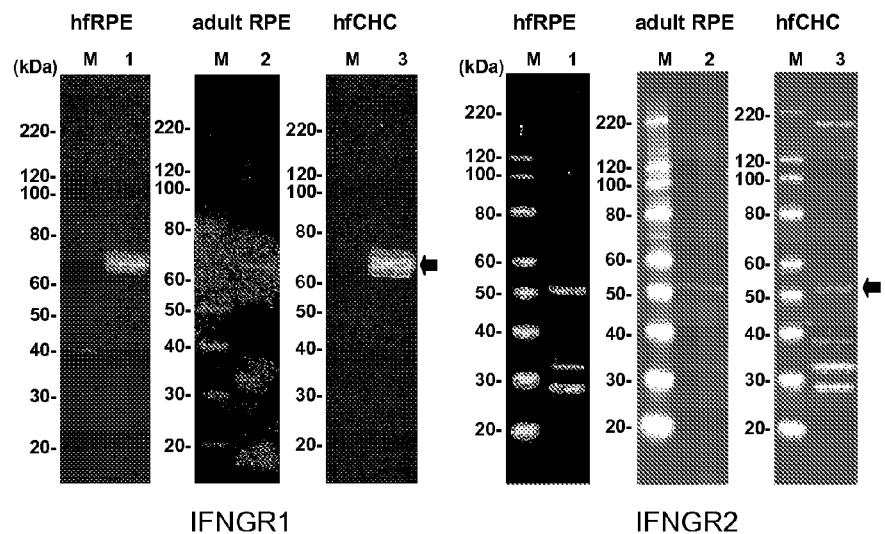
FIG. 1A is an image of several immunoblots depicting the expression of IFNGR1 and IFNGR2 in primary human fetal retinal pigment epithelial cultures (hfRPE; 1), native human adult RPE cultures (2), and primary human fetal choroidal cultures (hfCHC; 3), with a protein marker reference (M).

Retinal pigment epithelial (RPE) cells form a monolayer that regulates the transport of fluids, ions, and metabolites between the sensory retina and the vascular choroidal system. The RPE constitutes the outer part of the blood-retinal barrier, and impairment of this barrier causes subretinal fluid accumulation, which is associated with numerous adverse ocular conditions, such as retinal detachment, chronic macular edema, age-related macular degeneration, diabetic retinopathy, peripheral vitreoretinopathy, glaucoma, and uveitis. Applicants have surprisingly discovered that administration of interferon-gamma (IFNγ) to the basolateral side of the RPE increases fluid transport across the RPE, resulting in the absorption of fluid from the subretinal space. IFNγ can be administered to the basolateral side of the RPE by application to the anterior surface of the eye for the treatment of adverse ocular conditions in which subretinal fluid accumulation occurs.

Applicants have discovered that IFNγ increases fluid transport ($J_V$) from the neuroretina side of the RPE to the choroidal side of the RPE, and found that this activity is inhibited by an anti-human IFNγ R1 monoclonal antibody, Janus-activated kinase (JAK) inhibitor I, and a cystic fibrosis transmembrane conductance regulator (CFTR) inhibitor (CFTR$_{inh}$-172). Further, applicants have found that pretreatment with cyclohexamide (4 hours and 24 hours) significantly inhibited IFNγ-stimulated $J_V$ increase, indicating that de novo protein synthesis is at least partially needed to mediate the IFNγ-induced $J_V$ change. Applicants have further demonstrated that IFNγ-stimulated $J_V$ increase is blocked to a significant degree by the protein kinase A (PKA) inhibitors, H-89 and Rp-8-Br-cAMPS, which block the activation of CFTR. Finally, IFNγ activates the P38 mitogen-activated protein kinase (MAPK) signaling pathway, and applicants discovered that P38 MAPK inhibitors significantly reduced IFNγ-induced $J_V$ increase, which was further decreased by the subsequent addition of CFTR$_{inh}$-172.

Applicants have demonstrated that IFNγ significantly increases fluid absorption ($J_V$) across the RPE, whether added acutely or chronically, and the effect occurs if IFNγ is added to the basal bath or to both the apical and basal baths, but not if IFNγ is added only to the apical bath. IFNγ receptors have two subunits, IFNGR1 and IFNGR2. In human fetal RPE (hfRPE), IFNGR1 is mainly located at the basolateral membrane while IFNGR2 is located at both the apical and basolateral membranes. Applicants have discovered that pretreatment of both the apical and basolateral membranes with anti-IFNGR1 blocking antibody specifically inhibits IFNγ-induced $J_V$ increase.

As used herein, the phrase "decrease in visual acuity" refers to any diminishing or lessening of the acuteness or clearness of vision, and can refer to any measurable diminishing or lessening in the acuteness or clearness of form vision, which is dependent on the sharpness of the retinal focus within the eye and the sensitivity of the interpretative faculty of the brain.

As used herein, the phrase "accumulation of fluid in the subretinal space" refers to an increase in the amount of fluid present in the space that separates the retinal pigment epithelium (RPE) from the outer segments of the photoreceptors beyond the amount of fluid normally present in that space in healthy eyes. The phrase "decrease the amount of fluid present in the subretinal space," and all variations thereof, refers to any lessening or diminishing of the amount of fluid present in the space that separates the retinal pigment epithelium (RPE) from the outer segments of the photoreceptors.

As used herein, the phrase "basolateral side of the retinal pigment epithelium" refers to the side of the retinal pigment epithelium that is adjacent to, borders, or faces, the choroid.

As used herein, the phrase "anterior surface of the eye" refers to portion of the cornea that comprises the exterior, exposed part of the eye.

As used herein, the phrase "subretinal injection" refers to the introduction by any means of a substance into the subretinal space.

As used herein, the phrase "subtenon injection" refers to the introduction by any means of a substance into the area below the Tenon's capsule and above the sclera of the eye at a point posterior to a limbus of the eye.

Certain aspects of the invention relate to methods for treating decreases in visual acuity, particularly decreases in visual acuity associated with diseases and disorders that cause the accumulation of fluid in the subretinal space, that involve administering an amount of interferon gamma to the eye of a patient effective to decrease the amount of fluid present in the subretinal space of the patient. Such methods can be used, for example, to treat age-related macular degeneration, chronic macular edema, diabetic retinopathy, glaucoma, peripheral vitreoretinopathy, uveitis, or retinal detachment caused by, for example, retinal injury or surgery. In this regard, further aspects of the invention relate to methods for treating age-related macular degeneration, chronic macular edema, diabetic retinopathy, peripheral vitreoretinopathy, retinal detachment caused by, for example, retinal injury or surgery, glaucoma, or uveitis that comprise decreasing the amount of fluid present in the subretinal space of a patient. In such methods an amount of interferon gamma is administered to the eye of the patient effective to decrease the amount of fluid present in the subretinal space of the patient.

A wide variety of diseases of the eye may be readily treated or prevented according to particular embodiments of the invention, including for example, glaucoma, macular degeneration, diabetic retinopathies, uveitis, inherited retinal degeneration such as retinitis pigmentosa, retinal detachment or injury, and retinopathies, whether inherited, induced by surgery, trauma, a toxic compound or agent, or photically.

For example, within one embodiment of the invention, IFNγ is administered to a patient's eye in order to treat or prevent macular degeneration. Briefly, the leading cause of visual loss in the elderly is macular degeneration (MD), which has an increasingly important social and economic impact in the United States. As the size of the elderly population increases in this country, age related macular degeneration (AMD) will become a more prevalent cause of blindness than both diabetic retinopathy and glaucoma combined. Although laser treatment has been shown to reduce the risk of extensive macular scarring from the "wet" or neovascular form of the disease, there are currently no effective treatments for the vast majority of patients with MD.

Within another embodiment, IFNγ can be administered to a patient's eye in order to treat an inherited retinal degeneration. One of the most common inherited retinal degenerations is retinitis pigmentosa (RP), which results in the destruction of photoreceptor cells, and the RPE. Other inherited conditions include bardet-biedl syndrome (autosomal recessive); congenital amaurosis (autosomal recessive); cone or cone-rod dystrophy (autosomal dominant and X-linked forms); congenital stationary night blindness (autosomal dominant, autosomal recessive and X-linked forms); macular degeneration (autosomal dominant and autosomal recessive forms); optic atrophy, (autosomal dominant and X-linked forms); retinitis pigmentosa (autosomal dominant, autosomal recessive and X-linked forms); syndromic or systemic retinopathy (autosomal dominant, autosomal recessive and X-linked forms); and usher syndrome (autosomal recessive). This group of debilitating conditions affects approximately 100,000 people in the United States alone.

Within other aspects of the invention, IFNγ is administered to a patient's eye to treat or prevent glaucoma. Briefly, glaucoma is not a uniform disease but rather is a heterogeneous group of disorders that share a distinct type of optic nerve damage that leads to loss of visual function. The disease is manifest as a progressive optic neuropathy that, if left untreated, leads to blindness. It is estimated that as many as 3 million Americans have glaucoma and, of these, as many as 120,000 are blind as a result. Furthermore, it is the number one cause of blindness in African-Americans. Its most prevalent form, primary open-angle glaucoma, can be insidious. This form usually begins in midlife and progresses slowly but relentlessly. If detected early, disease progression can frequently be arrested or slowed with medical and surgical treatment.

Within yet other embodiments of the invention, IFNγ can be administered to a patient's eye to treat or prevent injuries to the retina, including retinal detachment, photic retinopathies, surgery-induced retinopathies, toxic retinopathies, retinopathies due to trauma or penetrating lesions of the eye.

The present invention also provides methods of treating, preventing, or inhibiting neovascular disease of the eye, comprising the step of administering IFNγ to a patient's eye. Representative examples of neovascular diseases include diabetic retinopathy, AMD (wet form), and retinopathy of prematurity. Briefly, choroidal neovascularization is a hallmark of exudative or wet Age-related Macular Degeneration (AMD), the leading cause of blindness in the elderly population. Retinal neovascularization occurs in diseases such as diabetic retinapathy and retinopathy of prematurity (ROP), the most common cause of blindness in the young.

Further aspects of the invention relate to methods for decreasing the amount of fluid present in the subretinal space of a patient. Such methods can be used, for example, to treat patients suffering from diseases and disorders associates with the accumulation of fluid in the subretinal space. Accordingly, in certain aspects of such methods, the patient suffers from age-related macular degeneration, chronic macular edema, diabetic retinopathy, glaucoma, uveitis, peripheral vitreoretinopathy, or retinal detachment caused by, for example, retinal injury or surgery.

In preferred aspects, such methods involve administering an amount of interferon gamma to the eye of the patient effective to decrease the amount of fluid present in the subretinal space of the patient.

In preferred embodiments of the methods of the invention, IFNγ is administered to the basolateral side of the retinal pigment epithelium. The IFNγ can be administered to the basolateral side of the retinal pigment epithelium by administration to the anterior surface of the eye. Alternatively, the IFNγ can be administered to the basolateral side of the retinal pigment epithelium by subtenon injection or by subretinal injection. In preferred embodiments of the invention, IFNγ is administered to the anterior surface of the eye.

The present invention also provides a composition comprising IFNγ in a pharmaceutically acceptable carrier, in the form of an aqueous solution, a gel, or a gel-like formulation. The pharmaceutically acceptable carrier is a physiologically compatible vehicle, which may include, for example, one or more water soluble polyethers such as polyethylene glycol, polyvinyls such as polyvinyl alcohol and povidone, cellulose derivatives such as methylcellulose and hydroxypropyl methylcellulose, petroleum derivatives such as mineral oil and white petrolatum, animal fats such as lanolin, polymers of acrylic acid such as carboxypolymethylene gel, vegetable fats such as peanut oil, polysaccharides such as dextrans, glycosaminoglycans such as sodium hyaluronate or hyaluronic acid, salts such as sodium chloride and potassium chloride, lanolin, or glycine. In preferred embodiments of the invention, the carrier is a saline solution or is a CELLUVISC® solution.

When the composition is in the form of an aqueous solution, it may comprise physiologically safe excipients formulated to an osmolarity between 250-350 mOsm and pH5-9; preferably 280-300 mOsM and pH7.0-7.6. When the pharmaceutical formulation is in the form of a gel or gel-like formulation, it is preferably a hyaluronic acid or hyaluronic acid-containing formulation approved for intraocular use.

The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc. The composition optionally comprises an intraocular irrigation solution approved for surgical use.

The concentration of IFNγ in the compositions can vary widely, i.e., from less than about 0.01% to more than about 1%, and will be determined primarily based upon fluid volumes, viscosities, etc., in accordance with the particular mode of administration used.

The compositions may be sterilized by conventional, well known sterilization techniques, or may be sterile filtered. The resulting aqueous solutions may be packaged for use as is, or lyophilized, the lyophilized preparation being combined with a sterile solution prior to administration.

The compositions can be formulated as polymer matrices, hydrogel matrices, polymer implants, or encapsulated formulations to allow slow or sustained release of the compositions. A particularly preferred formulation is a suspension or solution of the delivery system in a topical ocular formulation, such as eye drops.

The dosage of IFNγ administered in the compositions can range from about 5 ng/ml to about 100 mg/ml, but should not exceed 4 mg in single dose. In certain embodiments of the invention, IFNγ is administered at a dose of about 20 ng/ml to about 25 mg/ml, at a dose of about 80 ng/ml to about 6 mg/ml, at a dose of about 300 ng/ml to about 1 mg/ml, or at a dose of about 650 ng/ml.

Compositions containing IFNγ can be administered to the eyes of a patient using any suitable means, but are preferably applied to the anterior surface of the eye using methods familiar to those skilled in the art. For example, in certain embodiments of the invention, the compositions are applied to the eye via liposomes. Further, in other embodiments the compositions are infused into the tear film via a pump-catheter system. Another embodiment of the present invention relates to the compositions contained within a continuous or selective-release device, for example, membranes such as, but not limited to, those employed in the Ocusert™ System (Alza Corp., Palo Alto, Calif.). As an additional embodiment, the compositions are contained within, carried by, or attached to, contact lenses that are placed on the eye. Another embodiment of the present invention involves the compositions contained within a swab or sponge that is applied to the ocular surface. Further embodiments of the present invention involve the compositions contained within a liquid spray that is applied to the ocular surface. Still further embodiments of the present invention involve injection of the compositions directly into the lachrymal tissues or onto the eye surface. In particularly preferred embodiments of the invention, the compositions are applied to the surface of the eye using conventional eye droppers.

In some embodiments of the invention, the compositions of the invention are administered directly into the eye, such as to the subretinal space. In certain of such embodiments, the compositions are administered by subretinal injection using means familiar to those skilled in the art. In other embodiments, the compositions are administered by subtenon injection, as described, for example, in U.S. Pat. No. 6,413,245, incorporated herein by reference in its entirety.

The compositions of the present invention can be administered in a single dose or in multiple doses. For example, the compositions can be administered at the time of eye surgery. Alternatively, the compositions of the present invention can be administered over a course of treatment ranging from weeks to years. In certain embodiments of the invention, sustained release formulations such as implants are administered for the long-term treatment of diseases and disorders amenable to such modes of administration. In exemplary sustained release formulations, IFNα is delivered over a period of 24 to 72 hours. In preferred embodiments of the invention, a single dose of the compositions is administered. In alternative embodiments, multiple doses of the compositions are administered, for example, every 12, 24, 36, or 48 hours.

Within further embodiments of the invention, IFNγ is administered to a patient in combination with other active agents, methods, or therapeutic regimens, including for example, photodynamic therapy (e.g., for wet AMD), laser photocoagulation (e.g., for diabetic retinopathy and wet AMD), and intraocular pressure reducing drugs (e.g., for glaucoma).

The following examples are illustrative of certain embodiments of the invention and should not be considered to limit the scope of the invention.

Example 1

Cell Culture

The research followed the tenets of the Declaration of Helsinki and the NIH Institutional Review Board. Fetal eyes (gestation, 16-18 weeks) were obtained from Advanced Bioscience Resources (Alameda, Calif.) and adult eyes were obtained from Analytical Biological Services Inc. (Wilmington, Del.). Human fetal RPE (hfRPE) and cells from human fetal choroid (hfCH) were isolated and cultured using MEM-α based modified medium as described previously in Maminishkis, A., et al., *Invest Ophthalmol Vis Sci,* 2006, 47, 3612-3624, incorporated herein by reference in its entirety. For immunofluorescence localization and fluid transport experiments, cells were seeded in transwell chambers and maintained for 6 weeks before experiments. (Corning Costar, 0.4 μm pores, polyester membrane). The confluent monolayers were monitored for their morphology, pigmentation, polarity, and physiology, and confluent monolayers exhibiting the same properties of native RPE were used, as described in Volobouev, L. A., et al. *Invest Ophthalmol Vis Sci,* 2005, 46, 4302-4310; Shi, G., et al., *Invest Ophthalmol Vis Sci,* 2008; Li, R., et al., *Invest Ophthalmol Vis Sci,* 2007, 48, 5722-5732; and Maminishkis, A., et al., *Invest Ophthalmol Vis Sci,* 2006, 47, 3612-3624, each incorporated herein by reference in its entirety.

Example 2

Quantitative Real-Time Polymerase Chain Reaction (qRT-PCR)

qRT-PCR was performed as previously described in Li, R. et al., 2007, *Invest Ophthalmol Vis Sci,* 48, 5722-5732, incorporated by reference in its entirety herein. Confluent monolayers of hfRPE cultured in 24-well plates were treated with IFNγ (25 ng/ml) in SFM and harvested at 0 minutes, 30 minutes, 2 hours, 6 hours, 15 hours and 24 hours, in triplicate for each time point. 1 μg total mRNA isolated from the harvested cells (RNeasy Kit, Qiagen) was reverse-transcribed (SuperScript® III First-Strand Synthesis System for RT-PCR, Invitrogen). Real-time PCR (TaqMan®, Applied Biosystems) was used to quantify expression of the interferon regulatory factors IRF-1, IRF-2, and IRF-8; signal transducer and activator of transcription 1 (STAT1); suppressor of cytokine signaling 3 (SOCS3); protein inhibitor of activated STAT1 (PIAS1); inducible nitric oxide synthase (NOS2A); IFNγ receptor subunit R1 (IFNGR1); IFNα receptor subunit R1 (IFNAR1); IFNγ receptor subunit R2 (IFNGR2); cystic fibrosis transmembrane conductance regulator (CFTR); and Glyceraldehyde 3-phosphate dehydrogenase (GAPDH). The mRNA concentration of each gene was normalized against GAPDH. qRT-PCR was performed on the ABI Sequence Detection System 7900 (Applied Biosystems).

Example 3

Immunoblotting

Immunoblotting was performed as previously described in Li, R. et al., 2007, *Invest Ophthalmol Vis Sci*, 48, 5722-5732, incorporated by reference in its entirety herein. Primary cultures of hfRPE and native human adult RPE cells were lysed using RIPA buffer (Sigma-Aldrich) supplemented with proteinase inhibitor cocktail (Roche). Total protein in the supernatant was measured (BCA™ protein assay, Pierce Biotechnology) and 20 µg of protein from cell lysate supernatants was electrophoresed on a 4-12% gradient Bis-Tris NuPAGE gel (Invitrogen) under reduced or non-reduced conditions. Resolved proteins were transferred to nitrocellulose membranes (membranes and XCell II™ Blot Module, Invitrogen).

The membranes were incubated with mouse anti-human IFNγ R1 monoclonal antibody (R&D Systems), anti-human IFNγ R2 (Santa Cruz Biotechnology), anti-human IFNAR1, anti-human IFNAR2 (Abcam), anti-IRF1, anti-IRF2, anti-IRF8 (Santa Cruz Biotechnology) or anti-CFTR antibody 217 (Cystic Fibrosis Foundation Therapeutics Inc., Bethesda, Md.), after blocking non-specific binding ((StartingBlock™ T20 (TBS), Pierce Biotechnology). Membranes were then incubated with horseradish peroxidase (HRP) conjugated secondary antibody (Pierce Biotechnology) and visualized using Supersignal® West Dura Extended Duration Substrate (Pierce Biotechnology) and imaged using an Autochemie™ system (UVP, Upland, Calif.). The antibody-specific bands for IRF-1, IRF-2, ICSBP (IRF-8) and GAPDH were around 91 kDa, 50 kDa, 50 kDa, 48 kDa, and 37 kDa, respectively.

For phosphorylation studies, cells were starved for 24 hours in serum-free medium ("SFM," MEM-α modification medium containing non-essential amino acids and Glutamine-Penicillin-Streptomycin). Cells were treated with IFNγ (5-50 ng/ml) in SFM at various time points at 37° C. and lysed with RIPA buffer supplemented with proteinase inhibitor cocktail (Roche) and Halt™ phosphatase inhibitor cocktail (Pierce Biotechnology). 40 µg of protein was electrophoresed. As in the immunoblotting experiments described above, except that the membranes were incubated with anti-phospho-p38 MAP kinase (Thr180/Tyr182), anti-p38 MAP kinase, anti-phospho-Stat1 (Tyr701), anti-phospho-Stat1 (Ser727) or anti-Stat1 antibodies, respectively (each from Cell signaling Technology, Danvers, Mass.). The antibody-specific bands for STAT1/phospho-STAT1 (Tyr701) were around 84 kDa. GAPDH was blotted together with anti-GAPDH antibody (Abcam) and used as loading control. Cyclohexamide ("CHX"; Sigma-Aldrich), a protein synthesis inhibitor, was used at 62 µM.

For CFTR immunoblotting analysis, confluent monolayers of hfRPE were homogenized on ice in isolation solution (250 mM Sucrose, 10 mM Tris-HCl, mM $MgCl_2$, 1 mM $CaCl_2$, pH 7.4) supplemented with Halt™ protease inhibitor cocktail, EDTA-free. Nuclei and intact cells were removed with centrifugation (900×g for 10 minutes at 4° C., followed by centrifugation at 10,000×g for 5 minutes). Crude plasma membrane proteins were collected after centrifugation at 100,000×g for 1 hour at 4° C. In some of the experiments, membrane protein extracts from Calu-3 cells were used as positive control for CFTR, which showed major mature bands at 170 kDa.

Example 4

Immunofluorescence

For localization experiments, primary antibodies against IFNGR1, IFNGR2, CFTR, and ZO-1 (Zymed) were labeled with Zenon technology following the manufacturer's instructions (Invitrogen) and used to localize the respective proteins on hfRPE as described previously in Li, R. et al., 2007, *Invest Ophthalmol Vis Sci*, 48, 5722-5732, incorporated by reference in its entirety herein. Briefly, primary cultures of hfRPE monolayers on transwell plates were fixed with 4% formaldehyde, permeabilized for 10 minutes with 0.2% Triton X-100, and blocked with a signal enhancer (Image-iT FX; Invitrogen). Monolayers were incubated with antibodies pre-labeled with fluorophores. Normal serum (Invitrogen) was used as the negative control. Samples were mounted on glass slides with anti-fade reagent containing DAPI (Prolong Gold; Invitrogen) and imaged with a Zeiss Axioplan 2 microscope with apotome using Axiovision 3.4 software.

Example 5

JC-1 Staining

Mitochondrial membrane potential change ($\psi$) was assessed in live hfRPE cells using the lipophilic cationic probe 5,5',6,6'-tetrachloro-1,1'3,3'-tetraethylbenzimidazolcarbocyanine iodide (JC-1) following the manufacturer's instructions and as described in Voloboueva, L. A., et al., *Invest Ophthalmol Vis Sci*, 2005, 46, 4302-4310, incorporated herein by reference in its entirety. Confluent monolayers of hfRPE were treated with different concentrations of IFNγ (0.5, 5, 50 ng/ml) for 24, 48, or 72 hours and then incubated with JC-1 solution for 30 minutes at 37° C. Fluorescence was evaluated with a Zeiss Axiovert 25 inverted microscope.

Example 6

Bromodeoxyuridine (BrdU) Incorporation Assay

BrdU incorporation was performed as described in Li, R. et al., 2007, *Invest Ophthalmol Vis Sci*, 48, 5722-5732, incorporated by reference in its entirety herein. IFNγ, TNFα, and IL-1β were obtained from Peprotech, Rocky Hill, N.J., and Universal Type I Interferon (cat: 11200-1) or human interferon beta 1a were from PBL biomedical laboratories (New Brunswick, N.J.). Cumulative effects were measured by adding $VEGF_{165}$, EGF and bFGF (Peprotech), and PDGF-BB (R & D Systems) with IFNγ. Anti-human IFNγ R1 blocking antibody (R & D Systems, Minneapolis, Minn.), JAK inhibitor I, AG490, or JAK3 inhibitor II (EMD Biosciences, Gibbstown, N.J.) was added to the cells one hour prior to the addition of IFNγ. SFM was used as the negative control and SFM supplemented with 5% serum was used as positive control. After treatment for 48 hours, RPE cells were incubated with BrdU for 24 hours. The proliferation rate was evaluated using a Cell proliferation ELISA BrdU Kit (Roche, Ind.). Quadruplicate wells were used for each condition and the experiments were repeated at least two times using cell cultures from different donors. Cell viability was evaluated using a Live/Dead Viability/Cytotoxicity Kit (Invitrogen).

Example 7

Wound Healing Assay

The wound healing assay was used to study the effects of inflammatory cytokines on hfRPE cell migration, as described previously in Li, R., et al. *Invest Ophthalmol Vis Sci*, 2007, 48, 5722-5732, incorporated herein by reference in its entirety. Cell proliferation was suppressed by incubation with 10 μg/ml mitomycin C (Sigma) for 2 hours before all migration experiments. A circular denuded area (7 mm in diameter) was made in each well using a custom designed cell scraper. After incubation with various inflammatory cytokines for 48 hours, cells were fixed with cold methanol and stained with ethidium homodimer-1 (EthD-1, Invitrogen) according to the manufacturer's instructions. Cell migration was quantified by counting the average number of cells that migrated into the denuded area in 16 microscope fields surrounding the circumference of the denuded area. Each condition was tested in triplicate and repeated using cells from different donors.

Example 8

Cyclic AMP Assay

Intracellular cAMP levels were assayed with a cAMP-screen ELISA system (Applied Biosystems) following the manufacturer's protocol. Briefly, confluent monolayers of hfRPE cells cultured in 24-well plates were starved in SFM for 4 hours and then treated with IFNγ (0.5, 5, and 50 ng/ml), forskolin (10 μM), or forskolin (10 μM) and isobutylmethylxanthine (IBMX; 0.5 mM) for 5 minutes, 30 minutes, 4 hours, 16 hours, or 24 hours. For some of the experiments, cells were treated with IBMX (0.5 mM) for 30 minutes, and then IFNγ or forskolin was added. Cells were lysed and the supernatant collected after centrifugation. Samples were incubated with anti-cAMP antibody and cAMP-AP in a 96-well assay plate; serial dilutions of cAMP served as standards. The plate was incubated with substrate and the chemiluminescence signal measured with a SpectraMax M2 microplate reader (Molecular Devices). The standard curve was obtained by best fit with a weighted 4-parameter logistic curve and the cAMP concentration was calculated and normalized with total protein concentration.

Example 9

Fluid Transport

Confluent monolayers of hfRPE cultured on transwells were mounted in a modified Üssing chamber and transepithelial water flow measurements ($J_V$) were made with a capacitance probe technique as described previously in Maminishkis, A., et al., *Invest Ophthalmol Vis Sci*, 2006, 47, 3612-3624; Shi, G., et al., *Invest Ophthalmol Vis Sci*, 2008, 49, 4620-4630; Edelman, J. L., et al., *Invest Ophthalmol Vis Sci*, 1991, 32, 3033-3040; Jiang, C., et al., *Science*, 1993, 262, 424-427; and Maminishkis, A., et al., *Invest Ophthalmol Vis Sci*, 2002, 43, 3555-3566, each incorporated herein by reference in its entirety.

Tissue viability was ascertained by recording transepithelial potential (TEP) and total tissue resistance ($R_T$). It should be noted that the solution composition changes in this chamber were relatively slow (≈1-2 chamber volumes per minute) and the data sampling rate was once per minute, more than two orders of magnitude slower than the sampling rate in the electrophysiology chamber (see below). Therefore it was not possible to record fast changes, in seconds or minutes, in $J_V$, TEP, or $R_T$. After addition of IFNγ to the apical or basal baths, steady-state $J_V$, TEP, and $R_T$ were recorded for 20-30 minutes. In control experiments, successive additions of IFNγ were made to test for the repeatability and reversibility of responses. To block IFNγ effects, RPE cells were incubated for 30-60 minutes with a blocking antibody against IFNγR1, JAK inhibitor I, PKA inhibitors (H-89, EMD Biosciences; RP-8-Br-cAMPS, Sigma-Aldrich), nitric oxide synthase inhibitor (aminoguanidine hydrochloride, Sigma-Aldrich), P38 MAPK inhibitors (SB203580 or SB20290), or CHX. Other components of this signaling pathway were studied using P38 MAPK inhibitors (SB203580 and SB202190). Relatively specific Cl channel inhibitors, CFTRinh-172 or DIDS (EMD Biosciences, La Jolla, Calif.), were used to block cAMP or $Ca^{2+}$-activated Cl channels; experiments with CFTRinh-172 were performed as described in Muanprasat, C., et al., *J Gen Physiol*, 2004, 124, 125-137, incorporated herein by reference in its entirety. In chronic experiments, paired hfRPE tissues with matched $R_T$ values were incubated for 4-24 hours with IFNγ or CHX. The subsequent changes in $J_V$, $R_T$, and TEP were measured in Ringer's solution or serum free cell culture media as previously described in Shi, G., et al., *Invest Ophthalmol Vis Sci*, 2008 and Maminishkis, A., et al., *Invest Ophthalmol Vis Sci*, 2006, 47, 3612-3624, each incorporated herein by reference in its entirety. Intracellular levels of NO were elevated with 1-Hydroxy-2-oxo-3-(3-aminopropyl)-3-isopropyl-1-triazene (NOC-5, Enzo Life Sciences, Plymouth, Pa.). 8-Br-cGMP was purchased from Sigma-Aldrich.

Example 10

Electrophysiology

Equivalent circuit analysis and electrophysiological methods have been previously described in Quinn, R. H., et al., *Invest Ophthalmol Vis Sci*, 1992, 33, 3513-3527; Joseph D. P., et al., *J Physiol*, 1991, 435, 439-463; and Maminishkis, A., et al., 2006, *Ophthalmol Vis Sci*, 47, 3612-3624 each incorporated herein by reference in its entirety.

Briefly, confluent monolayers of cultured hfRPE were mounted on a nylon mesh support and clamped into a modified Üssing chamber that allowed the rapid exchange of Ringer's solution (≈10 chamber volumes per minute) and the measurement of fast electrical changes in seconds. The electrical connections to the apical and basal chambers were made with Ringer-agar bridges in series with calomel electrodes. Intracellular potentials were recorded with conventional microelectrodes, back-filled with 150 mM KCl, with resistances of 80 to 200 MΩ. The apical and basolateral membrane potentials ($V_A$ and $V_B$) are calculated as the voltage differences between the intracellular microelectrode and the apical and basal bath electrodes, respectively. The resistances of the apical and basolateral membranes were designated $R_A$ and $R_B$, respectively, and the transepithelial potential (TEP=$V_B$-$V_A$) is the voltage difference between the apical and basal bath electrodes. Epithelial resistance parameters were obtained by passing 4-μA bipolar current pulses (i) using Ag—AgCl electrodes, one located in the apical chamber and the other located in the basal chamber. The total transepithelial resistance ($R_t$) is calculated from the current-induced changes in TEP ($R_t$=ΔTEP/i). The apparent membrane resistance ratio ($R_A/R_B$) is calculated from the ratio of change in $V_A$ to change in $V_B$ ($R_A/R_B$=$\Delta V_A/\Delta V_B$).

The control Ringer's solution for measurements of TEP and $R_t$ in culture hfRPE contained 116 mM NaCl, 5 mM KCl, 26.2 mM $NaHCO_3$, 1 mM $NaH_2PO_4$, 1 mM Mg $Cl_2$, 1.8 mM $CaCl_2$, 10 mM glucose, and 2 mM Taurine. The osmolarity of control Ringer's solution was 295 mOsm. The solutions were maintained at 35° C. and a pH of 7.4, and were bubbled with 10% $O_2$, 5% $CO_2$ and 85% $N_2$. 8-Bromo-cAMP (or Dibutyryl cAMP), 8-Br-cGMP, and forskolin were obtained from Sigma-Aldrich.

Example 11

In Vivo Retinal Re-Attachment Assay

All animal experiments were conducted in compliance with the ARVO Statement for the use of Animals in Ophthalmic and Vision Research, and the protocol was approved by the Animal Care and Use Committee of the National Institutes of Health. The procedures have been described in detail in Maminishkis, A., et al., *Invest Ophthalmol Vis Sci*, 2006, 47, 3612-3624, incorporated by reference in its entirety herein. Briefly, retinal detachments were created in long-Evans rats by injecting 0.5 to 3 μl of modified phosphate-buffered saline (MPBS) Ringer's solution into the sub-retinal space (SRS), which separates the photoreceptor outer segments and the apical membrane of the RPE. In the control portion of each experiment (at 0-70 minutes after creation of the retinal detachment), the rate of change of bleb volume was measured. The control period of "constant" volume was defined by $J_v \leq 2$ μlhr cm over at least 40 minutes. Any control injections that exceeded this threshold rate were rejected from subsequent analysis.

IFNγ was dissolved in MPBS, mixed with Celluvisc® solution (1:1) and applied as eye-drops (0.4 mL). Optical coherence tomography (OCT) imaging (Institute of Applied Physics, Russian Academy of Science, Nizhniy Novgorod, Russia) was used to measure the time course of the detachment volume change.

Example 12

Statistical Analysis

Data are expressed as mean±s.e.m.; statistical significance (Student's t test, two-tailed) was accepted at $P<0.05$.

Example 13

Expression and Localization of IFNγR in Human RPE

Cells were cultured as described in Example 1 and immunoblotting was performed, as described in Example 3. IFNγ receptor R1 subunit (IFNGR1) is expressed in hfRPE and adult tissue as shown in FIG. 1A. Prominent antibody-specific bands at 65 kDa indicate the presence of the R1 subunit of IFNγ receptor (IFNGR1) in hfRPE, adult RPE, and hfCHC (human fetal choroidal) cells (FIG. 1A). Antibody specific bands for the R2 subunit of the receptor (IFNGR2) at approximately 50 kDa indicate lower expression levels of IFNGR2 in native adult RPE and hfCHC cells relative to IFNGR2 expression in hfRPE cells (FIG. 1A).

Figure 1B:
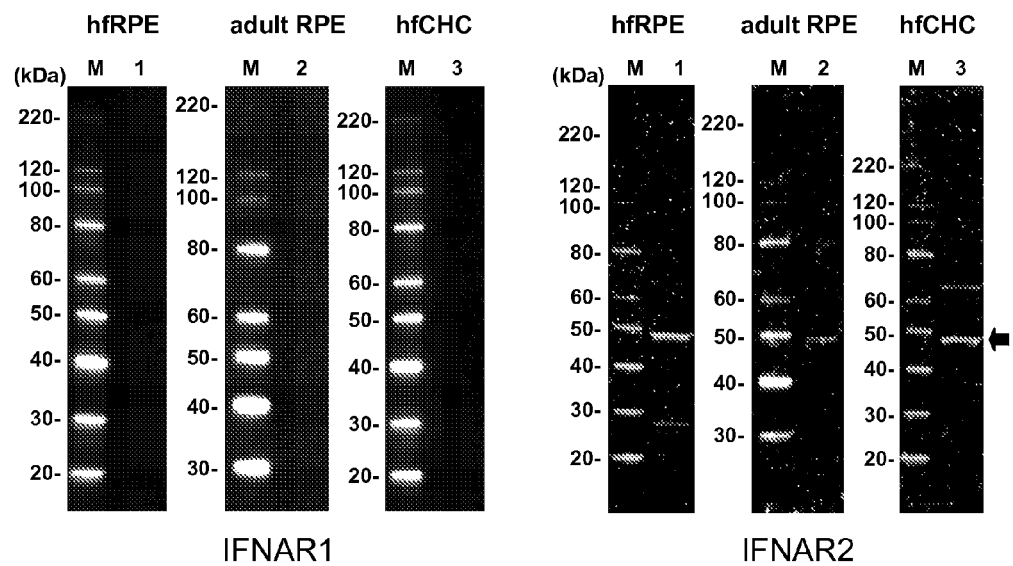
FIG. 1B is an image of several immunoblots depicting the expression of IFNAR1 and IFNAR2 in primary hfRPE cultures (hfRPE; 1), native human adult RPE cultures (2), and primary human fetal choroidal cultures (hfCHC; 3), with a protein marker reference (M).
Figure 1C:
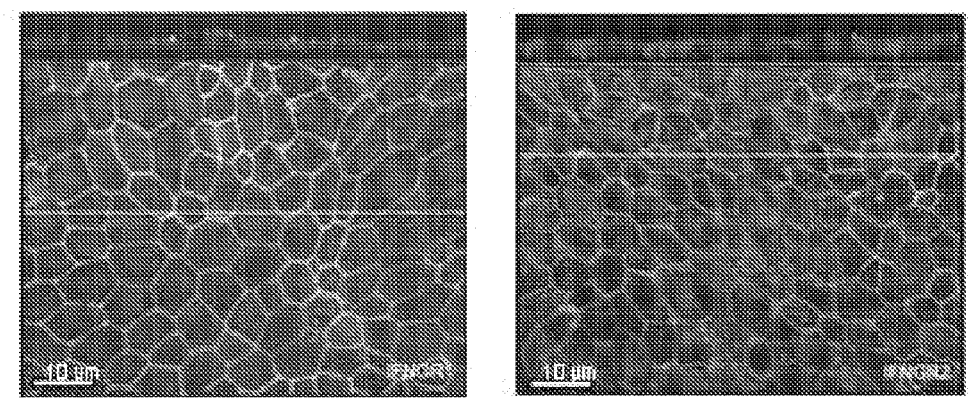
FIG. 1C is a confocal microscopy image depicting the localization of IFNGR1 (left panel) and IFNGR2 (right panel) on the basolateral membrane in hfRPE cells using immunofluorescence staining. Nuclei were stained with DAPI (blue) and ZO-1 was stained as a tight junction marker (green). In both panels, the middle panel is an enface view of the apical membrane shown as the maximum intensity projection through the Z-axis. The top panel is the cross-section through the Z-plane of multiple optical slices.

Localization of the two subunits of the IFNγ receptor in hfRPE cells was determined by immunofluorescence and confocal microscopy, as described in Example 4 (FIG. 1C). Each panel shows one of the Z-sections located on the top side of each main panel. DAPI was used to label the nuclei, and the ZO-1 was labeled (green) as a tight junction marker. IFNGR1 (red, left panel) was located mainly under the ZO-1 (green), indicating a mostly basolateral location with some staining on the apical membrane, while IFNGR2 (right panel) is more evenly distributed on both the apical and basolateral membrane (FIG. 1C).

Example 14

Activation and Regulation of the JAK-STAT Pathway in hfRPE

IFNγ activates the canonical JAK-STAT pathway in many cell types, as described in Darnell, J. E., Jr., et al., *J Interferon Cytokine Res*, 1998, 18, 549-554; Aaronson, D. S., et al., *Science*, 2002, 296, 1653-1655; Maher, S. G., et al., *Curr Med Chem*, 2007, 14, 1279-1289; and van Boxel-Dezaire, A. H., et al., *Curr Top Microbiol Immunol*, 2007, 316, 119-154, each incorporated herein by reference in its entirety. Therefore, the JAK-STAT pathway was analyzed in hfRPE using immunoblotting following treatment of cells with IFNγ, generation of cell lysates, and resolution of protein by gel electrophoresis using the methods described in Examples 1 and 3. For each sample, 20 μg of total protein was used.

Figure 2:
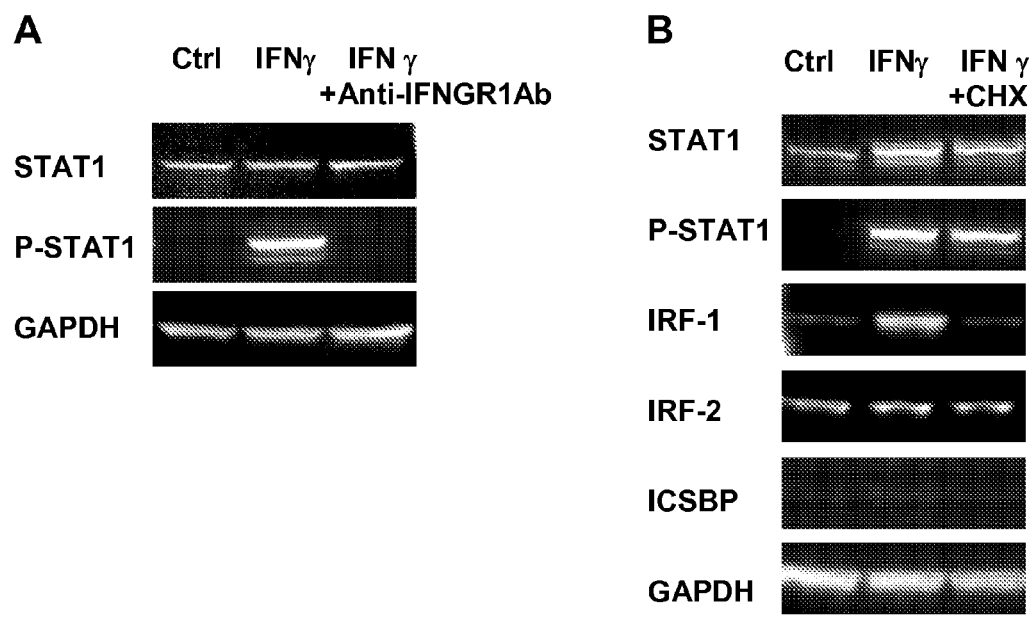
FIG. 2A is an image of several immunoblots depicting the expression of tyrosine-phosphorylated STAT1 (P-STAT1, middle immunoblot), total STAT1 (top immunoblot), and a GAPDH control (bottom immunoblot) in hfRPE cells after 15 minutes of IFNγ treatment. Cultured hfRPE cells were incubated with SFM (Ctrl, lane 1), SFM containing IFNγ (lane 2), or cells were treated with anti-IFNGR1 blocking antibodies for 30 minutes, and then incubated with SFM containing IFNγ (IFNγ+Anti-IFNGR1Ab, lane 3). 10 μg of total protein was loaded and subject to electrophoresis.
FIG. 2B is an image of immunoblots depicting the expression of (in order from top to bottom) total STAT1, tyrosine-phosphorylated STAT1 (P-STAT1), interferon regulated factor 1 (IRF-1), interferon regulated factor 2 (IRF-2), and interferon regulated factor 8 (ICSBP/IRF-8), in hfRPE cells after 15 minutes of IFNγ treatment. GAPDH is shown as a control for protein loading. Cells were treated with SFM (Ctrl, lane 1), SFM containing IFNγ (lane 2), or with CHX (a protein synthesis inhibitor) and IFNγ (IFNγ+CHX, lane 3) for 4 hours. 10 μg of total protein was loaded and subject to electrophoresis.

STAT1 was tyrosine phosphorylated after addition of IFNγ (5 ng/ml) for 15 minutes (FIG. 2A). This response was blocked by pre-treatment for 30 minutes with anti-IFNγ R1 monoclonal antibody (FIG. 2A). Prolonged treatment with IFNγ for 4 hours phosphorylated STAT1 (double band) and activated the nuclear transcription factor IRF-1 (FIG. 2B). IRF-2 was constitutively expressed and unaffected by IFNγ (FIG. 2B), while IRF-8 (ICSBP) was below the detection limit. Protein synthesis inhibition by CHX (62 μM; 4 hours) had no effect on IRF-2, but completely blocked the de novo synthesis of IRF-1. (FIG. 2B). The STAT1 protein signal significantly increased after IFNγ treatment and STAT1 synthesis was partly inhibited by cycloheximide as shown in the top panel of FIG. 2B. Similar protein expression levels of STAT1, IRF-1, IRF-2, and IRF-8 in the absence of IFNγ were also observed in native adult RPE cells (data not shown).

Experiments utilizing quantitative real-time PCR revealed that transcription of IRF-1 and STAT1 was significantly up-regulated (>400, >30 fold, respectively) by 25 ng/ml IFNγ treatment of hfRPE, confirming the immunoblotting results above. IRF-2 mRNA was also upregulated, however the fold change(≈3) was less than that of IRF-1. (Table 1, below). The constitutive expression level of IRF-8 mRNA was under the detection level, but became detectable after 2 hours of treatment with IFNγ, while no detectable change was detected in IRF-8 protein levels (Table 1).

Thus, native human adult RPE and hfRPE cells constitutively express IRF-1 and IRF-2, but not ICSBP. The constitutive level of IRF-2 protein is much higher than that of IRF-1 but stimulation by IFNγ significantly increased IRF-1 protein levels with no effect on IRF-2 despite a 3-fold increase in IRF-2 mRNA. These two transcription factors are known in the art to be mutually antagonisti, which may explain the strong inhibitory effect of IFNγ on RPE proliferation and migration caused perhaps by an increase in the ratio of IRF-1/IRF-2.

As in previous studies in cystic fibrosis epithelia, as described in Kelley T J, et al., *J Clin Invest* 106: 403-410, 2000., hereby incorporated by reference in it entirety, the effect of IFNγ treatment on the mRNA levels of SOCS3 (suppressor of cytokine signaling 3), NOS2A (inducible nitric oxide synthase), CFTR, IFNGR1, IFNGR2, and PIAS1 (STAT1) in hfRPE cells was also determined using quantitative real-time PCR, using the method described in Example 2 (Table 1). SOCS3 levels increased. NOS2A expression was significantly up-regulated after 6 hours of treatment with IFNγ, whereas constitutive levels were undetectable. There was an increase in IFNGR2 expression (≈2 fold) observed after 6 hours of treatment. No effect of IFN γ treatment on PIAS1, CFTR (constitutively low expression levels), or IFNGR1 expression was observed (Table 1).

While cytokine responses are typically transient; several inhibitory mechanisms have been identified that down regulate STAT signaling. For example, SOCS is a family of cytokine-inducible proteins that function to regulate the initiation, intensity, and duration of JAK-STAT signaling. PIAS (protein inhibitor of activated STAT) is a member of another family of proteins that can inhibit the transcriptional activity of STAT. As described above, in hfRPE, IFNγ significantly up-regulated STAT1 protein levels, as observed in other systems. In contrast to most other systems, however, the IFNγ-induced phosphorylation of STAT1 was observed over a much longer period of time (2 to 48 hrs). Stimulation with IFNγ does not affect PIAS1, but does increase SOCS3 mRNA by 7-fold. These results suggest the absence of a negative feedback mechanism, which may indicate a difference between fetal cultures and native cells. This may illustrate a particular function of IFNγ, which provides a sustained increase of fluid transport out of the subretinal space in the inflammatory state.

TABLE 1

IFNγ-induced alterations in gene expression by quantitative real time PCR

| Gene | Threshold Cycle (Ct) | | | | | |
|---|---|---|---|---|---|---|
| | 0 | 0.5 | 2 | 6 | 15 | 24 (hr) |
| STAT1 | 26.2 | 25.8 | 22.1 | 21.0 | 21.3 | 21.2 |
| IRF-1 | 31.1 | 27.4 | 22.2 | 22.3 | 22.3 | 22.2 |
| IRF-2 | 27.6 | 27.6 | 26.0 | 25.6 | 26.0 | 26.1 |
| IRF-8 | — | — | 30.9 | 31.1 | 32.0 | 31.9 |
| IFNGR1 | 26.4 | 26.4 | 26.4 | 26.3 | 26.5 | 26.3 |
| IFNGR2 | 26.0 | 26.0 | 25.1 | 24.7 | 25.1 | 25.2 |
| SOCS3 | 26.9 | 25.4 | 24.6 | 24.0 | 24.8 | 24.9 |
| PIAS1 | 27.0 | 26.9 | 27.2 | 27.1 | 26.8 | 26.7 |
| NOS2A | — | 39.1 | 35.9 | 31.6 | 32.7 | 33.5 |
| CFTR | 38.0 | 36.9 | 37.3 | 38.5 | — | 37.9 |

— undetermined

Example 15

IFNγ Decreased the Mitochondrial Membrane Potential in hfRPE

Figure 3:
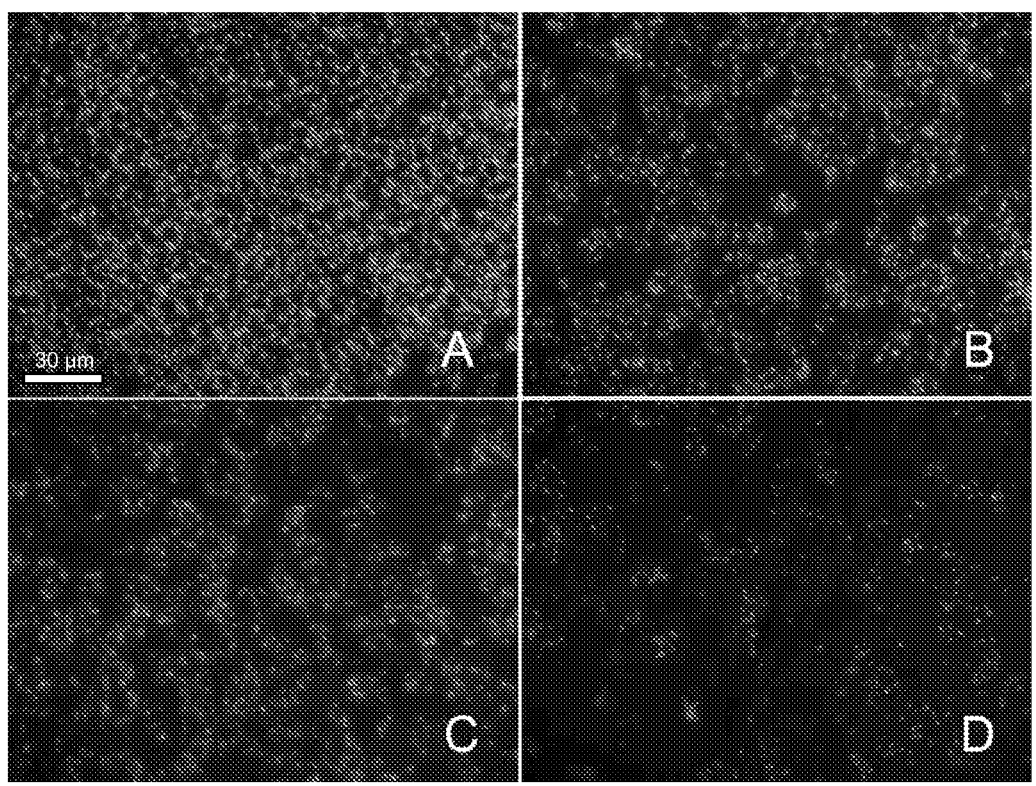
FIG. 3 is confocal microscopy images, generated using a Zeiss Axiovert 25 inverted microscope, of JC-1 immunofluorescence staining of mitochondria in RPE cells.

JC-1 staining of mitochondria was performed as described in Example 5 to evaluate the effects of IFNγ on the mitochondrial membrane potential in confluent hfRPE monolayers. A dose-dependent decrease in the mitochondrial membrane potential was observed following IFNγ treatment (0.5, 5, 50 ng/ml; 72 hours) of confluent hfRPE monolayers, as shown by the monotonic decrease in red JC-1 aggregate fluorescence compared to control ((untreated control, FIG. 3A; 0.5 ng/ml, FIG. 3B; 5 ng/ml, FIG. 3C; 50 ng/ml, FIG. 3D)). Data represent duplicate experiments, with each treatment completed in triplicate in each experiment. While these effects were observed at 72 hours after treatment with IFNγ, no significant differences were observed at the 24 or 48 hour time points (data not shown).

Example 16

IFNγ Inhibited hfRPE Proliferation and Migration and Inhibited Growth Factor-Induced hfRPE Proliferation Previous results demonstrated the strong inhibitory effect of a pro-inflammatory cytokine mixture ((or "ICM," containing TNFα (10 ng/ml), IL-Nγ (10 ng/ml) and IFNγ (5 ng/ml)) on hfRPE proliferation and migration as described in Li, R., et al., *Invest Ophthalmol Vis Sci*, 2007, 48, 5722-5732, incorporated herein by reference in its entirety.

Figure 4:
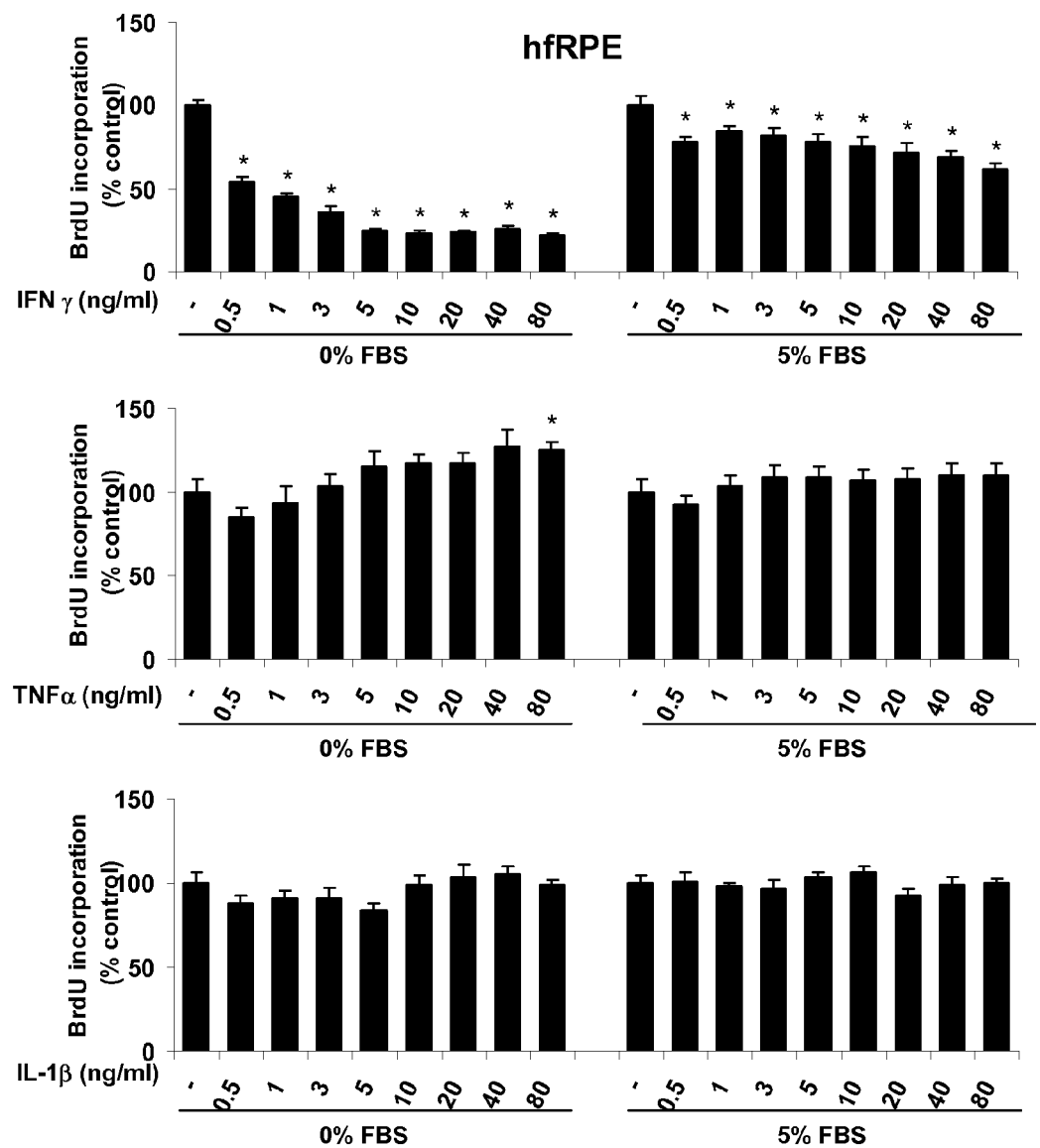
FIG. 4 is a bar graph showing the proliferation of hfRPE cells, in 0% or 5% FBS, in response to treatment with IFNγ (top panel), TNFα (middle panel), or IL-1β (bottom panel) as measured by the percentage of BrdU incorporation relative to untreated control cells. (n=4, * indicates P<0.05)

Therefore, to better understand the effects of individual ICM components on the proliferation response, the effects of these individual components were analyzed using BrdU incorporation as described in Example 6. A summary of the dose-response curves for each of the individual components is shown (FIG. 4).

Cell viability was evaluated in all of these experiments. The percentage of viable cells in these and all subsequent experiments was more than 85%, and cell viability was not significantly reduced after incubation with cytokines or growth factors (data not shown). IL-1β treatment had no significant effect on hfRPE proliferation over the entire range of concentrations (0.5-80 ng/ml) (FIG. 4, bottom panel). TNFα treatment showed a weak stimulatory effect, which did not reach statistical significance until 80 ng/ml ($P<0.05$) (FIG. 4, middle panel). IFNγ, however, showed a strong inhibitory effect over a wide range of concentrations (0.5-80 ng/ml) (FIG. 4, top panel). In other experiments, IFNγ inhibited hfRPE proliferation at concentration as low as 0.02 ng/ml (data not shown).

Figure 5:
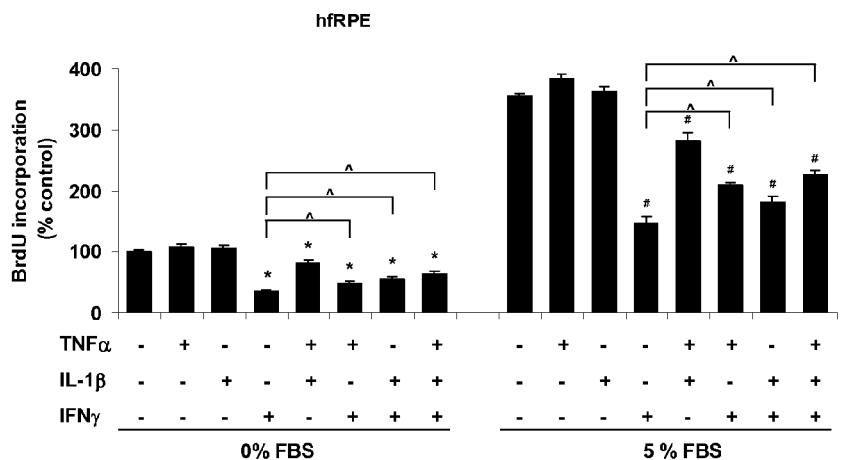
FIG. 5 is a bar graph showing inhibition of the proliferation of hfRPE cells, in 0% or 5% FBS, in response to treatment with IFNγ, TNFα, or IL-1β, or combinations thereof, as measured by the percentage of BrdU incorporation relative to untreated control cells. (* indicates P<0.05 as compared to 0% FBS control; # indicates P<0.05 as compared to 5% FBS control; ^ indicates P<0.05 for IFNγ treatment as compared to IFNγ plus TNFα or IL-1β; (n=4)).
Figure 7:
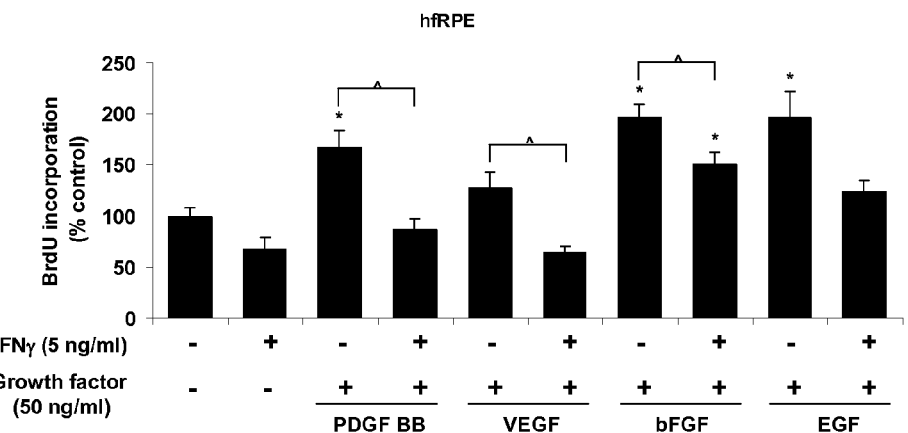
FIG. 7 is a bar graph showing inhibition of the proliferation of hfRPE cells in response to treatment with IFNγ, the growth factors PDGF-BB, bFGF, VEGF, or combinations thereof, as measured by the percentage of BrdU incorporation relative to untreated control cells. (* indicates P<0.05, as compared to SFM control; ^ indicates P<0.05, for growth factor alone as compared to growth factor plus IFNγ (5 ng/ml).)
Figure 8:
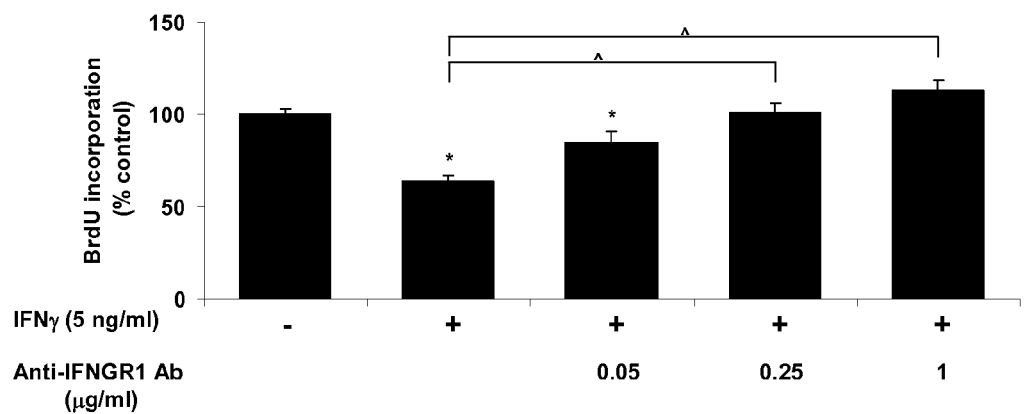
FIG. 8 is a bar graph showing dose-dependent inhibition of the proliferation of hfRPE cells in response to treatment with IFNγ, or IFNγ and various concentrations of anti-IFNγ R1 blocking antibody, as measured by the percentage of BrdU incorporation relative to untreated control cells. (* indicates P<0.05, as compared to SFM control; ^ indicates P<0.05, for the different antibody concentrations plus IFNγ, as compared to IFNγ alone (n=4).)
Figure 9:
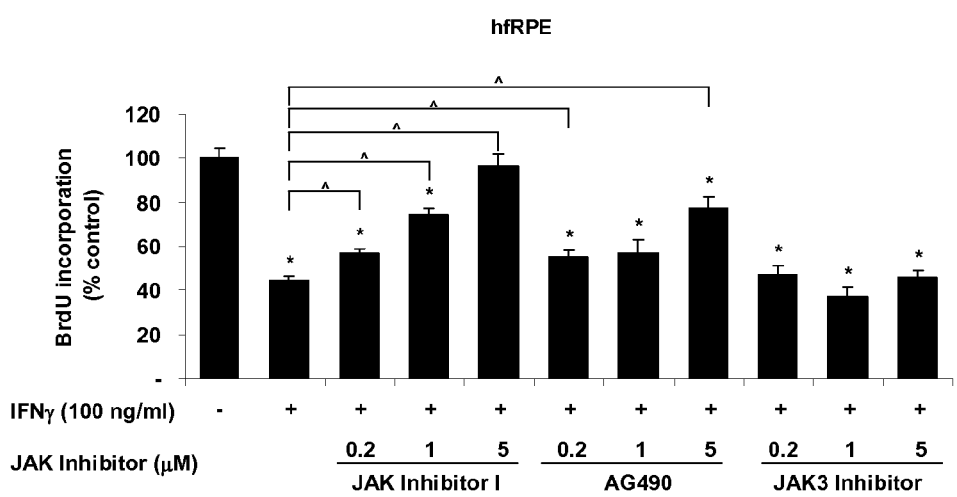
FIG. 9 is a bar graph showing inhibition of the proliferation of hfRPE cells in response to treatment with IFNγ, or IFNγ and various concentrations of JAK inhibitors ((JAK inhibitor I, AG490 (JAK2 inhibitor), and JAK3 inhibitor)), as measured by the percentage of BrdU incorporation relative to untreated control cells. (* indicates P<0.05, as compared to IFNγ-free (−) media control; ^ indicates P<0.05, showing the effectiveness of different JAK inhibitor concentrations, as compared to IFNγ-induced inhibition in the absence of inhibitor (n=4).)
Figure 10:
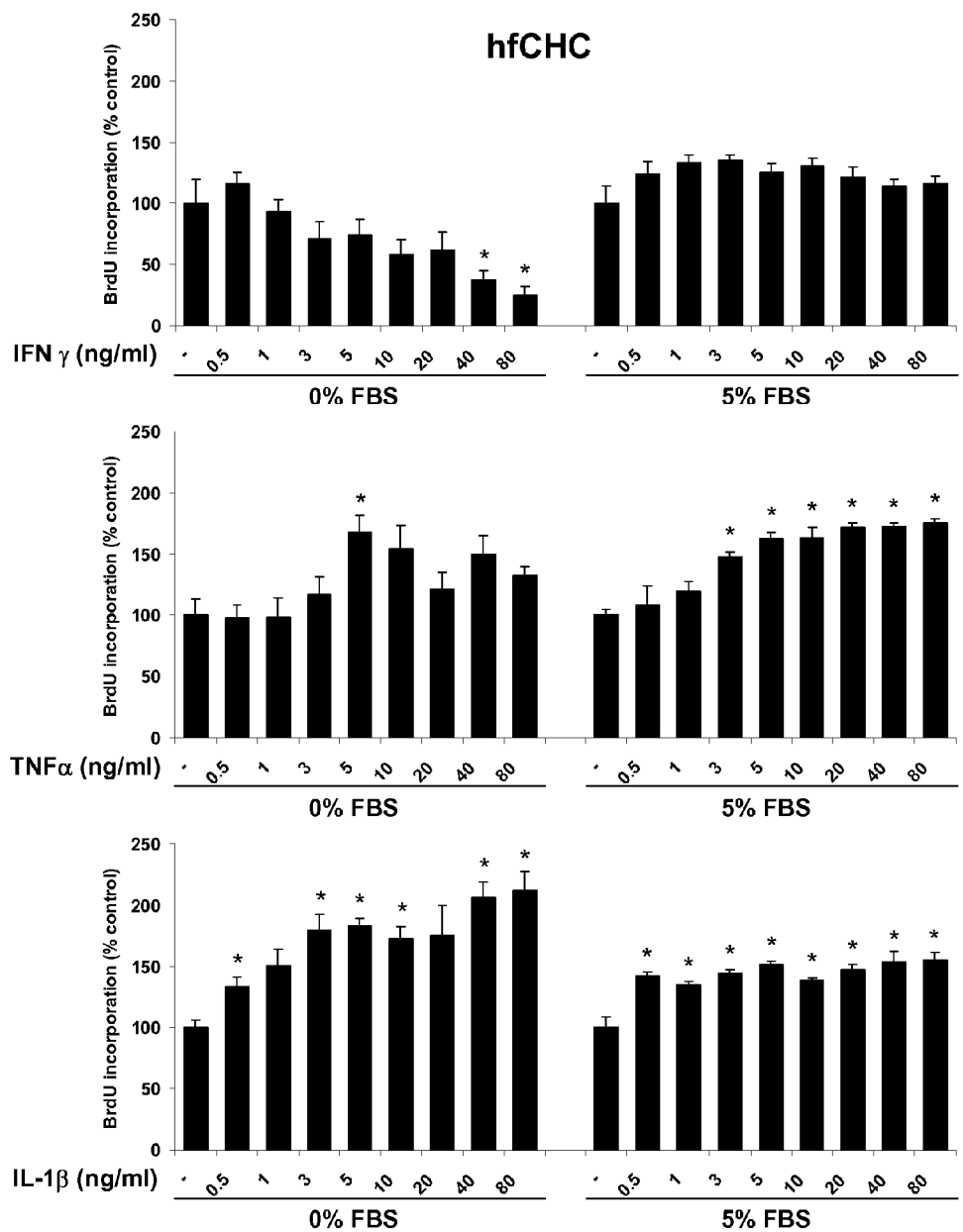
FIG. 10 is a bar graph showing the proliferation of hfCHC cells, in 0% or 5% FBS, in response to treatment with IFNγ (top panel), TNFα (middle panel), or IL-1β (bottom panel) as measured by the percentage of BrdU incorporation relative to untreated control cells. (* indicates P<0.05, for cytokine-induced proliferation as compared to cytokine-free (−) media control (n=4).) The results demonstrate at least that TNFα and IL-1β significantly stimulated hfCHC cell proliferation over a wide concentration.
Figure 11:
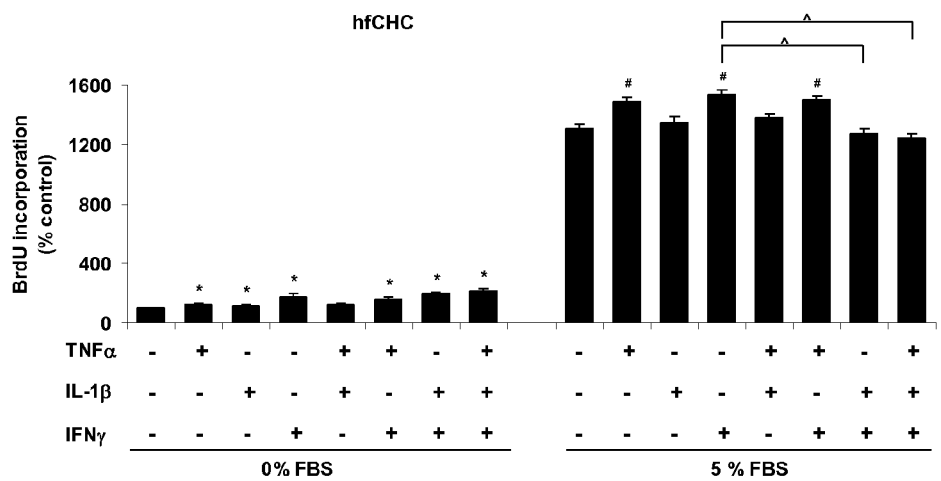
FIG. 11 is a bar graph showing the proliferation of hfCHC cells, in 0% or 5% FBS, in response to treatment with IFNγ, TNFα, or IL-1β, or combinations thereof, as measured by the percentage of BrdU incorporation relative to untreated control cells. (* indicates P<0.05, for the combinations of cytokines as compared to control in 0% FBS; # indicates P<0.05, for the combinations of cytokines as compared to control in 5% FBS; ^ indicates P<0.05, for the comparison of IFNγ alone to IFNγ plus TNFα and/or IL-1β (n=4).)
Figure 12:
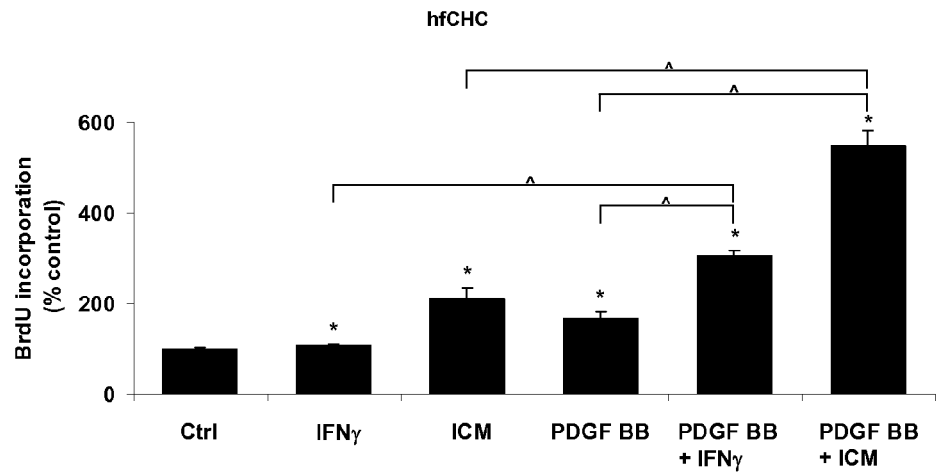
FIG. 12 is a bar graph showing the proliferation of hfCHC cells in response to treatment with IFNγ, ICM, PDGF-BB, and simultaneous treatment of PDGF-BB with either IFNγ (PDGF BB+IFNγ) or ICM (PDGF BB+ICM), as measured by the percentage of BrdU incorporation relative to untreated control cells. (* indicates P<0.05 for treatments relative to SFM control; ^ indicates P<0.05, for comparison of PDGF-BB plus IFNγ or ICM with single components (n=4).)

Combinations of various ICM components were also analyzed for their ability to inhibit hfRPE proliferation. As in the experiments just described, only treatment with IFNγ alone (5 ng/ml) significantly inhibited hfRPE cell proliferation in 5% FBS or 0% FBS (n=4, $P<0.001$)) (FIG. 5). Furthermore, IFNγ significantly inhibited hfRPE proliferation induced by bFGF, PDGF-BB, VEGF (FIG. 7). Pretreatment with anti-human IFNGR1 blocking antibodies abolished the inhibitory effect of IFNγ on hfRPE proliferation (FIG. 8) indicating the specificity of this effect for IFNγ. FIG. 9 shows that JAK inhibitor I, a universal JAK inhibitor and AG490 (JAK 2 inhibitor), but not JAK3 block the IFNγ-induced hfRPE proliferation in a dose dependent manner. Similar experiments were performed using cells from human fetal choroidal tissues. In striking contrast to the effect observed in hfRPE, IFNγ alone, or in combination with TNFα or IL-1β, showed a stimulatory effect on human fetal choroidal cell proliferation (FIGS. 10 and 11). IFNα and β (type I IFN) have no effect on hfRPE proliferation (data not shown). This conclusion was corroborated by immunoblotting analysis which shows that the R1 subunit of type I IFN (IFNAR1) is undetectable in human RPE, although the R2 subunit (IFNAR2) is expressed at intermediate levels (FIG. 1B).

Figure 6:
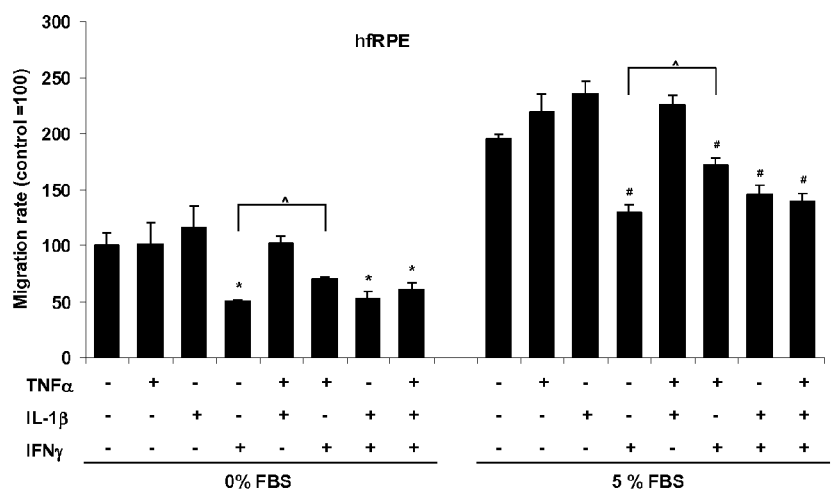
FIG. 6 is a bar graph showing the normalized migration rate of hfRPE cells, in 0% or 5% FBS, in response to treatment with IFNγ, TNFα, or IL-1β, or combinations thereof, as measured by a wound healing assay in which cell proliferation was suppressed, a 7 mm area of the culture dish was denuded, and the average number of cells that migrated into the denuded area after the various treatments was counted. (* indicates P<0.05 as compared to 0% FBS control; # indicates P<0.05 as compared to 5% FBS control; ^ indicates P<0.05 for IFNγ treatment as compared to IFNγ plus TNFα or IL-1β; (n=3)).

Combinations of various ICM components were also analyzed for their ability to inhibit hfRPE migration using the wound healing assay as described in Example 7 (FIG. 6). IFNγ treatment significantly inhibited hfRPE cell migration, whereas treatment with TNFα and IL-1β had no significant effect. ICM treatment, and treatment with combinations of TNFα or IL-1β with IFNγ, showed a significant inhibitory effect on cell migration.

Example 17

Expression and Localization of CFTR in Human RPE

It has been shown that CFTR is an important determinant of human RPE active ion-coupled fluid transport and that the ICM increases fluid absorption across hfRPE, as described in Blaug, S., et al., *Doc Ophthalmol* 2003, 106, 43-50; Quinn, R. H., et al., *Invest Ophthalmol Vis Sci*, 2001, 42, 255-264; and Shi, G., et al., *Invest Ophthalmol Vis Sci,* 2008 April 30, each incorporated herein by reference in its entirety.

Figure 13:
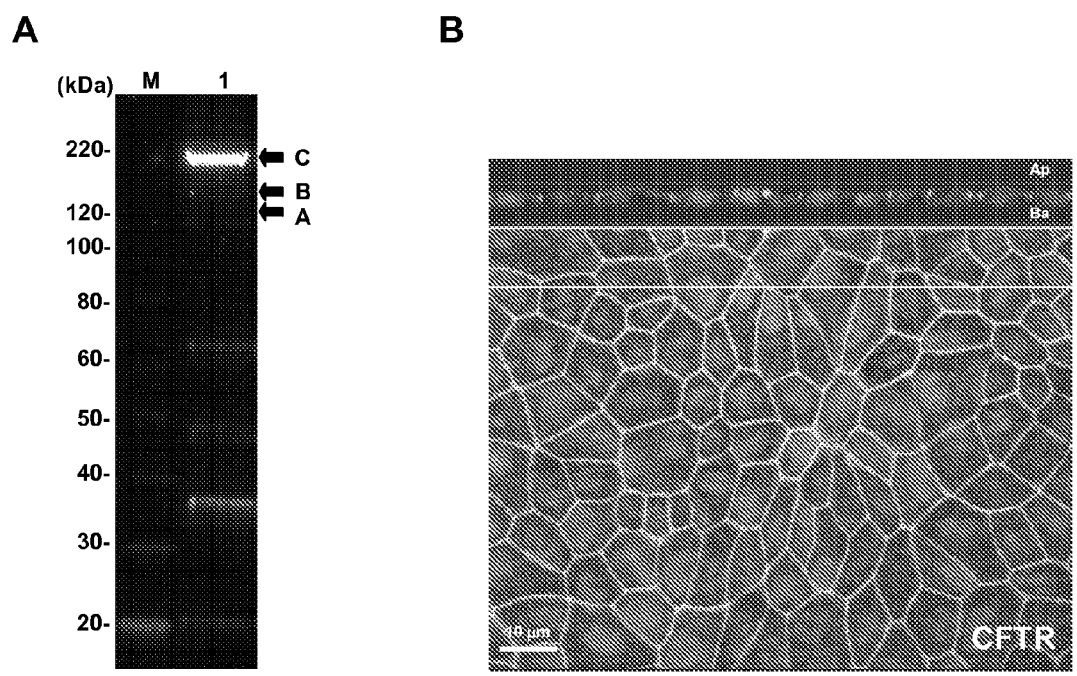
FIG. 13A is an image of an immunoblot depicting the expression of CFTR in membrane enriched extracts from primary hfRPE cells (1). Positions of molecular weight standards (M) and the positions of major mature (C) and immature (B and A) bands of CFTR are indicated.
FIG. 13B is an immunofluorescence image depicting the localization of CFTR on hfRPE cells. Nuclei of the cells were stained with DAPI (blue) and ZO-1 was stained red as a tight junction marker. The x-y plane is shown in the main panel as an enface view of the apical membrane (maximum intensity projection through the Z-axis). The uppermost view is the cross-section through the Z-plane of multiple optical slices showing that CFTR is mostly located below ZO-1 on the basolateral membrane.

Therefore, the possible role of IFNγ in the activation of CFTR was analyzed using immunoblotting as described in Example 3 and the above references. The presence of CFTR in hfRPE cells was confirmed, as indicated by the prominent antibody-specific bands at 190 kDa in the samples of hfRPE membrane extract (FIG. 13A). Immunofluorescence localization experiments, performed according to the methods described in Example 4, showed that the CFTR protein was mostly localized at the basolateral membrane of a confluent monolayer of hfRPE cells grown on a transwell insert (FIG. 13B). All of these data taken together indicate a fundamentally important role for CFTR in mediating fluid transport across human RPE.

In addition, cytokine regulation of CFTR is known in the art to be complex and cell specific. For example, it has been shown that IFNγ modulation of CFTR gene expression is mediated by both STAT1-dependent and independent pathways, as described in Kulka, M., et al., *J. Pharmacol Exp Ther,* 315, 563-570, herein incorporated by reference in its entirety. In T84 cells, the IFNγ-mediated down-regulation of CFTR was inhibited by a JAK2 inhibitor, but not by P38 or ERK inhibitors. In contrast, in rat and human mast cells IFNγ up-regulation of CFTR is P38 and ERK-dependent and JAK2-independent. Here, as described above, IFNγ caused a small decrease in both CFTR mRNA and protein level, but this change is not statistically significant. This small reduction may be attributed to the balance between CFTR degradation in the cell and recycling to the plasma membrane.

Example 18

IFNγ Increases Fluid Transport Across the RPE

Figure 14A:
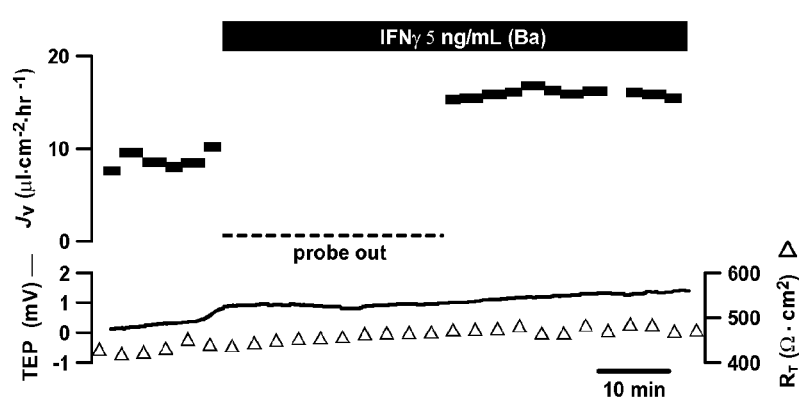
FIG. 14A depicts two traces: the top trace shows a net increase in steady-state fluid absorption from the retinal to the choroidal side (apical to basal bath) in hfRPE cultures after the addition of 5 ng/mL of IFNγ to the basal bath, as a plot of $J_V$ (μl·cm$^{-2}$·hr$^{-1}$, ■) as a function of time; TEP (mV, −) and $R_T$(Ω·cm$^2$, Δ) are plotted as functions of time in the lower traces. (n=10, P<0.01)

Fluid transport assays were performed as described in Example 9 to examine whether IFNγ induced changes in fluid transport across hfRPE monolayers. IFNγ did increase fluid transport: IFNγ (5 ng/ml in the basal bath) increased $J_V$ by ~8.6 $\mu l \cdot cm^{-2} \cdot hr^{-1}$, reflecting an increase in steady-state fluid absorption from the retinal to the choroidal side of the tissue (FIG. 14A). There were no apparent changes in cell viability as measured by transepithelial potential (TEP) and total tissue resistance ($R_T$). In 10 experiments, the mean $J_V$ increased from 12.9±1.6 to 20.5±3.1 $\mu l \cdot cm^{-2} \cdot hr^{-1}$ (mean±s.e.m., P<0.01). Rapid changes in TEP or $R_T$ were not recorded.

Figure 14B:
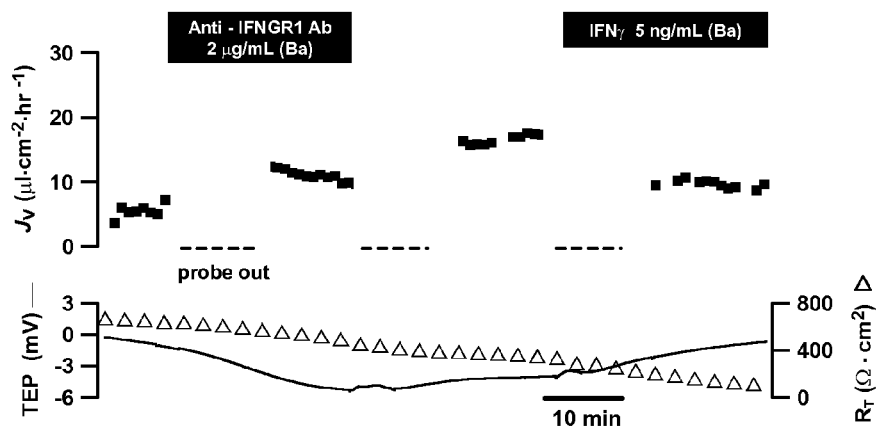
FIG. 14B depicts two traces: the top trace shows the net fluid absorption (apical to basal bath) in hfRPE cultures after the addition of 5 ng/mL of IFNγ to the basal bath following pre-treatment with 2 μg/mL of anti-IFNGR1 blocking antibody for 30 minutes, as a plot of $J_V$ (μl·cm$^{-2}$·hr$^{-1}$, ■) as a function of time. TEP (mV, −) and $R_T$(Ω·cm$^2$, Δ) are plotted as functions of time in the lower traces. In the presence of blocking antibody, no significant changes in $J_V$ were observed. (n=9).
Figure 14C:
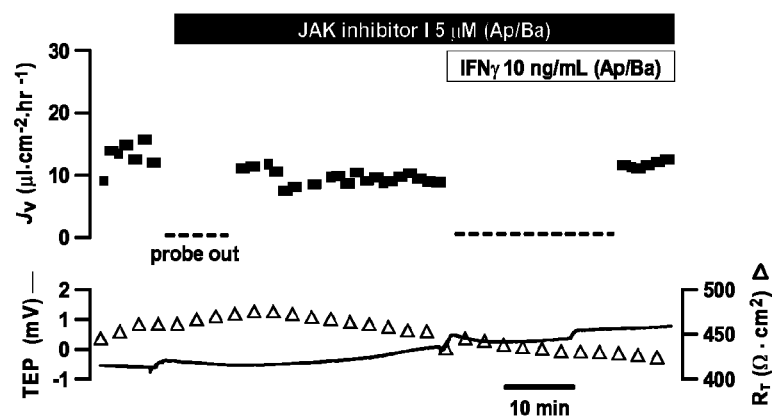
FIG. 14C depicts two traces: the top trace shows the net fluid absorption (apical to basal bath) in hfRPE cultures after the addition of 10 ng/mL IFNγ to the apical and basal baths following pre-treatment with JAK inhibitor I (5 μM) for 30 minutes, as a plot of $J_V$(μl·cm$^{-2}$·hr$^{-1}$, ■) as a function of time; the bottom trace shows the plots of TEP (mV, −) and $R_T$(Ω·cm$^2$, Δ) as functions of time. The results indicate that the JAK inhibitor I alone had no significant effect on the baseline $J_V$, but it significantly blocked the IFNγ-induced increase in $J_V$ (n=3).

In contrast, addition of IFNγ to the apical bath had no significant effect on $J_V$, consistent with the localization experiments described above in Example 13 (FIG. 1C). In another set of experiments, Ringer's solution containing anti-IFNγR1 blocking antibody (2 μg/ml) was used to perfuse an intact monolayer of hfRPE for 30 minutes prior to the addition of IFNγ (10 ng/ml) to the basal bath (FIG. 14B). In the presence of blocking antibody, no significant $J_V$ changes were observed (n=9) (FIG. 14B). Further, in another set of experiments, JAK inhibitor I (5 μM) was added about 0.5-1 hours prior to the addition of IFNγ (FIG. 14C). JAK inhibitor I alone had no significant effect on the base level of fluid transport, however it did significantly block the IFNγ increase in $J_V$ across hfRPE. Similar results were observed in an additional two experiments.

Figure 14D:
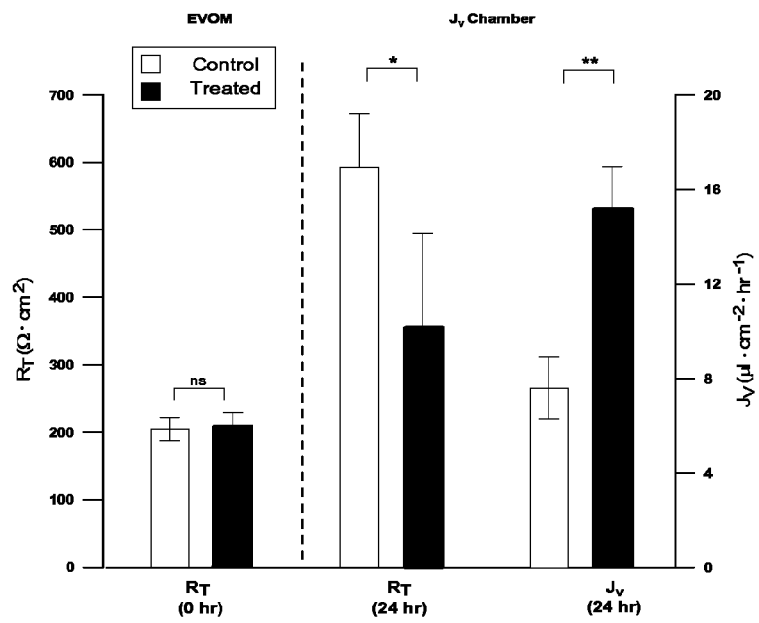
FIG. 14D is the summary data of $J_V$, and $R_T$ after 24 hour IFNγ treatment. Paired hfRPE cultures were untreated or treated with 5 ng/mL IFNγ in the apical and basal baths; tissue were mounted in a modified Üssing chamber and $J_V$, TEP and $R_T$ recorded. A statistically significant increase in $J_V$ and decrease in $R_T$ were observed in 24 hour IFNγ-treated filters versus control (*P<0.05, ** P<0.01). ns, non-significant.

Fluid transport in hfRPE was also measured following chronic exposure to IFNγ (FIG. 14D). Pairs of hfRPE inserts with matching $R_T$ levels were incubated with IFNγ (5 ng/ml) in both the apical and basal baths, or were left in control media, for 24 hours. Fluid transport and electrical parameters were then measured in each pair. In 5 experiments, the mean $J_V$ in the control monolayers was 7.6±1.5 $\mu l \cdot cm^{-2} \cdot hr^{-1}$ and IFNγ treatment increased $J_V$ to 15.2±2.0 $\mu l \cdot cm^{-2} \cdot hr^{-1}$ (mean±SEM, P<0.01). There were no significant TEP changes for these experiments (FIG. 14D). However there was a significant IFNγ-induced decrease in $R_T$ from 592±80 to 356±139 $\Omega \cdot cm^2$ (n=5; p<0.05); at t=0, the pairs had no significant difference in $R_T$ (205±17 compared with 210±20 $\Omega \cdot cm^2$, n=5, P=0.86).

Figure 14E:
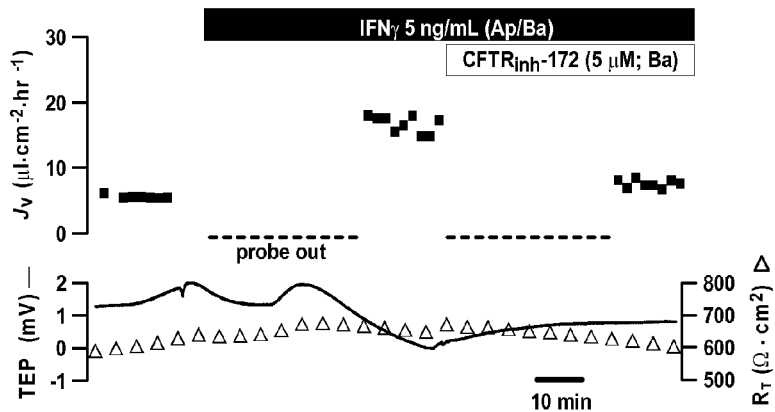
FIG. 14E depicts two traces: the top trace shows the net fluid absorption (apical to basal bath) in hfRPE cultures after the addition of 5 ng/mL IFNγ to the apical/basal bath and subsequent addition of CFTR inhibitor (5 μM) to the basal bath, as a plot of $J_V$ (μl·cm$^{-2}$·hr$^{-1}$, ■) as a function of time; TEP (mV, −) and $R_T$(Ω·cm$^2$, Δ) are plotted as functions of time in the lower traces. The results demonstrate that the inhibitor reversibly decreased $J_V$. (n=11; P<0.001)
Figure 14F:
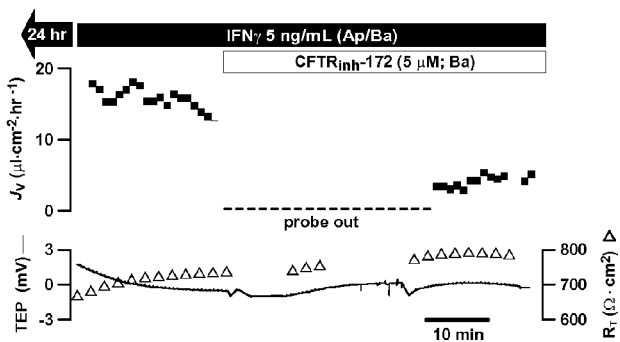
FIG. 14F depicts two traces: the top trace shows the net fluid absorption (apical to basal bath) in paired hfRPE cultures after 24 hour treatment with 5 ng/mL IFNγ in the apical and basal baths, mounting in a modified Üssing chamber, and subsequent addition of a CFTR inhibitor (5 μM) to the basal bath, as a plot of $J_V$(μl·cm$^{-2}$·hr$^{-1}$, ■) as a function of time; the bottom trace shows the plots of TEP (mV, −) and $R_T$(Ω·cm$^2$, Δ) as functions of time. The results demonstrate that the inhibitor reversibly decreased $J_V$. (n=2).

Basal bath addition of a specific CFTR inhibitor (CFTR$_{inh}$-172; 5 μM) decreased the IFNγ-induced $J_V$ increase by ≈9.8 $\mu l \cdot cm^{-2} \cdot hr^{-1}$ (FIG. 14E). In 11 experiments, this inhibitor reversibly decreased mean $J_V$ from 16.6±1.2 to 6.8±1.0 $\mu l \cdot cm^{-2} \cdot hr^{-1}$ (P<0.001). A similar inhibitory effect of CFTR$_{inh}$-172 was also observed in two experiments in which RPE cells were incubated with IFNγ, in both the apical and basal media, for 24 hours (FIG. 14F). After addition of CFTR$_{inh}$-172 (5 μM), $J_V$ decreased from 15.1 $\mu l \cdot cm^{-2} \cdot hr^{-1}$ to 4.8 $\mu l \cdot cm^{-2} \cdot hr^{-1}$ (FIG. 14F).

In another set of experiments, the baseline of $J_V$ (12.5±3.1 $\mu l \cdot cm^{-2} \cdot hr^{-1}$) was also significantly inhibited by basal bath addition of CFTR$_{inh}$-172 (3.2±1.0 $\mu l \cdot cm^{-2} \cdot hr^{-1}$) (n=5, P=0.01). DIDS (500 μM) had no effect on spontaneous steady-state $J_V$ (n=2), and the addition of DIDS following CFTR$_{inh}$-172 inhibition of IFNγ-induced $J_V$ produced no further inhibition of $J_V$ (n=2) (data not shown). Furthermore, the IFNγ-induced $J_V$ increase was not affected by the addition of basal DIDS, but the subsequent addition of CFTR$_{inh}$-172 decreased $J_V$ by 12.6 $\mu l \cdot cm^{-2} \cdot hr^{-1}$ (n=1) (data not shown). These four experiments taken together indicate that the basolateral membrane DIDS sensitive mechanism does not affect IFNγ-induced changes in $J_V$.

Figure 14G:
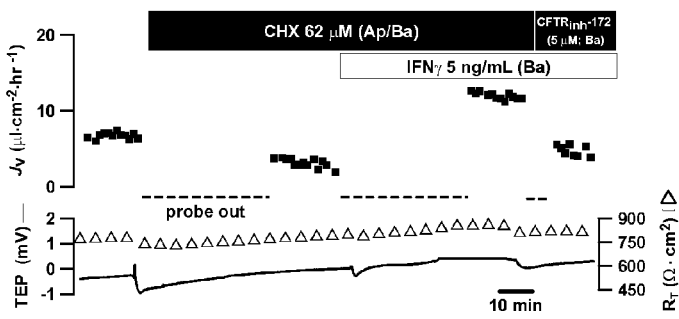
FIG. 14G depicts two traces: the top trace shows the net fluid absorption (apical to basal bath) in hfRPE cultures after perfusion with cyclohexamide (CHX, 62 μM) for 30 minutes in the apical and basal baths, addition of 5 ng/mL IFNγ to the basal bath, and subsequent addition of a CFTR inhibitor to the basal bath, as a plot of $J_V$ (μl·cm$^{-2}$·hr$^{-1}$, ■) as a function of time; the bottom trace shows the plots of TEP (mV, −) and $R_T$(Ω·cm$^2$, Δ) as functions of time. The results demonstrate that for this amount and timing for treatment, CHX per se produced no apparent change in $J_V$, had no effect on the IFNγ induced increase in $J_V$, and did not affect the CFTR inhibitors ability to block the IFNγ induced increase in $J_V$. (n=2).

Whether the IFNγ-induced changes in $J_V$ required de novo protein synthesis was tested using cyclohexamide (CHX), a protein synthesis inhibitor (FIG. 14G). A confluent hfRPE monolayer was perfused with cyclohexamide (62 μM) in both the apical and basal baths for 30 minutes before the addition of IFNγ (5 ng/ml). CHX per se produced no change in $J_V$, and had no effect on the IFNγ-induced increase in $J_V$. Also, CHX did not affect the ability of CFTR$_{inh}$-172 to block the IFNγ-induced $J_V$ increase (FIG. 14G).

Figure 14H:
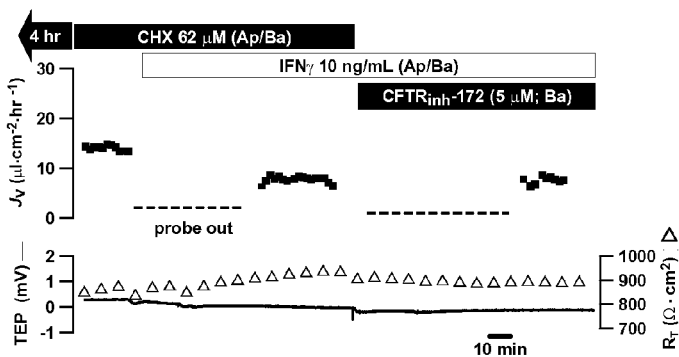
FIG. 14H depicts two traces: the top trace shows the net fluid absorption (apical to basal bath) in hfRPE cultures after pre-treatment with cyclohexamide for 4 hours in the apical and basal baths, addition of 10 ng/mL IFNγ to the apical and basal baths, and subsequent addition of a CFTR inhibitor (5 μM) to the basal baths, as a plot of $J_V$ (μl·cm$^{-2}$·hr$^{-1}$, ■) as a function of time; the bottom trace shows the plots of TEP (mV, −) and $R_T$(Ω·cm$^2$, Δ) as functions of time. The results demonstrate that after 4 hours of treatment with CHX, there was no IFNγ induced increase in $J_V$ and no further effect of the CFTR inhibitor on $J_V$. (n=3).
Figure 14I:
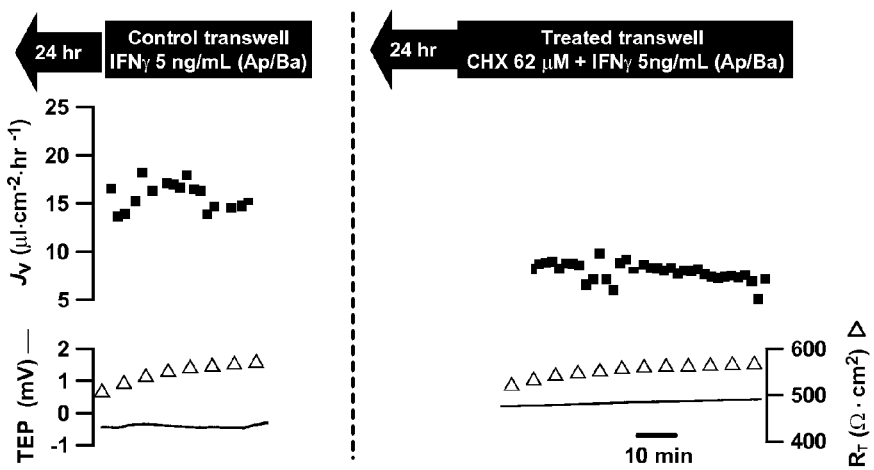
FIG. 14I depicts two traces: the top trace shows the net fluid absorption (apical to basal bath) in paired hfRPE cultures after 24 hour treatment with 5 ng/mL IFNγ or 5 ng/mL IFNγ and cyclohexamide (62 μM), each in the apical and basal baths, and mounting in a modified Üssing chamber, as a plot of $J_V$ (μl·cm$^{-2}$·hr$^{-1}$, ■) as a function of time; the bottom trace shows the plots of TEP (mV, –) and $R_T$ (Ω·cm$^2$, Δ) as functions of time. The results demonstrate that chronic treatment with CHX decreased $J_V$. (n=2).

Since CHX blocked IRF-1 synthesis after 4 hours of incubation (FIG. 2B), the effects of chronic exposure to CHX on the IFNγ-induced $J_V$ increase were examined. After 4 hours of pre-treatment with CHX, there was no IFNγ-induced $J_V$ increase or further effect of the CFTR inhibitor on $J_V$ (FIG. 14H). This result was also observed in two additional experiments (data not shown). Next, paired RPE tissues were treated with IFNγ (5 ng/ml; apical/basal) or IFNγ (5 ng/ml, apical/basal) and CHX (62 μM; apical/basal) for 24 hours. Compared to control, cyclohexamide treatment decreased $J_V$ from 15.9 to 8.8 $\mu l \cdot cm^{-2} \cdot hr^{-1}$ across RPE (FIG. 14I). A similar result was obtained in another experiment which decreased $J_V$ from 14.9 to 9.8 $\mu l \cdot cm^{-2} \cdot hr^{-1}$ (data not shown).

These effects of CHX suggest that the IFNγ-induced $J_V$ increase has two components, one that involves protein synthesis and one that does not. The results above demonstrate that the latter response is acute and not blocked by CHX. Thus, it is most likely mediated by down stream signals from JAK/STAT or p38 MAPK, or other second messengers that directly activate CFTR. On the other hand, the experiments above with chronic treatment with CHX indicate that the IFNγ-induced increase in $J_V$ is driven, at least in part, by activation of nuclear transcription factors and protein synthesis.

Example 19

Role of Second Messenger-Induced Changes in Jv: cAMP/PKA, [Ca$^{2+}$]$_I$, and Nitric Oxide (NO) in IFNγ-Induced Increase in J$_V$ It has been shown that cyclic AMP-induced (cAMP) activation of protein kinase A (PKA) leads to the activation of CFTR as described in Dahan, D., et al., *Pflugers Arch* 2001, 443 Suppl 1, S92-96; Hanrahan, J. W., et al., *J Exp Zool* 1996, 275, 283-291; Seibert, F. S., et al., *Biochim Biophys Acta* 1999, 1461, 275-283; Sheppard, D. N., et al., *Physiol Rev*, 1999, 79, S23-45; and Gadsby, D. C., et al., *Physiol Rev*, 1999, 79, S77-S 107, each incorporated herein by reference in its entirety.

Therefore, whether the CFTR pathway was involved in the response to IFNγ was examined using cAMP assays as described in Example 8. Primary cultures of hfRPE cells were incubated in control media, in the presence of IFNγ (0.5, 5, or 50 ng/ml), or in forskolin containing media (10 μM) for different amounts of time (5 minutes, 45 minutes, 12 hours, or 24 hours), and then total intracellular cAMP levels were measured using a cAMP ELISA System (Applied Biosystems, Foster City, Calif.). Forskolin significantly elevated intracellular levels of cAMP from 7.2 to 96.5 pmol/mg after 24 hours. (n=3; P<0.05). However, IFNγ had no apparent effect, at all concentrations tested and at all time points, on total intracellular cAMP relative to the control. In a separate set of experiments, fluorescence imaging was used to measure the intracellular concentration of calcium [Ca$^{2+}$]$_I$ in the presence of IFNγ (0.5, 5, 50 ng/ml) added to both sides of the hfRPE monolayer and no change in total cell [Ca$^{2+}$]$_I$ was observed (n=4, data not shown).

Figure 15A:
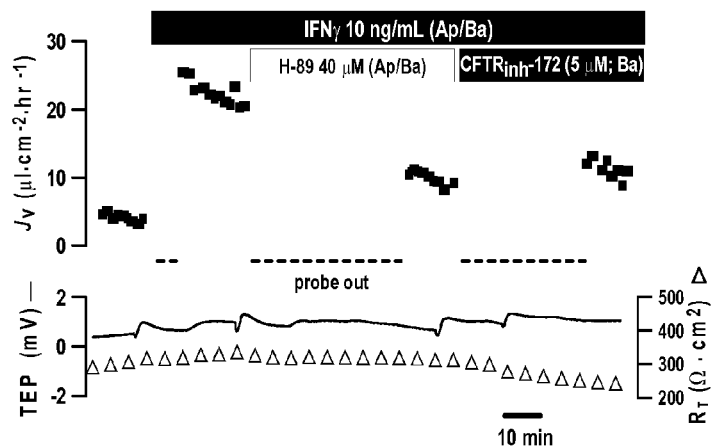
FIG. 15A depicts two traces: the top trace shows the net fluid absorption (apical to basal bath) in hfRPE cultures after treatment with 10 ng/mL IFNγ, addition of 40 μM H-89 to the apical and basal baths or subsequent addition of 5 μM CFTR inhibitor to the basal bath, as a plot of $J_V$ (μl·cm$^{-2}$·hr$^{-1}$, ■) as a function of time; the bottom trace shows the plots of TEP (mV, –) and $R_T$ (Ω·cm$^2$, Δ) as functions of time. The results indicate that the less specific PKA inhibitor H-89 blocked the IFNγ increase in $J_V$, and that the CFTR inhibitor had no further effect on the $J_V$ increase by IFNγ. (n=3, P<0.05).

Even though IFNγ did not elicit measurable cAMP signals in hfRPE, the effect of H-89, a specific PKA inhibitor, on J$_V$ was measured to rule out a possible role of cAMP in the observed IFNγ stimulated fluid transport increase. H-89 (40 μM) significantly blocked the IFNγ stimulated J$_V$ increase (FIG. 15A). Addition of CFTR$_{inh}$-172 had no further effect on IFNγ-induced fluid transport. In three experiments, IFNγ increased mean J$_V$ from 8.4±1.6 μl·cm$^{-2}$·hr$^{-1}$ to 20.1±0.2 μl·cm$^{-2}$·hr$^{-1}$ (P<0.05) and addition of H-89 (40 μM, both sides) decreased J$_V$ to baseline level, 8.3±1.3 μl·cm$^{-2}$·hr$^{-1}$. Pre-treatment with H-89 (40 μM) for 30 minutes had no significant effect on the baseline level of J$_V$, but completely blocked the effect of IFNγ. In four experiments, the mean steady-state J$_V$ was 12.8±5.2 μl·cm$^{-2}$·hr$^{-1}$. This baseline was not significantly altered by treatment with H-89 (J$_V$=12.9±3.7 μl·cm$^{-2}$·hr$^{-1}$) or the subsequent addition of IFNγ (J$_V$=14.7±4.7 μl·cm$^{-2}$·hr$^{-1}$) (data not shown).

Figure 15B:
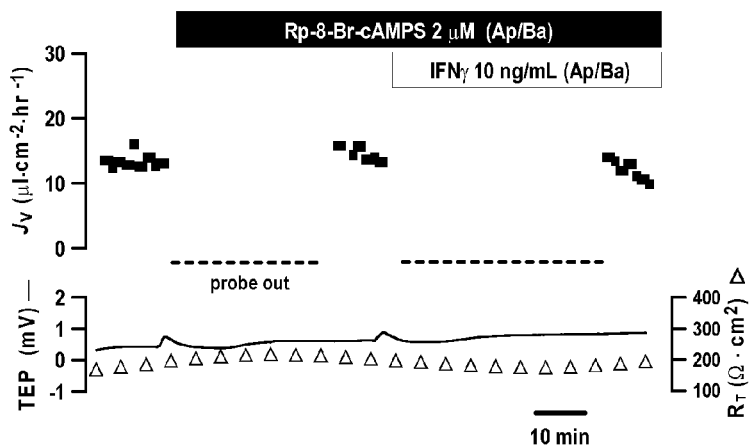
FIG. 15B depicts two traces: the top trace shows the net fluid absorption (apical to basal bath) in hfRPE cultures after the addition of 5 ng/mL IFNγ following pretreatment with 2 μM Rp-8-Br-cAMPS for 30 minutes, as a plot of $J_V$ (μl·cm$^{-2}$·hr$^{-1}$, ■) as a function of time; the bottom trace shows the plots of TEP (mV, –) and $R_T$ (Ω·cm$^2$, Δ) as functions of time. The results demonstrate that the more specific PKA inhibitor Rp-8-Br-cAMPs blocked the IFNγ-induced increase in $J_V$, indicating that PKA mediates the IFNγ effect. (n=6).

A more specific PKA inhibitor than H-89, Rp-8-Br-cAMPS, was also tested (FIG. 15B) as described in Murray, A. J., *Sci, Signal,* 2008, 1, re4 and Lochner, A., et al., *Cardiovasc Drug Rev,* 2006, 24, 261-274, each incorporated herein by reference in its entirety. Incubation with Rp-8-Br-cAMPS (2 μM) for approximately 40 minutes had no effect on baseline J$_V$, but completely blocked the effects of IFNγ. In six experiments, the mean steady-state J$_V$ was 8.9±1.2 μl·cm$^{-2,-1}$. This baseline was not significantly altered by treatment with Rp-8-Br-cAMPS (10.4±2.0 μl·cm$^{-2}$·hr$^{-1}$) and the subsequent addition of IFNγ produced no significant change in J$_V$ (8.4±1.7 μl·cm$^{-2}$·hr$^{-1}$) in the continued presence of this inhibitor (2 μM)

The fact that IFNγ did not change total cell cAMP, as described above, in hfRPE suggested two possible mechanisms. The first is that the entire response is mediated by IRF-1 induced nitric oxide production. Another possibility is that IFNγ induces a localized change in cAMP near the basolateral membrane where the electrical changes are generated, as described above. Indeed, this hypothesis is supported by the above described effects of PKA inhibitors, H-89 or Rp-8-Br-cAMPS, which blocked the IFNγ-induced J$_V$ increase.

Example 20

Role of P38 in IFNγ-Induced Increase in J$_V$

Figure 16A:
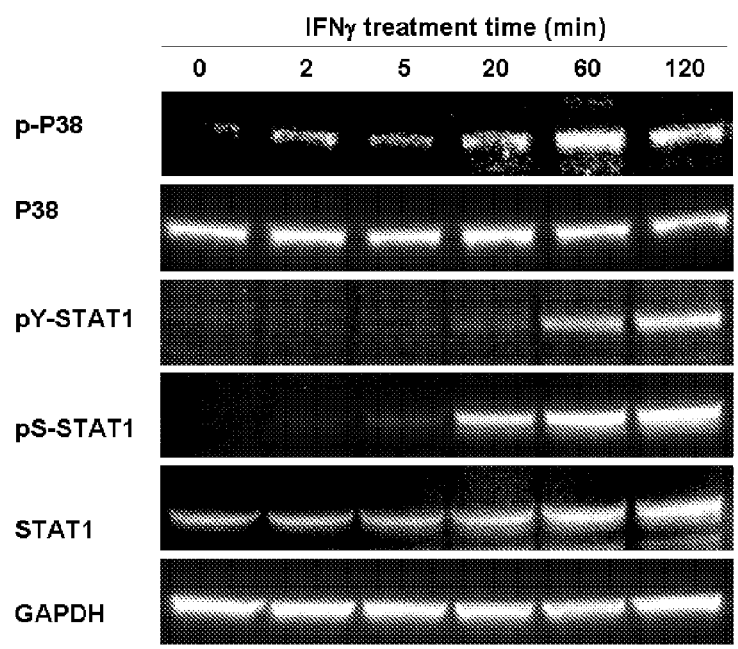
FIG. 16A is an image of immunoblots depicting the protein expression of (in order of top to bottom): phosphorylated P-38, pan P-38, tyrosine-phosphorylated STAT1 (pY-STAT1), serine phosphorylated STAT-1 (pS-STAT1), and total STAT1 in hfRPE cells grown to confluence, serum starved for 24 hours, and treated with IFNγ for various lengths of time. GAPDH is shown as a control for protein loading. The image demonstrates that IFNγ induced phosphorylation of P38 within 2-5 minutes, and this response peaked at about 1 hour and began to decline at about 2 hours.

Previous results showed that P38 MAPK mediates the flagellin-induced activation of CFTR-dependent Cl secretion in Calu-3 cells, as described in Zhang, Z., et al., *Infect Immun* 2007, 75, 5985-5992, and Illek, et al., 2008, in press, each incorporated herein by reference in its entirety. Therefore, whether one or more MAP kinases, including JNK, P38, and P44/P42, played a role in IFNγ stimulated fluid transport across RPE monolayers was examined using immunoblotting as described in Example 3. IFNγ had no effect on JNK or P44/P42 phosphorylation at all of the six time points tested (data not shown). However, as compared to the initial baseline, addition of IFNγ induced phosphorylation of P38 MAPK within 2 to 5 minutes (FIG. 16A). This response peaked at one hour and started to decline at approximately two hours (FIG. 16A).

Figure 16B:
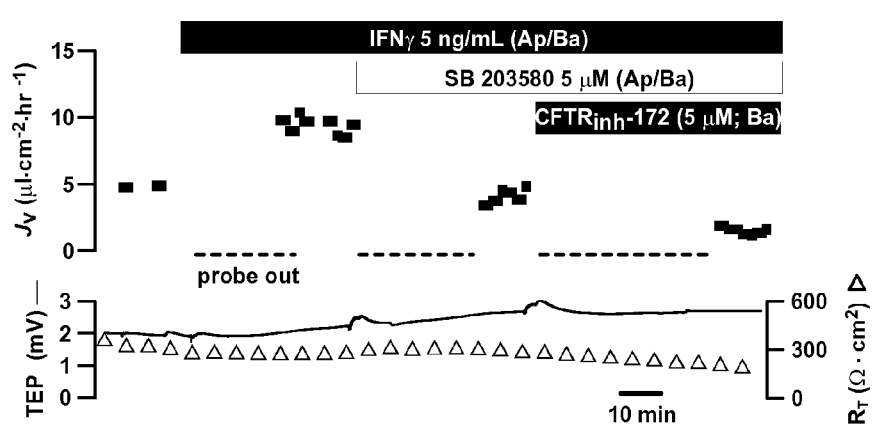
FIG. 16B depicts two traces: the top trace shows the net fluid absorption (apical to basal bath) in hfRPE cultures after treatment with 5 ng/mL IFNγ in the apical and basal baths, addition of 5 μM P38 MAPK inhibitor (SB 203580) to the apical and basal baths and further addition of 5 μM CFTR blocker to the basal bath, as a plot of $J_V$ (μl·cm$^{-2}$·hr$^{-1}$, ■) as a function of time; the bottom trace shows the plots of TEP (mV, –) and $R_T$ (Ω·cm$^2$, Δ) as functions of time. The SB 203580 specific inhibitor of P38 MAPK decreased IFNγ induced $J_V$ (P<0.001), which was further decreased by addition of CFTR inhibitor. (n=9)

The effect of P38 MAPK inhibitors on IFNγ stimulated fluid transport was then examined as described in Example 9 (FIG. 16B). A P38 MAPK specific inhibitor, SB203580 (5 μM), decreased IFNγ-induced J$_V$ by approximately 62%. IFNγ stimulated fluid transport was also blocked, by approximately 46%, by another P38 MAPK specific inhibitor, SB202190 (1-5 μM). A further decrease in J$_V$ was produced by subsequent addition of CFTR$_{inh}$-172, a CFTR inhibitor described above, to the basal bath.

In nine experiments, IFNγ increased mean J$_V$ from 7.5±1.9 μl·cm$^{-2}$·hr$^{-1}$ to 16.5±2.2 μl·cm$^{-2}$·hr$^{-1}$ (P<0.05) and addition of P38 MAPK inhibitor (1-5 μM, both sides) decreased J$_V$ to baseline −6.7±1.2 μl·cm$^2$·hr$^{-1}$ (P<0.001). In another set of experiments (n=6), pretreatment with SB203580 for ≥30 minutes had no significant effect on the baseline level of J$_V$, but completely blocked the effect of IFNγ. Furthermore, the addition of CFTR$_{inh}$-172 following SB203580 inhibition of IFNγ-induced J$_V$ produced a further decrease, but SB203580 had no further effect on J$_V$ following inhibition by basal bath CFTR$_{inh}$-172 (n=3, data not shown). This suggests that p38 MAPK is part of the CFTR signaling pathway.

Example 21

Mediation of IFNγ-Induced Changes in TEP and R$_T$ by cAMP

Since the fluid transport chamber experiments described in Example 9 primarily measured steady-state J$_V$, TEP, and R$_T$, the experiments did not allow determination of the more rapid changes in hfRPE voltage and resistance produced by IFNγ or other secretagogues, e.g. forskolin or 8-Br-cAMP. Therefore, the conventional electrophysiological approach using small perfusion chambers described in Example 10 was used to measure changes in membrane potential and resistance. This method allowed the rapid exchange of bathing media on either side of the confluent monolayer, and therefore permitted measurement of the relatively fast electrical changes in membrane potential and resistance.

Figure 17A:
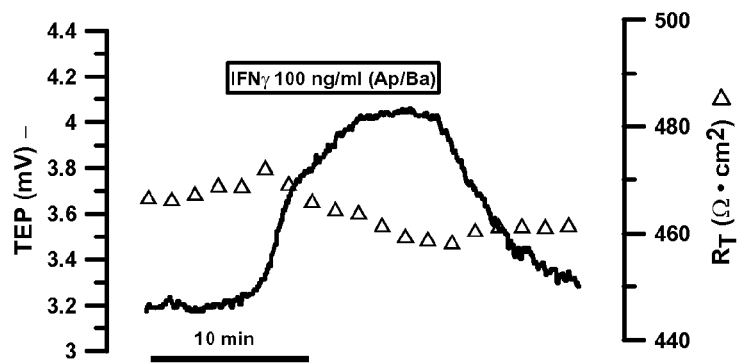
FIG. 17A is an electrophysiology recording depicting IFNγ-induced changes in TEP (–) and $R_T$ (open diamonds) of hfRPE cells following perfusion of IFNγ in both the apical and basal baths in a modified Üssing chamber, which allows rapid perfusion and the recording of rapid electrical changes. The results demonstrate an increase in TEP and a decrease in $R_T$. In total 5 experiments, the TEP increased 0.5±0.1 mV (P=0.02) and $R_T$ decreased 17±2 Ω·cm$^2$ (P=0.001).

Perfusion of IFNγ (100 ng/ml) to both the apical and basal baths produced changes in hfRPE TEP (0.9 mV increase) and R$_T$ (15 Ω·cm$^2$ decrease) (FIG. 17A). Similar results were obtained in another four experiments (ΔTEP=0.5±0.1 mV (P=0.02); ΔR$_T$=17±2 Ω·cm$^2$(P=0.0001)). Subsequent addition of the CFTR$_{inh}$-172 to the basal bath caused both membrane potential to hyperpolarize, decreased TEP, and increased R$_T$ along with a slight decrease in R$_A$/R$_B$. In five experiments, the mean resting potential (V$_A$) and TEP prior to the addition of exogenous cAMP was −44.2±1.5 mV and 0.7±0.4 mV, respectively.

Figure 17B:
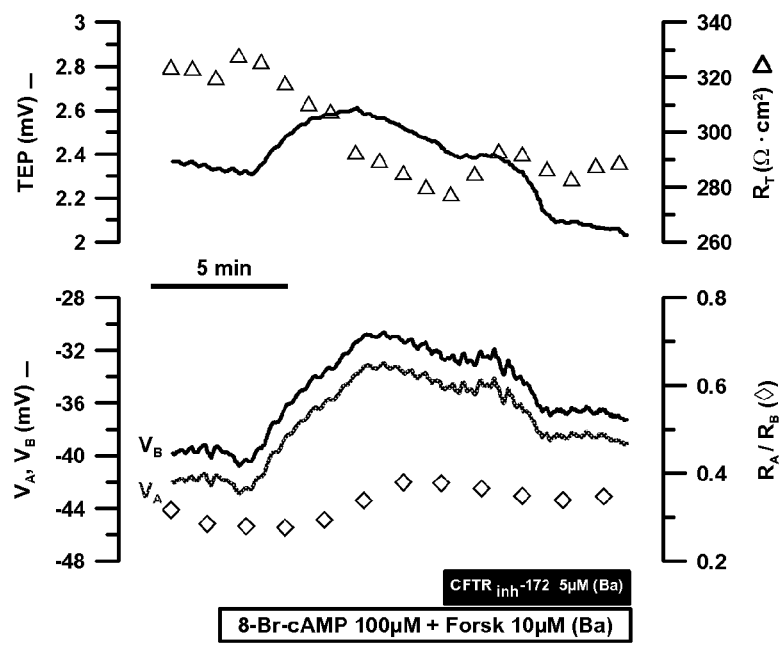
FIG. 17B is an electrophysiology recording depicting the effect of treatment of hfRPE cells with forskolin and 8-Br-cAMP: a 0.4 increase in TEP (mV, –), a decrease in $R_T$ (47 Ω·cm$^2$, open diamonds), a depolarization of both $V_B$ (basolateral membrane potential in mV, solid line as indicated) and $V_A$ (apical membrane potential in mV, solid line as indicated) by about 9 mV, where the rate of depolarization was greater at the basolateral as compared to the apical membrane, and a 0.1 increase in $R_A/R_B$. (n=5).

If the response was mainly mediated by an elevation in cellular cAMP, then similar changes in TEP and R$_T$ should be observed following treatment with a cAMP cocktail (forskolin and 8-Br-cAMP), which is known to significantly elevates intracellular cyclic AMP more than 10-fold. Therefore, cAMP-induced changes in apical (V$_A$) and basolateral membrane potential (V$_B$) and the change in TEP were measured simultaneously using intracellular recordings. In addition, the changes in R$_T$ and changes in the ratio of apical to basolateral membrane resistance (R$_A$/R$_B$) were also recorded. Addition of exogenous forskolin and 8-Br-cAMP significantly depolarized the basolateral membrane by 4.6±1.1 mV and decreased R$_T$ by 40±8.7 Ω·cm$^2$ (P=0.02). These changes taken together provide strong evidence that elevating cAMP in hfRPE activates a basolateral membrane cAMP-dependent anion channel (CFTR) whose equilibrium potential is less negative than the basolateral membrane resting potential. (FIG. 17B).

These electrophysiology experiments, which were carried out in a modified fast-flow Üssing chamber, further support the hypothesis that IFNγ induces a localized change in cAMP near the basolateral membrane where the electrical changes are generated, as described above. FIG. 17B shows that elevating cell cAMP produced cell membrane voltage and resistance changes, all of which are consistent with cAMP-activation of CFTR and these electrical changes were blocked by CFTR$_{inh}$-172. Similar TEP and R$_T$ changes were produced following the activation of the IFNγ receptor, indicating that cAMP is a critical part of this signaling pathway.

Example 21

IFNγ Stimulates Fluid Transport Across Rat RPE In Vivo

A previously tested in vivo rodent model of retinal detachment was used to measure the effect of IFNγ on re-absorption following retinal detachment, as described in Example 11 and in Maminishkis, A., et al., *Invest Ophthalmol Vis Sci*, 2002, 43, 3555-3566, incorporated herein by reference in its entirety. Initial detachment was created by injecting approximately 1 μl of osmotically-balanced, modified phosphate-buffered saline (MPBS) Ringer's solution into the extracellular space, i.e. the sub-retinal space (SRS). After stabilization of the detachment, IFNγ (40 μl of 100 ng/ml) was added to the anterior surface of the eye via eye drops (Celluvisc®. A series of 3D OCT images were recorded at different time points.

Figure 23:
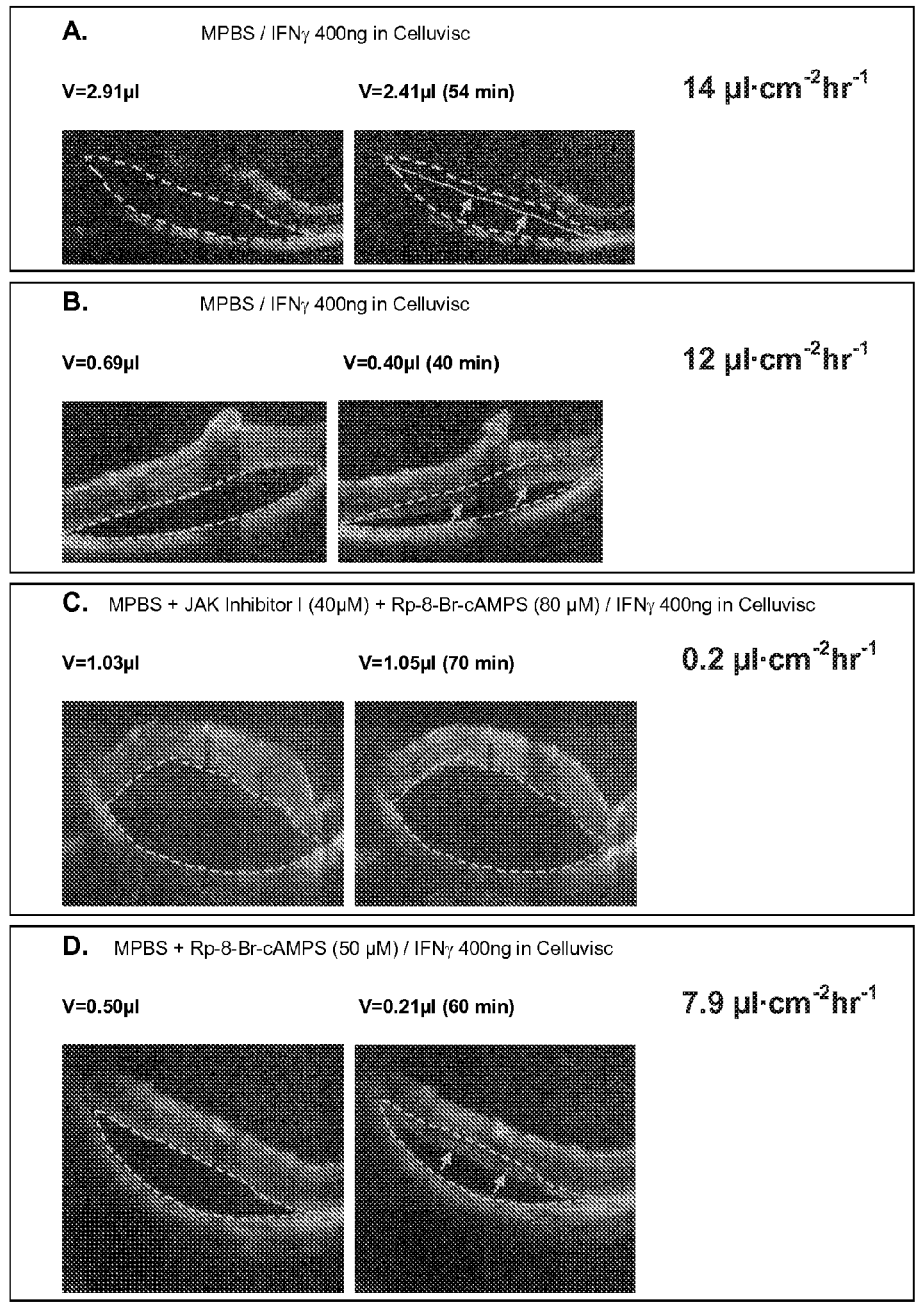
FIG. 23A depicts two images demonstrating retinal detachment in an intact rat eye and subsequent reattachment in response to 400 ng of IFNγ, at 54 minutes as indicated, as measured by the volume change of the detached area using 3D optical coherence tomography (OCT). Detachment was induced by injection of 1 μL, MPBS into the extracellular (i.e. subretinal) space between the photoreceptors and the RPE apical membrane, detachment volume was allowed to stabilize, and a 3D OCT image was recorded just before IFNγ application (left panel). The dotted line delineates the original detachment area (left and right panels). IFNγ containing drops were applied to the anterior portion of the eye, the IFNγ induced decrease in volume was observed, and 3D OCT images were recorded after 54 minutes (right panel). The transport rates are shown to the right of both panels ($J_V$ in μl·cm$^{-2}$·hr$^{-1}$).
FIG. 23B depicts two images demonstrating retinal detachment in an intact rat eye and subsequent reattachment in response to IFNγ as performed in FIG. 18A, where 3D OCT images were recorded just before IFNγ treatment (left panel) and at 70 minutes (right panel).
FIG. 23C depicts two images demonstrating retinal detachment in an intact rat eye and subsequent reattachment in response to IFNγ as performed in FIG. 23A, where the IFNγ induced decrease in volume was blocked by pre-injection of 40 μM of JAK Inhibitor I and 80 μM the PKA inhibitor Rp-8-Br-cAMP, and where 3D OCT images were recorded just before IFNγ treatment (left panel) and at 70 minutes (right panel).
FIG. 23D depicts two images demonstrating retinal detachment in an intact rat eye and subsequent reattachment in response to IFNγ as performed in FIG. 23A, where the IFNγ induced decrease in volume was partially blocked by pre-injection of 50 μM the PKA inhibitor Rp-8-Br-cAMP alone, and where 3D OCT images were recorded just before IFNγ treatment (left panel) and at 60 minutes (right panel).
FIG. 23E depicts additional views of the 3D rendering of the OCT optical sections at the two time points shown in FIG. 23B, at 0 minutes (upper left panel) and 40 minutes (upper right panel), respectively. Alternate views are also shown (enface view at 0 and 40 minutes—middle panel; additional tilted view at 0 and 40 minutes—bottom panel).
FIG. 23F depicts a bar graph summarizing the results of three retinal detachment experiments as performed in FIGS. 23A, B, and C ($J_V$ transport rates in response to IFNγ alone, incubation with JAK inhibitor I and PKA inhibitor Rp-8-Br-cAMP (JAK+PKA inhibitors), and IFNγ treatment in the presence of these inhibitors and after pre-injection with the same inhibitors).

FIGS. 23A and B show that addition of IFNγ to the anterior surface of the eye caused a decrease in detachment size (volume). In each case, the panel on the left shows the OCT optical section obtained just before IFNγ addition and the right-hand panels show the OCT optical sections 40 or 54 minutes later (B and A panels, respectively). The green dotted line in the left-hand image delineates the detachment size just before addition of IFNγ. This same traced area is superimposed on the right-hand side to help visualize the changes in detachment size over time. In panels A and B, the green arrows point to the new position of the retinal border at 54 or 40 minutes, respectively. The fluid transport rates are shown in blue, and were calculated by reconstructing the volume and area of the detachment. FIG. 23E shows a 3D rendering of the OCT optical sections from the two time points, at t=0 and 40 minutes, in panel B (J$_V$=12 μl·cm$^{-2}$·hr$^{-1}$). Pseudo coloring is used to help visualize the area and depth of the detachment (blue). The middle panel is an enface view of the detachment showing that at 40 minutes there was a significant diminution of the detachment area and reduction in detachment height. The top and bottom panels in FIG. 23E show tilted views of this detachment.

FIGS. 23C and D show that the anterior surface IFNγ-induced changes in J$_V$ can be blocked completely or partially by injecting JAK/STAT inhibitors into the subretinal space (SRS). In these experiments we injected MPBS under the retina to create the initial detachment and included a cocktail of JAK inhibitor I and Rp-8-Br-cAMP or Rp-8-Br-cAMP blocker alone. FIG. 23D shows that the PKA inhibitor alone was not sufficient to completely block the effect of IFNγ (~40% reduction in absorption rate). However, the cocktail of both inhibitors can completely block the effect of IFNγ. This result was corroborated in a total of three experiments and the data is summarized in FIG. 23F.

Example 22

Figure 18:
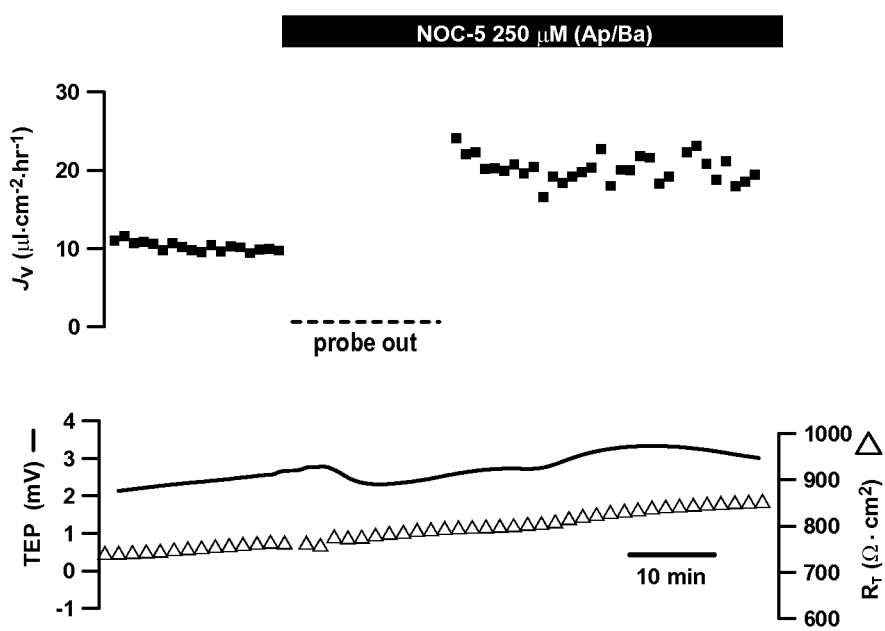
FIG. 18 depicts two traces that demonstrate that the NO donor NOC-5 more than doubled $J_V$ (n=3). The top trace shows the net fluid absorption (apical to basal bath) in hfRPE cultures after the addition of NOC-5 to the apical and basal baths, as a plot of $J_V$ (μl·cm$^{-2}$·hr$^{-1}$, Δ) as a function of time; the bottom trace shows the plots of TEP (mV, –) and $R_T$ (Ω·cm$^2$, Δ) as functions of time.

Nitric Oxide Donor NOC-5 Increases Jv and iNOS Inhibitor Inhibited IFNγ-Induced J$_V$ Increase As the data in Table I show that IFNγ increased the expression of inducible nitric oxide synthase (iNOS or NOS2A), the ability of an NO donor to directly affect Jv was tested. The nitric oxide donor NOC-5 more than doubled Jv, as shown in FIG. 18 (n=3). The addition of CFTR inhibitor (CFTR$_{inh}$-172) blocked this NOC-5 induced increase in Jv, as shown in FIG. 19 (n=3).

Figure 20:
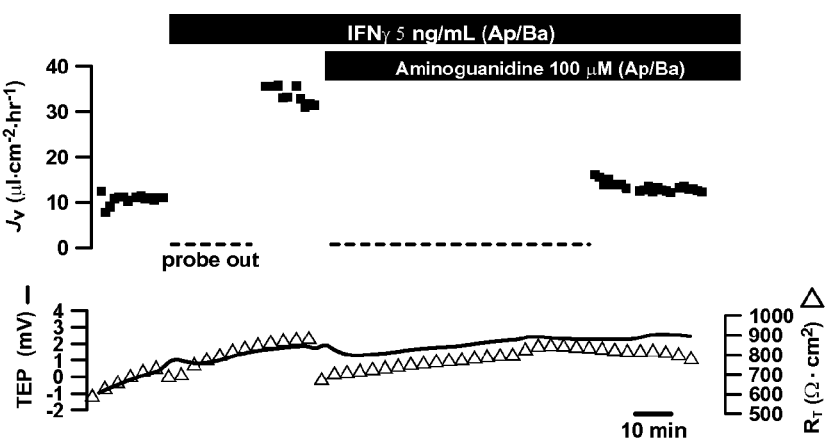
FIG. 20 depicts two traces that demonstrate that an iNOS inhibitor (aminoguanidine hydrochloride) blocks IFNγ-induced increase in $J_V$: the top trace shows the net fluid absorption (apical to basal bath) in hfRPE cultures after treatment with IFNγ 5 ng/ml and subsequent addition of 100 μM aminoguanidine to the apical and basal baths as a plot of $J_V$ (μl·cm$^{-2}$·hr$^{-}$, ■) as a function of time; the bottom trace shows the plots of TEP (mV, –) and $R_T$ (Ω·cm$^2$, Δ) as functions of time. (n=3).

To test whether the effect of IFNγ-induced J$_V$ increase is mediated through NO, an iNOS inhibitor, aminoguandidie hydrochloride, was applied after treatment of IFNγ. As shown in FIG. 20, the iNOS inhibitor does block IFNγ induced increase in Jv (n=3). In another set of experiments, pre-treatment with this inhibitor completely blocked IFNγ induced increase in Jv (n=3).

Figure 19:
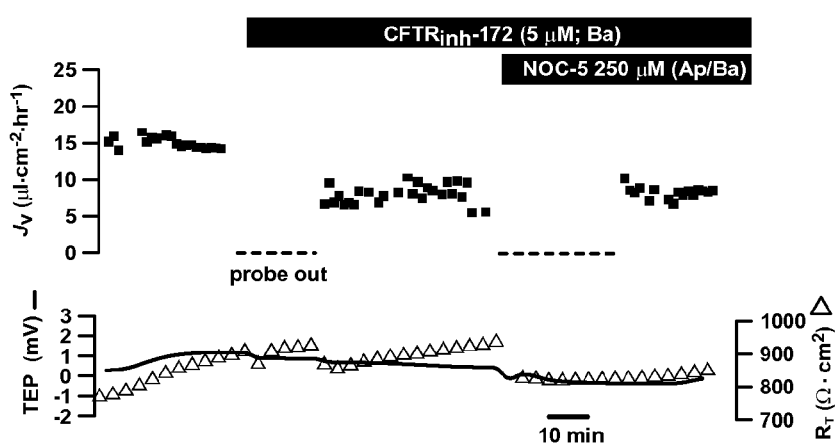
FIG. 19 depicts two traces: the top trace shows the net fluid absorption (apical to basal bath) in hfRPE cultures after the addition of 250 μM NOC-5 to the apical and basal baths following pre-treatment with CFTR inhibitor (5 μM) for 30 minutes in the basal bath, as a plot of $J_V$ (μl·cm$^{-2}$·hr$^{-1}$, ■) as a function of time; the bottom trace shows the plots of TEP (mV, –) and $R_T$ (Ω·cm$^2$, Δ) as functions of time. (n=3).
Figure 21:
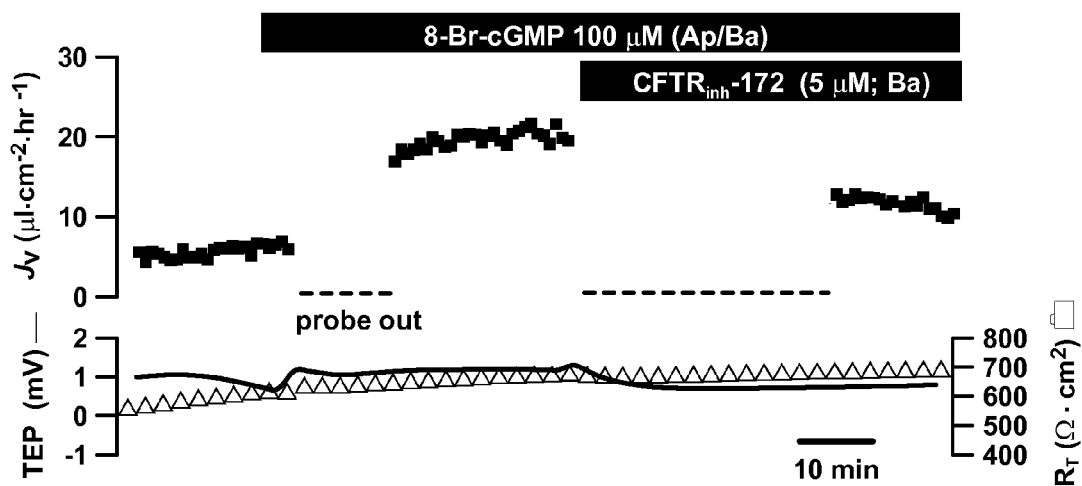
FIG. 21 depicts two traces. The top trace shows the net fluid absorption (apical to basal bath) in hfRPE cultures after treatment with 100 μM 8-Br-cGMP in both apical and basal baths and subsequent addition of CFTR inhibitor (5 μM) to the basal bath, as a plot of $J_V$ (μl·cm$^{-2}$·hr$^{-1}$, ■) as a function of time. The bottom trace shows the plots of TEP (mV, –) and $R_T$ (Ω·cm$^2$, Δ) as functions of time. These results indicate that 8-Br-CGMP increase $J_V$ across hfRPE monolayers, which can be blocked by the addition of CFTR inhibitor.
Figure 22:
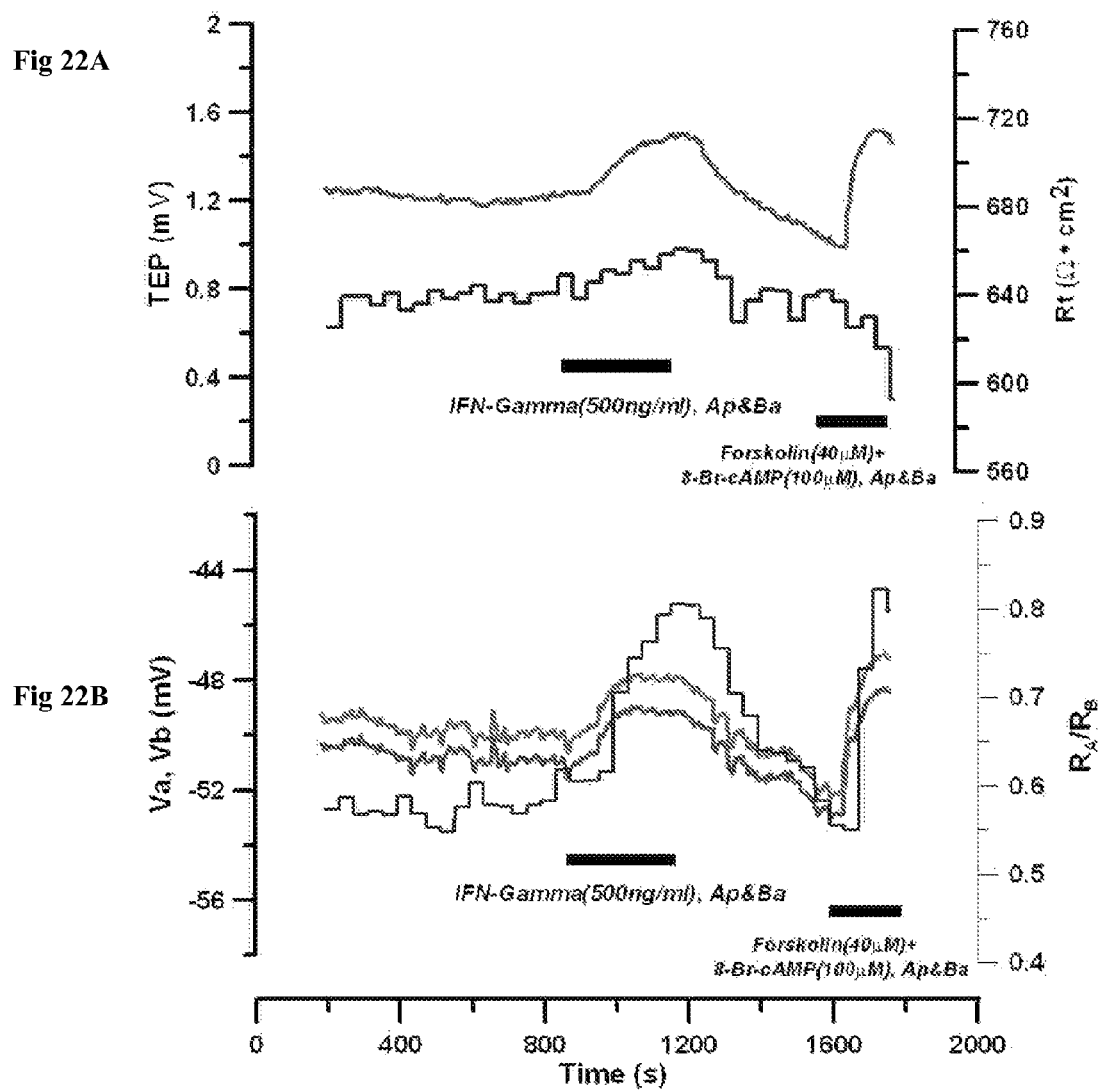
FIG. 22 is an electrophysiology recording depicting IFNγ-induced changes in TEP, $R_T$, $V_A$, $V_B$ and $R_A/R_B$ of hfRPE cells following perfusion of 500 ng/mL IFNγ in both the apical and basal baths in a modified Üssing chamber followed by the addition of 40 uM Forskolin and 100 uM 8-Br-cAMP in both the apical and basal baths. IFNγ depolarized both $V_A$ (apical membrane potential in mV, solid line) and $V_B$ (basolateral membrane potential in mV, solid line) by approximately 2.5 mV (lower panel, B) and increased TEP (0.3 mV, upper panel, A) indicating the depolarization rate was greater at the basolateral compared to the apical membrane. During this time the $R_A/R_B$ increased by 0.2.

While the results in previous examples indicate an important role for local cAMP and CFTR, taken together, the experiments described in FIGS. 19, 20, and 21, with NO donors and iNOS inhibitors indicate that NO is also a significant contributor to the IFNγ response.

Example 23 cGMP Stimulated Jv Across hfRPE

The result shown in FIG. 21 demonstrate that 8-Br-cGMP increases J$_V$ across hfRPE monolayers from 6.0 to 19.5 μl·cm$^{-2}$·hr$^{-1}$. This can be blocked by the addition of CFTR inhibitor CFTR$_{inh}$-172, and a reduction in Jv from 19.5 to 11.5 μl·cm$^{-2}$·hr$^{-1}$ is observed. In four experiments, an increase in Jv from 7.4±1.1 to 15.8±1.6 μl·cm$^{-2}$·hr$^{-1}$ was observed, and addition of CFTR inhibitor reduced the increase in Jv to 8.9±1.3 μl·cm$^{-2}$·hr$^{-1}$.

Intracellular recordings (data not shown) demonstrate that elevation of cellular cGMP depolarized both V$_A$ and V$_B$ by 2.5 mV and increased TEP by 0.3 mV, indicating that the depolarization rate was greater at the basolateral membrane than the apical membrane. Meanwhile, R$_A$/R$_B$ increased by 0.2

Example 24

Summary of IFNγ Signaling in RPE

Figure 24:
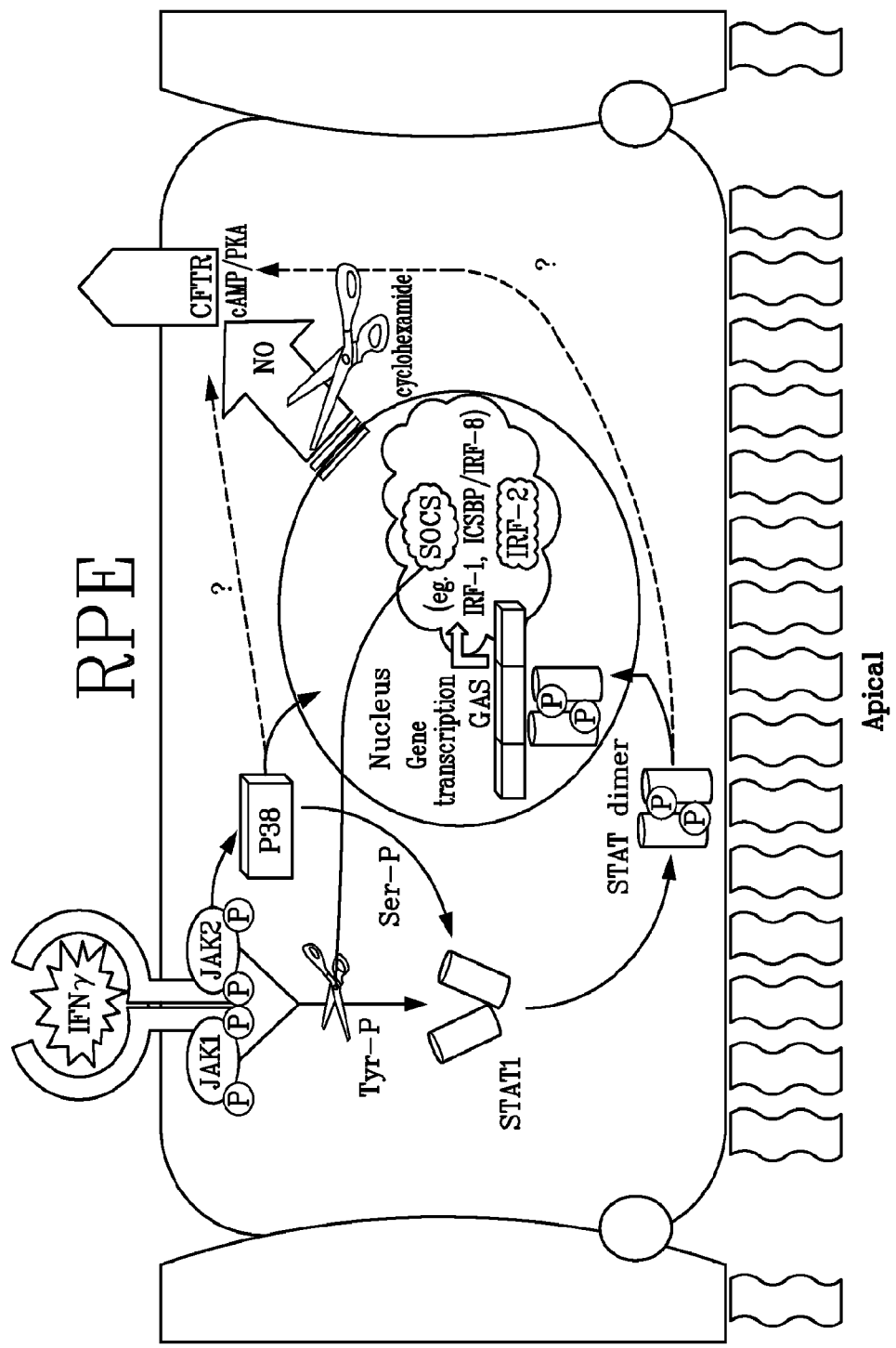
FIG. 24 is a pictorial representation of IFNγ signaling in RPE.
Figure 25A:
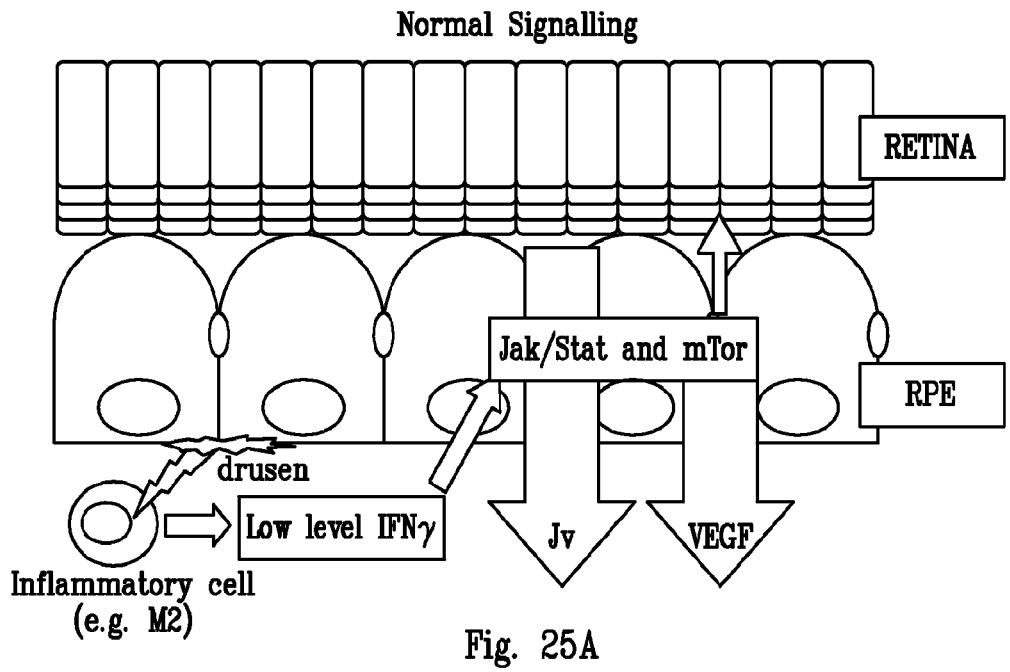
FIG. 25A is a pictorial representation of normal IFNγ signaling in RPE involving the Jak/Stat and mTor pathways.
Figure 25B:
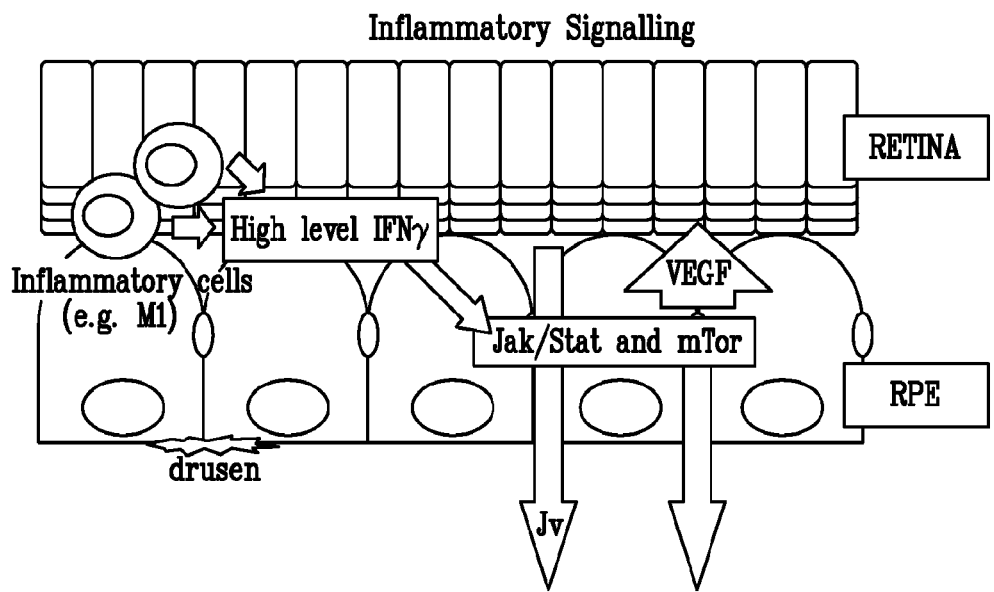
FIG. 25B is a pictorial representation of IFNγ signaling in RPE involving the Jak/Stat and mTor pathways under inflammatory stress.

The schematic model shown in FIG. 24 summarizes a set of intracellular signaling pathways and second messengers, as described above, that can mediate IFNγ-induced fluid transport across epithelia. In addition, a schematic of inflammatory signaling in RPE is shown in FIG. 25B, and a schematic of normally signaling RPE is shown in FIG. 25A. In hfRPE, acute (30 min) exposure to IFNγ increased net transepithelial fluid absorption from the retinal to the choroidal side of the tissue. In addition, chronic exposure to IFNγ significantly decreased total tissue resistance and RPE mitochondrial membrane potential. These physiological responses were generated following activation of the JAK/STAT1 and P38 MAPK pathways and the elevation of cAMP/PKA and nitric oxide, which activated basolateral membrane Cl channels (CFTR).

As described above, the mean IFNγ-induced resistance change at 24 hours is ≈240 Ω·cm$^2$ but this change does not impair transport as witnessed by the concomitant increase in $J_V$. This response is relatively small (≈2-fold) compared to the $R_T$ changes produced by the ICM cocktail and suggests an effect on the cellular pathway (eg, increased channel conductance) rather than an effect on the tight junctions that form the paracellular pathway. Excessive growth of choroidal cells can lead to disruption of Bruch's membrane, the subsequent disruption of the RPE barrier, and blood vessel entry into the subretinal space, a hallmark of AMD.

Previously it was shown that pro-inflammatory stimuli, including IFNγ, cause the RPE to secrete physiologically relevant amounts of pro- and anti-angiogenic cytokines, especially MCP-1 and IL-8, to the retinal/photoreceptor side of the RPE, as described in Edelmen, J L, et al., 1991, *Invest Ophthalmol Vis Sci*, 32, 3033-3040; and Shi, G., et al., 2008, *Invest Ophthalmol Vis Sci*, 49, 4620-4630, hereby incorporated by reference in their entireties. IFNγ activates CFTR, and ion-coupled increases in fluid transport from the retinal to choroidal side of the RPE would tend to dehydrate the subretinal space. Strong evidence for this comes from the in vivo experiments in the rat model of retinal re-attachment above, where we showed that addition of IFNγ to the anterior surface of the rat eye significantly increased the rate of fluid absorption from the subretinal space in less than 30 minutes. In rat, as in human, these IFNγ-induced increases in fluid absorption are blocked by Jak/STAT pathway inhibitors, as shown in FIG. 23C.

This has important implications for treatment of uveitis, as described herein. Whereas in a normal RPE cell, it may be that both the mTOR the Jak/Stat pathways are functioning simultaneously to maintain the normal retinal turgidity. However, the Jak/Stat pathway, if stimulated from the basal side, will induce fluid absorption to resolve edema, whereas activation of the mTOR pathway would provide signaling for compensatory (in many cases pathological) immune system activation and neovascularization, as shown in FIGS. 25A and 25B. Using IFNγ can provide therapeutic effect to reverse pathological changes associated with uveitis, with or without an mTOR pathway inhibitor such as sirolimus.

Example 25

IFNγ Treatment and Measurement of Macular Thickness in Patients with CME Secondary to Uveitis To test whether cystoid macular edema (CME), secondary to uveitis, is caused by the disequilibrium of the Jak/Stat and mTor signal transduction pathways in the retinal pigment epithelium (RPE), interferon gamma-1β topically applied in human patients. Five participants with CME secondary to uveitis receive a topical ocular instillation of interferon gamma-1b in a Phase I, non-randomized, prospective, uncontrolled, dose-escalation, single-center study. The study involves a one-time instillation or series of instillations of interferon gamma-1b on the cornea and measurement of a response with optical coherence tomography (OCT) over a three hour period.

A 25% decrease in macular thickness is observed at a post-instillation as compared to baseline. In the study, the first two participants receive one instillation (each instillation contains 10 μg in 0.05 mL solution) on the cornea at time zero, the next two participants receive two instillations, 10 minutes apart, for a total dosage of 20 μg, and the final participant receives three instillations, 10 minutes apart, for a total of 30 μg. OCT will be obtained at −60 minutes, −30 minutes and just before the instillation(s). Repeat OCTs will be taken at +30 minutes, +60 minutes and +120 minutes. All participants return for a one-week safety visit.

As described above, the primary outcome is the change in central macular thickness as measured by OCT in response to interferon gamma-1b as compared with baseline. Secondary outcomes include changes in macular volume as measured by OCT, visual acuity, intraocular pressure, intraocular inflammation and ocular surface irritation assessed by fluorescein staining of the cornea and conjunctiva to assess toxicity. For safety measurements, the following are measured: the presence of ocular surface irritation assessed by fluorescein staining of the cornea and conjunctiva to assess toxicity; the number and severity of systemic and ocular toxicities and adverse events; and the proportion of participants with a visual loss of ≥15 ETDRS letters.

Based on therapeutic treatment of topical IFNα, topically applied IFNγ is well-tolerated. Topically applied IFNα is described in Hu F R, et al., *Am J Ophthalmol*, 1998: 125:118-9; Karp C L et al., *Ophthalmology*, 2001, 108:1093-8; Schechter B A, et al., *Cornea*, 2002: 21:6-11; Esquenazi S, et al., Br J Ophthalmol, 2005, 89:1221; Huerva V, et al., *J Ocul Pharmacol Ther*, 2007, 23:143-5; Sturges A, et al., *Ophthalmology*, 2008 August 115(8):1297-302, each of which is incorporated by reference in its entirety herein. The only minor side effects reported from the topical administration of IFNα from all of these studies were follicular conjunctivis and conjunctival injection. In addition, in the reported IFNα studies, participants received multiple instillations per day for months at a time. Here, patients receive a maximum of three instillations.

The primary objective is to investigate the safety and tolerability efficacy of an ocular instillation of interferon gamma-1b as a possible treatment for CME secondary to uveitis. Five participants receive study medication, however up to seven participants with intermediate, panuveitis or posterior uveitis with CME are optionally enrolled in this protocol. If a participant optionally withdraws prior to receiving any study medication, an additional participant is optionally accrued as a replacement. A maximum of two participants are replaced.

Participants have a diagnosis of intermediate, panuveitis or posterior uveitis of at least three months prior to study enrollment and has associated CME secondary to uveitis in at least one eye (the study eye). Participants have a central macular thickness≥250 microns in the study eye. Participants have a visual acuity of 20/200 or better in the study eye. Female participants of childbearing potential must not be pregnant or breast-feeding and must have a negative urine pregnancy test within 24 hours before study medication administration. Both female participants of childbearing potential and male participants able to father a child must agree to practice an adequate birth control during the study and for six weeks following the administration of study medication. Acceptable methods of birth control include hormonal contraception (birth control pills, injected hormones or vaginal ring), intrauterine device, barrier methods with spermicide (diaphragm with spermicide, condom and spermicide) or surgical sterilization (hysterectomy, tubal ligation or vasectomy).

Persons that are unable to tolerate the ocular instillation, unable to undergo OCT testing, have had herpes keratitis in the past, are diagnosed with multiple sclerosis, or have a significant active infection (an infection requiring treatment as determined by the medical team) or a history of chronic or recurrent infections that in the PI's best medical judgment are precluded from participation.

If both eyes meet the criteria specified for the study eye, the study eye is the eye with less CME.

Participants are recruited from the NEI uveitis clinic. In addition, the study is posted on the ClinicalTrials.gov, the NEI and the Clinical Center (CC)'s Web sites. Self-referral and referral from outside physicians is permitted.

Participants are screened under the NEI screening or evaluation and treatment protocol to establish eligibility. Baseline examinations are performed as outlined in Table II one to seven days prior to the study treatment visit. The procedures is performed on both eyes, where appropriate.

Participants with CME secondary to uveitis are treated with ocular instillation(s) of interferon gamma-1b. Each instillation contains a dose of 10 µg of interferon gamma-1b in 50 µL of fluid. The instillation is placed topically on the cornea of the study eye as outlined in the Administration section. The effect on the retinal thickness is measured using OCT measurements as indicated below.

All participants undergo a dilated ophthalmic examination the day of the testing. One eye is chosen as the study eye. The participants receive the evaluation around 12:00 p.m. Participants then have a OCT at −60 minutes, −30 minutes and just before the ocular instillation. The ocular instillation occurs no earlier than 1:00 p.m. Repeat OCT recordings are taken at +30, +60 and +120 minutes after instillation. There is a window of ±15 minutes for each OCT test.

OCT testing is performed with the Cirrus™ high-definition OCT (Carl Zeiss Meditec, Inc.) scanner using a 512×128 scan pattern where a 6×6-mm area on the retina is scanned with 128 horizontal lines, each consisting of 512 A-scans per line (a total of 65,536 sampled points) within a scan time of 2.4 seconds. The scanner automatically focuses on the macula. Data for macular thickness calculations are collected from an array of A-scans distributed across the macular using the macular thickness analysis algorithm. The three pre-instillation measurements are averaged to calculate the baseline macular thickness measurement. Post-instillation OCT macular thickness calculations (+30, +60 and +120 minutes) is compared to the baseline measurement separately. A 25% reduction in central macular thickness is observed in treated patients.

Participants perform punctal pressure occlusion for at least one minute in an attempt to prevent systemic absorption of the ocular instillation(s). The instillation(s) of the interferon gamma-1b and subsequent testing takes less than one day. At the end of the day's testing, participants are given a two-day supply of preservative-free artificial tears for application QID in the study eye.

All of the study procedures, with the exception of the administration of the ocular instillation(s) of interferon gamma-1b, are typical components of the clinical care required for a participant with uveitis. In this study, examinations are performed at the study visits as indicated in the study flow sheet as shown in Table II:

1. Medical/Ophthalmic History
2. Vital Signs
3. Concomitant Medication Assessment
4. Adverse Event Assessment
5. Manifest Refraction using ETDRS methods
6. Slit Lamp Examination
7. Intraocular Pressure (IOP)
8. Dilated Fundus Examination
9. Fluorescein Angiogram (FA)
10. Fundus Autofluorescence (FAF)
11. Optical Coherence Tomography (OCT)
12. Subjective Pain Assessment
13. Hepatitis Screening
14. HIV Testing
15. Chemistry 20 Panel
16. Liver Function Tests
17. Urinalysis (UA), including microscopic
18. Urine Pregnancy Test for Women of Child-Bearing Potential Formulation, Dosage, and Storage Interferon gamma-1b, (Actimmune®, InterMune, Inc, Brisbane, Calif. 94005), a biologic response modifier, is a single chain polypeptide containing 140 amino acids. Actimmune® is a highly purified sterile solution consisting of non-covalent dimmers of two identical 16,465 dalton monomers. Actimmune® is a sterile, clear, colorless solution. Each 50 microliters of solution contains 10 mcg (200,000 IU) of Interferon gamma-1b with 2 mg mannitol, 36 mcg of sodium succinate and 5 mcg of polysorbate 20 in sterile water for injection. This solution has a pH of approximately 5.2 and an osmolality of 221 mmol/kg.

Actimmune® is commercially available in a single-use vial at a concentration of 100 mcg per 0.5 mL (500 microliters). Vials of Actimmune® are placed in a 2-8° C. (36-46° F.) refrigerator immediately upon receipt to ensure optimal retention of physical and biochemical integrity. The vials are not frozen, excessive or vigorous agitation will be avoided and the vials will not be shaken. Unentered vials of Actimmune® should not be left at room temperature for a total time exceeding 12 hours prior to use. Vials exceeding this time should be discarded. Commercially available Actimmune® is used in this study. When ordered by the investigator, the exact dose is prepared by drawing the appropriate volume (0.05 mL, 0.10 mL or 0.15 mL) of the commercial solution into a tuberculin syringe. The syringe is capped with a sterile cap and sent to the floor for administration. For each instillation, a second back-up syringe is prepared and dispensed to ensure proper instillation.

Administration

Interferon gamma-1b is administered as follows:
1. Topical tetracaine 1% or proparacaine 0.5% drops are applied to the study eye surface one to two minutes prior to instillation.
2. The participant applies punctal pressure to his/her non-study eye.
3. The investigator holds the participant's study eye open.
4. A volume of 0.05 mL of interferon gamma-1b is instilled on the center of the study eye's cornea from a tuberculin syringe.
5. The participant continues applying punctal pressure to his/her non-study eye for at least one minute post-instillation.
6. Steps 1-5 are optionally repeated ten minutes post-instillation until the appropriate dosage has been administered, if an additional instillation is required.

7. The participant is given a two-day supply of preservative-free artificial tears for application QID in the study eye.

Study investigators will obtain informed consent. The Principal Investigator and the NEI Adverse Event Review Committee monitors data and safety. The EMMES Corporation (EMMES) is assigned as the coordinating center for this trial to conduct data collection, protocol monitoring, data analysis and reporting.

Alternative Therapies

Alternatives to participation include continuation with the current standard-of-care, which includes the use of systemic steroids, periocular steroids and systemic immunosuppressive agents, all of which are associated with significant side effects and complications if the treatment is extended and increased.

Example 26

NEI/ETDRS Methods for Determining Refraction and BCVA

This standard describes a single method for the measurement of visual acuity (which is strongly influenced by the methods used in the ETDRS and AREDS protocols) so that measurements obtained using the procedures listed below can be compared within and between sites as described in Ferris F L, et al., 1982, *Am J Ophthalmol,* 94:91-96, incorporated by reference in its entirety herein. Three methods are described to select the optical correction that will be used to measure visual acuity. Since determining this optical correction by manifest refraction is usually the lengthiest part of the evaluation of visual acuity, the three procedures listed below are, in

TABLE II

Study Flow Sheet

Visit Schedule

| | Baseline[1] | Pre-OCT | Study Treatment Visit Time (minutes) | | | | | | Post-OCT | Safety Visit[10] |
|---|---|---|---|---|---|---|---|---|---|---|
| | | | −60 min | −30 min | 1:00 p.m.[2] | +30 min[3] | −60 min[3] | +120 min[3] | | |
| Visit Number | 000 | | | | 007 | | | | | 014 |
| *Treatment* | | | | | | | | | | |
| Interferon Gamma-1b | | | | | X[4] | | | | | |
| *General Assessments* | | | | | | | | | | |
| Medical/Ophthalmic History | X | | | | | | | | | |
| Vital Signs | X | X | | | | | | | X | X |
| Concomitant Medications Assessment | X | X | | | | | | | | X |
| Adverse Event Assessment | | X | | | | | | | X | X |
| *Ophthalmic Assessments* | | | | | | | | | | |
| Manifest Refraction | X | | | | | | | | X | X |
| Slit Lamp Examination | X | | | | | | | | X | X |
| Intraocular Pressure (IOP) | X | | | | | | | | X | X |
| Dilated Fundus Examination | X | | | | | | | | X | X |
| Fluorescein Angiogram (FA) | X | | | | | | | | X | |
| Fundus Autofluorescence (FAF) | | X | | | | | | | X | X |
| Optical Coherence Tomography (OCT) | X | | X[5] | X[5] | X[6] | X[5] | X[5] | X[5] | | X |
| Subjective Pain Assessment | | X | | | X[7] | | | | X | X |
| *Laboratory Testing* | | | | | | | | | | |
| Hepatitis Screening | X | | | | | | | | | |
| HIV Testing[8] | X | | | | | | | | | |
| Chemistry 20 Panel | X | | | | | | | | | |
| Liver Function Testing | X | | | | | | | | | |
| Urinalysis (UA), including microscopic | X | | | | | | | | | |
| Pregnancy Testing (urine)[9] | | X | | | | | | | | |

[1]Baseline procedures are always completed 1 to 7 days prior to the Study Treatment Visit.
[2]Ocular instillation(s) occurs around 1:00 p.m., but no earlier.
[3]The target time for these procedures is calculated from the last instillation (if the participant receives more than one).
[4]The first two participants receive a single instillation (dosage of 10 μg) on the cornea at time zero. The next two participants receive two instillations on the cornea administered 10 minutes apart (a total dosage of 20 μg). The final participant receives three instillations, each administered 10 minutes apart (a total dosage of 30 μg).
[5]These OCT procedures must occur within ±15 minutes of the target time.
[6]The OCT procedure must occur immediately prior to the first ocular instillation.
[7]The assessment is completed immediately following the last instillation.
[8]The Clinical Center HIV Testing Policy will be followed if a positive HIV test result is uncovered.
[9]This test is for women of child-bearing potential and they must have a negative test within 24 hours prior to the study medication administration.
[10]The safety visit is completed one week after the Study Treatment Visit with a visit window of ±7 days the order from the most to the least time-consuming: measurement of best corrected visual acuity (BVCA) with required manifest refraction, measurement of corrected visual acuity with conditional manifest refraction, and measurement of corrected visual acuity without manifest refraction.

1. Measurement of BCVA with Required Manifest Refraction

This technique is utilized exclusively at visits to compare results obtained later in study where visual acuity is measured as an endpoint in a clinical research protocol. This "gold standard" method is preferably performed not more than once annually, unless an intervention (e.g., surgical treatment, or laser photocoagulation) that is expected to modify refractive error occurred. Best-corrected visual acuity is preferably obtained at baseline and on the additional study defined visits.

2. Measurement of Corrected Visual Acuity with Conditional Manifest Refraction

This technique requires a manifest refraction only if visual acuity declines or improves by 10 or more ETDRS letters (0.20 logMAR) as compared to the relevant baseline measurement. In the event of such a change in the visual acuity score, the baseline measurement is preferably changed to the score that triggered the "event." As refractive error does not vary frequently in adult participants with diseases of the posterior segment of the eye, this approach is used in follow-up protocol visits for these participants if no intervening events, e.g., a surgical procedure, suggest that refractive error has indeed changed.

3. Measurement of Corrected Visual Acuity without Manifest Refraction

This technique is preferably used in non-study visits in which visual acuity is not used as a study variable. This standard indicates that visual acuity should be measured only once in each participant visit (i.e., not without correction, with a pinhole, and after manifest refraction), so as to preserve the relative unfamiliarity of Chart 1 and Chart 2. The only exception is when Procedure II results in a 10 letter change in visual acuity (in either eye). In this case, a retest of visual acuity (of both eyes) after a manifest refraction is required.

Visual acuity may not be required to be measured in every clinic visit. For example, if a participant with a disease that is not expected to be subject to day-to-day fluctuations in acuity, who has been examined the previous week, returns to the clinic for an additional diagnostic procedure, e.g., perimetry or angiography, it would be unnecessary to retest visual acuity at the second visit.

Participants' pupils are not dilated at the time of visual acuity testing at any study visit. Pinhole acuity will not be tested. Visual acuity is optionally initially assessed utilizing the participant's current distance glasses or the previously obtained manifest refraction. Participants are asked to read the letters on the standard ETDRS Visual Acuity Chart. They start reading from the top left-most letters—first with the right eye and then with the left eye. A visual acuity score is calculated.

Procedure 1

Measurement of BCVA with Required Manifest Refraction

The visual acuity of participants is measured using a set of three Lighthouse Distance Visual Acuity Test charts (second edition), which are modified ETDRS Charts 1, 2 and R. If participants are illiterate, alternate versions of the "E" chart are available that also meet the requirements. Use of a retro-illuminated chart box is recommended but optional. For either retro-illuminated or front-lighted charts, the illumination of the charts must be even and meet the standards noted below. The charts and boxes are manufactured by Optelec US (Vista, Calif.) or Precision Vision (LaSalle, Ill.).

Visual acuity testing is required at a distance of four meters and, for participants with sufficiently reduced vision, at one meter. The 4-meter distance is preferably marked clearly and permanently and the 1-meter distance is preferably measured, with a 1-meter stick, with the participant in a chair.

Visual acuity charts 1 and 2 are used for testing the right and left eye, respectively, and Chart R is used for refraction. The features of the charts are five high-contrast Sloan letters in each of 14 lines of equal difficulty, and a geometric progression of letter size (and, thus, an arithmetic progression of the logarithm of minimum angle of resolution, logMAR) from line to line. Charts 1, 2 and R have different letter sequences. Participants are preferably prevented from seeing Charts 1 and 2 until refraction has been completed and the visual acuity test begins. If a box is not used to hold the charts, the charts are preferably mounted at a height such that the top of the third row of letters (0.8 logMAR) is 49±2 inches from the floor.

The dimensions of an optionally used retro-illuminated light box are 24¾ inches high by 25¾ inches wide by 7 inches deep. The box can be mounted on a wall or on a cylindrical stand manufactured by Lighthouse Low Vision Products. The stand is mounted on a five-pronged wheel base, with each prong about 14 inches long; two of the five wheels are lockable. The rear of the box provides storage space for the two charts not being used. When the box is mounted on the stand, its height can be varied. The light box is preferably mounted at a height such that the top of the third row of letters (0.8 logMAR) is 49±2 inches from the floor.

Room illumination is preferably between 50 and 125 foot candles as measured with a photometer held four feet from the floor and directed towards the ceiling. The chart is preferably evenly illuminated either in a retro-illuminated visual acuity light box or mounted on an evenly illuminated perpendicular wall at the specified lighting levels.

A distance of 4.00 meters (13 feet and 1.5 inches, or 157.5 inches) is used between the participant's eyes and the visual acuity chart for the 4-meter test. Preferably, the 4.00 meter measurement is exact. The permitted tolerance is only ±2 cm (0.02 meter) from cornea to chart surface in the 4-meter lane. For testing at one meter, the distance is preferably 1.00±0.01 meters (39 and ⅜ inches). A measuring tape or meter stick is preferably always be available to verify the chart distance, even if the examining chair is immovable or if reference marks are placed on the floor or walls. (Custodial and other staff have been known to move room furnishings about and clean-off marks from the floor or wall while performing their duties, necessitating re-establishing the correct distances for the lane.)

Refraction Technique

The technique described below is used whenever a manifest refraction and BCVA measurement is indicated by the study protocol. Any standard visual acuity chart, such as Refraction Chart R or a Projecto-Chart, and any test distance are used for determining the best lens correction in each eye, though using the 4-meter lane is recommended. If the standardized test (4-meters, Chart R) is not used, however, an over-refraction with spheres is preferably performed, using Chart R at four meters prior to testing visual acuity. Charts 1 and 2 are not used for refraction, only for visual acuity testing. The right eye is refracted first and then the left eye.

If the participant wears contact lenses and has glasses, he or she is told not to wear the contact lenses on the day of the examination. If the participant appears for the examination wearing contact lenses (because he or she has forgotten to follow the instructions or because he or she has no glasses), the contact lenses are removed and refraction and visual acuity testing should not begin for at least half an hour. Longer periods for corneal reshaping are needed if the participant is wearing hard contact lenses.

The result of a subjective refraction on a previous visit can be used as the beginning approximate refraction. If this is not available, then the following procedures are followed:

(a) If the participant's uncorrected visual acuity is 20/200 or better and the participant does not have glasses for distance vision, the beginning approximate refraction is no lens correction (piano);

(b) If the participant's uncorrected visual acuity is less than 20/200 in either eye with the participant's present distance glasses (or without correction, if the participant does not have glasses), retinoscopy is preferably performed by an examiner proficient in this procedure. An acceptable alternative is to conduct an arbitrary trial with any lenses to bring acuity to 20/200 or better; another is to use an automated refractor. The lens corrections obtained are used as the beginning approximate refraction for determining best-corrected visual acuity;

(c) If the participant's visual acuity is 20/200 or better with the participant's present distance glasses, the glasses are measured with a lensometer and these measurements are used as the beginning approximate refraction.

The trial frame is placed and adjusted on the participant's face so that the lens cells are parallel to the anterior plane of the orbits and centered in front of the pupils. (It is permissible to use a Phoroptor for subjective refraction. However, for testing visual acuity the lenses from the final Phoroptor refraction must be placed in a trial frame and the final sphere must be rechecked in the 4-meter lane. See information below about refining final spherical power.) The left eye is occluded and the beginning approximate refraction, as determined above, is placed in the right lens cells with the cylindrical correction anterior. Standard eye charts are read at a distance of 10 to 20 feet directly or with a mirror (closer if visual acuity is too poor for the participant to see the largest letters on the chart at this distance). Using the standard 4-meter visual acuity lane will obviate the need to switch locations between refraction measurements and acuity measures, so this is preferred.

Determination of Spherical Refraction

The visual acuity of the right eye is assessed and noted. A +0.50 sphere is then held in front of the right eye and the participant is asked if the vision is "better," "worse," or "no different" while he or she is looking at the smallest line read well.

1. If vision is improved or there is no change, the sphere in the trial frame is replaced with one that is one-half diopter more plus. The +0.50 sphere is held in front of the right eye again and the participant is asked again if the vision is "better," "worse," or "no different." This process of increasing the plus sphere in the trial frame is repeated until the participant says that the +0.50 sphere held in front of the trial frame makes the vision worse. When the participant responds that the vision is made "worse," the lens should be left in place for 10 to 15 seconds in an attempt to evaluate whether the participant is accommodating. If the vision clears during this period, the +0.50 sphere may be added again and succeeding attempts to evaluate additional plus lenses should be accompanied with a 10- to 15-second delay. If there is no evidence of unrelaxed accommodation, the delay period while assessing plus lenses is not necessary at any time further in the examination.

2. Whenever the participant says that the vision is "worse" and remains worse, the +0.50 sphere is removed from in front of the trial frame. By this process, the highest-plus or least-minus sphere that is tolerated without blurring the participant's vision is determined. After determining this highest-plus or least-minus sphere, the participant is asked to read the smallest line possible.

3. Next, a −0.37 sphere is held in front of the trial frame and the participant is asked if the vision is "better," "worse," or "no different." If vision is improved, the participant is requested to read the chart and if at least one more letter is read, the sphere in the trial frame is replaced by a sphere that is 0.25 diopter less plus. In certain situations, the participant is unable to read more letters, but is convinced that the vision is actually improved. If the examiner believes that this is the case, the additional minus lens can be added. At any stage in the examination, no more than 0.25 diopters of minus should be added without an increase in the number of letters read correctly. The additional minus lens should not be added if the participant reads fewer letters but states that acuity is better. There is a general attempt in this refraction protocol to avoid "over-minusing" the participants. However, when plus cylinders are in the refraction, one must be careful not to unnecessarily withhold minus which may be necessary for the participant to accept the needed plus cylinders later in the refraction. Minus spherical power is added in −0.25-diopter increments until the participant shows no further improvement in vision. If minus power is added, a +0.50 sphere is tried again to determine if more plus will be accepted.

4. If the participant says the vision is "not different" or "worse," no minus power should be added and the spherical determination is complete.

Herein, only plus cylinder techniques are presented. Minus cylinders may be used instead of plus cylinders to determine the best correction for the cylinder power and axis. If minus cylinders are used, the procedures must be revised to reflect the change in sign.

Cylinder Axis Determination

If the beginning approximate refraction contains a cylinder correction, changes in cylindrical axis are tested by adding a 0.25, 0.37, or 0.50 diopters cross-cylinder, first with the positive axis 45° to one side of the cylinder axis, and then with the positive axis 45° to the opposite side of the cylinder axis. Since neither position may produce a clear image, the participant is encouraged to select the position producing "less blur" while fixing on a single round letter on the line above the lowest line on the chart he or she is able to read when the cross-cylinder is not held up before the trial frame. If the participant cannot choose between the two positions of the cross-cylinder at the beginning of this test, the axis of the cylinder is moved 5° to 15°, first in one direction and then in the other, with the cross-cylinder being checked in each position to confirm that the original axis was indeed correct. If the participant prefers one position of the cross-cylinder to the other and the cylinder in the trial frame is plus, the axis of the cylinder is moved 5° to 15° toward the positive axis of the cross-cylinder when it is in the position found to be less blurry by the participant.

When the power of the cylinder is low or the participant's discrimination is poor, larger shifts produce more clear-cut answers. The cross-cylinder is tried again with the positive axis 45° first to one side and then to the opposite side of the new cylinder axis to determine which position is producing less blur.

If the participant finds one position less blurry, the axis of the plus cylinder is moved toward the positive axis of the cross-cylinder. Testing for change of axis is repeated until the participant finds neither position definitely better than the other.

Cylinder Power Determination

Change in cylinder power is tested by adding the cross-cylinder, first with the positive axis and then with the negative axis coincident with the cylinder axis. For this test, the participant is requested to focus attention on a round letter on the lowest line on the chart he or she is able to read. If the participant prefers the positive axis coincident with the cylinder axis, the power of the correcting plus cylinder is increased by an additional +0.25 diopter. If the participant prefers the negative axis coincident with the cylinder axis, the total power of the correcting plus cylinder is reduced by −0.25 diopter. The process is repeated until the participant finds neither position definitely better than the other. As plus cylinder is added, the examiner should recognize that the spherical equivalent of the refraction is being changed. More minus spheres may be needed as plus cylinders are added. When using plus cylinders for every 0.50 diopter of cylinder power added, the sphere should be changed by −0.25 diopter. If, at any time, the preference with the cross-cylinder indicates that cylinder power should be removed entirely, the 0.25 cylinder should be rotated 90° from its original position. The axis should be refined and the power should be tested again.

If the beginning refraction is a "pure" sphere, the presence of astigmatism is tested by arbitrarily placing a +0.25 cylinder at 180° in the trial frame, after having determined the highest-plus or least-minus sphere producing minimal blurring of vision, as described above. The refraction is then continued by using the cross-cylinder to test for cylinder axis and then cylinder power using the cross-cylinder technique outlined above. If, at any time, the preference with the cross-cylinder indicates that cylinder power should be removed entirely, the 0.25 cylinder should be rotated 90° from its original position and the power should be tested again. At this point, if the participant prefers additional power, it should be added. If, on the other hand, the participant prefers to remove the +0.25, it should be removed and the final refraction is then purely spherical. An example of this procedure follows: For example, with a beginning refraction: −2.50+0.25×37° and use of the cross-cylinder to check cylinder axis indicates that the participant prefers the 37° axis. If, on using the cross-cylinder to check cylinder power, the participant wants the 0.25 cylinder removed, rotate the cylinder to 127° and test for cylinder power again. If additional power is preferred, add it. If the preference with the cylinder at 127° is to remove the 0.25 cylinder, this should be done and the resulting refraction is −2.50 sphere.

Refining Final Spherical Power

When neither the power nor the axis of the cylinder can be improved, the power of the sphere is refined by testing with +0.25 sphere and −0.37 sphere and changing the spherical power. If the sphere is changed at this point, the cylinder should be rechecked. This process is repeated until no further significant lens changes are made.

This refraction protocol can be summarized as follows. First, having eliminated any possible accommodation with plus spheres, the spherical equivalent power is placed on the retina. Then the cylinder power and cylinder axis are assessed. This process of checking sphere, cylinder axis and cylinder power is repeated until there are no changes that result in an increased number of letters being read. Ideally, at the end of the refraction, the sphere is checked and the participant neither tolerates increased plus nor improves with increased minus spheres. Then the axis is checked and no change in axis is indicated. Finally, the cylindrical power is checked and no change in this is indicted. At this point, the refraction is completed. Sometimes this endpoint cannot be reached because there are an unending number of small corrections at each repetition of the process. When it becomes clear that these small changes are not resulting in an increased number of letters read correctly, the examiner terminates the refraction.

The lens corrections obtained in this way for the right eye are recorded in the study records as the corrections obtained by subjective refraction for the right eye. The entire process is repeated for the left eye, and these lens corrections are also recorded in the study records as the corrections obtained by subjective refraction for the left eye.

Adjustment for Non-Standardized Test Conditions During Refraction

If a test distance other than four meters is used for refraction, the participant should be taken to the site of visual acuity testing in the 4-meter lane. At this site, a final adjustment of the sphere should be made at four meters just before visual acuity testing, using Refraction Chart R with appropriate lighting while not allowing the participant to see Chart 1 or Chart 2. If this refraction differs from the initial refraction, this lens correction is recorded in the study records. Similarly, if a Phoroptor is used for the subjective refraction, a final check on the sphere is performed with a trial frame using the 4-meter refraction lane and Refraction Chart R. A change of spherical power in these circumstances does not require rechecking the cylinder power or axis.

Refraction for Participant with Poor Visual Acuity

If it is not possible to perform a subjective refraction at 10 to 20 feet because visual acuity is too poor for the participant to see the largest letters on the refraction chart at this distance, the refraction should be attempted at one meter. If the subjective refraction can be performed successfully at 1 meter, a +0.75 sphere should be subtracted from the 1-meter refraction to make the correction appropriate for the 4-meter distance. This correction should be noted in the study records in the space provided for distance subjective refraction. (Note: Visual acuity is tested first at the 4-meter distance even if the participant cannot be refracted at this distance. If the number of letters read correctly at four meters is 19 or less, visual acuity must also be tested at 1 meter, in which case the +0.75 sphere should be added to the 4-meter refraction.)

Determining Best-Corrected Visual Acuity

Testing at 4-Meters

Testing of all eyes begins at four meters. First, the right eye is tested with Chart 1 and then the left eye is tested with Chart 2. Each chart should remain hidden from view until the eye in question is ready for testing.

The distance from the participant's eyes to the visual acuity chart is preferably exactly 4.00 meters (13 feet and 1.5 inches, or 157.5 inches). The participant may stand or sit for the 4-meter visual acuity test. If the participant is seated, his or her back should fit firmly touching the back of the chair. The examiner should ensure that the participant is standing or sitting comfortably, that the head does not move forward or backward during the test and that the participant's eyes remain at the 4-meter distance.

The testing procedure for visual acuity is based on the principle that the objective is to test visual acuity and not intelligence or the ability to concentrate or follow or remember instructions (although all of these factors are involved).

The participant should be told that the chart has letters only and no numbers. If the participant forgets this instruction and reads a number, he or she should be reminded that the chart contains no numbers and the examiner should request a letter in lieu of the number. The examiner must record which letters were read correctly or incorrectly, not just how many (see Section 0). A Visual Acuity Worksheet of the Chart 1 and Chart 2 letters is used to record this while the examination is underway.

The participant is preferably asked to read slowly (at a rate not faster than about one letter per second) in order to achieve the best identification of each letter and to not proceed until the participant has given a definite response. It may be useful for the examiner to demonstrate the letter-a-second pace by reciting "A, B, C, . . . ". If, at any point, the participant reads quickly, he or she is asked to stop and read slowly. If the participant loses his or her place in reading or the examiner loses his or her place (possibly because the letters are read too quickly), the examiner asks the participant to go back to where the place was lost. Examiners never point to the chart or to specific letters on the chart or read any of the letters during the test.

Each letter is scored as right or wrong. Once a participant has identified a letter with a definite single-letter response and has read the next letter, a correction of the previous letter cannot be accepted. If the participant changes a response aloud (e.g., "That was a 'C,' not an 'O'") before he or she has read aloud the next letter, then the change should be accepted. If the participant changes a response after beginning to read the next letter, the change is not accepted.

When the participant says he or she cannot read a letter, he or she is encouraged to guess. If the participant identifies a letter as one of two or more letters, he or she is asked to choose one letter and, if necessary, to guess even if the next letter has already been read. The examiner may suggest that the participant turn or shake his or her head in any manner if this improves visual acuity. If the participant does this, care must be taken to ensure that the fellow eye remains covered. When it becomes evident that no further meaningful readings can be made, despite urgings to read or guess, the examiner should stop the test for that eye.

Testing at 1-Meter

Eyes reading 19 or fewer letters correctly at four meters are preferably tested at one meter. If the trial frame is to be removed when changing the test distance from four meters to one meter, the testing chart (Chart 1 or 2) should first be removed from view to prevent the participant from reading the chart with the fellow eye.

Before testing at 1 meter, a +0.75 sphere is added to the 4-meter correction already in the trial frame to compensate for the closer testing distance. The participant may stand or sit for the 4-meter test, but must sit for the 1-meter test. The avoidance of any head movement forward or backward is particularly important during the 1-meter test. The participant should be asked to read only the first six lines at one meter, making 30 letters the maximum score attainable at that distance.

After the test of the right eye is completed, occlude the left eye and replace Chart 1 by Chart 2. The test is repeated for the left eye, starting at four meters. When testing of the left eye is completed, Chart 2 should be removed from view; Chart R may be mounted in preparation for the next participant.

Scoring Best-Corrected Visual Acuity

The examiner records each letter identified correctly by circling the corresponding letter on a Visual Acuity Worksheet in the study records. Letters read incorrectly and letters for which no guesses are made are not marked on the form. Each letter read correctly is scored as one point. The score for each line (which ranges from zero if no letters are read correctly to five letters read correctly) and the total score for each eye are recorded on the Visual Acuity Worksheet after testing is completed. If testing at one meter is not required, 30 points are automatically scored for the 1-meter test. The total combined scores (i.e., the sum of the 4- and 1-meter scores) for each eye are recorded. The approximate Snellen fraction is determined based on the lowest line read with one or fewer mistakes, and is recorded on the Visual Acuity Worksheet in the study records.

Light Perception and No Light Perception

If visual acuity is so poor that the participant cannot read any of the largest letters at one meter (i.e., the number of letters read correctly at one meter is zero), light perception should be tested with an indirect ophthalmoscope in a darkened room. The indirect ophthalmoscope light should be in focus at three feet with the rheostat set at maximum voltage. From a distance of three feet, the beam should be directed in and out of the eye at least four times, and the participant should be asked to respond when he or she sees the light. If the examiner is convinced that the participant perceives the light, vision should be recorded as "light perception"; if not, vision should be recorded as "no light perception."

Procedure 2

Measurement of BCVA with Conditional Refraction

Visual acuity is measured with the correction established by manifest refraction on a previous visit. If visual acuity of one or both eyes has decreased or increased ten or more letters compared to the baseline measurement, a manifest refraction of both eyes should be performed. The procedure described in Procedure I: Measurement of BCVA with required manifest refraction, should be followed in this case. Otherwise, a manifest refraction is not required, and the visual acuity measured is recorded in the medical record.

If visual acuity is not a study defined endpoint (i.e., if after this change has occurred, the participant will continue to participate in the study and visual acuity will continue being measured as a study variable, the baseline value should be "reset" to this new value, which will be used for future study visits that require this approach for the measurement of visual acuity.

The measurement of visual acuity with conditional refraction requires the use of two scoring sheets. Both copies of scoring sheets should be maintained in the medical record.

Procedure 3

Measurement of BCVA without Manifest Refraction

Visual acuity is measured in the standard fashion, using a refractive correction obtained by one of the following methods. First, it is preferred that the result of a subjective refraction on the previous visit is used. If this is not available, then, if the participant wears distance correction, the spectacle correction is measured with a lensometer, and these measurements are used. If the participant does not wear distance correction, then the participant's refraction is measured objectively with the automated refractor and the measurement obtained is used. If automated refractor measurements cannot be obtained, then the measurement is the measurement obtained without correction.

The entire disclosure of each patent, patent application, and publication cited or described in this document is hereby incorporated herein by reference.

We claim:

1. A method for treating a decrease in visual acuity associated with a disease or disorder that causes the accumulation of fluid in the subretinal space of a patient comprising administering by topical ocular instillation of a composition consisting essentially of interferon-gamma in an amount of interferon-gamma effective to decrease the amount of fluid present in the subretinal space of the patient.

2. The method of claim 1 wherein the disease or disorder is age-related macular degeneration, chronic macular edema, diabetic retinopathy, retinal detachment, or uveitis.

3. The method of claim 2 wherein the retinal detachment is a result of retinal injury or surgery.

4. The method of claim 3 wherein the disease or disorder is peripheral vitreoretinopathy.

5. The method of claim 1 wherein the disease or disorder is glaucoma.

6. The method of claim 1 wherein the interferon-gamma is administered to the basolateral side of the retinal pigment epithelium.

7. The method of claim 1 wherein the interferon-gamma is administered to the anterior surface of the eye.

8. A method for treating age-related macular degeneration, chronic macular edema, diabetic retinopathy, retinal detachment, glaucoma, or uveitis comprising decreasing the amount of fluid present in the subretinal space of a patient suffering from such a disorder by administering by topical ocular instillation of a composition consisting essentially of interferon-gamma in an amount of interferon-gamma effective to decrease the amount of fluid present in the subretinal space of the patient.

9. The method of claim 8 wherein the retinal detachment is a result of retinal injury or surgery.

10. The method of claim 9 wherein the patient suffers from peripheral vitreoretinopathy.

11. The method of claim 8 wherein the interferon-gamma is administered to the basolateral side of the retinal pigment epithelium.

12. The method of claim 8 wherein the interferon-gamma is administered to the anterior surface of the eye.

13. A method for decreasing the amount of fluid present in the subretinal space of a patient comprising administering by topical ocular instillation of a composition consisting essentially of interferon-gamma in an amount of interferon-gamma effective to decrease the amount of fluid present in the subretinal space of the patient.

14. The method of claim 13 wherein the interferon-gamma is administered to the basolateral side of the retinal pigment epithelium by administration to the anterior surface of the eye.

15. The method of claim 13 wherein the patient suffers from age-related macular degeneration, chronic macular edema, diabetic retinopathy, retinal detachment, or uveitis.

16. The method of claim 15 wherein the retinal detachment is a result of retinal injury or surgery.

17. The method of claim 16 wherein the patient suffers from peripheral vitreoretinopathy.

18. The method of claim 13 wherein the patient suffers from glaucoma.

* * * * *